United States Patent
Teall et al.

(10) Patent No.: US 11,465,994 B2
(45) Date of Patent: Oct. 11, 2022

(54) MGLUR7 AGONIST COMPOUNDS FOR TREATING MGLUR7-REGULATED DISEASES, DISORDERS, OR CONDITIONS

(71) Applicant: Takeda Pharmaceutical Company Limited, Osaka (JP)

(72) Inventors: Martin Teall, Cambridge (GB);
Kathryn White, Cambridge (GB);
Stephen Mack, Cambridge (GB);
Gemma Liwicki, Cambridge (GB);
Anne Stephenson, Cambridge (GB);
Louise Dickson, Cambridge (GB)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 16/461,427

(22) PCT Filed: Nov. 17, 2017

(86) PCT No.: PCT/JP2017/042308
§ 371 (c)(1),
(2) Date: May 16, 2019

(87) PCT Pub. No.: WO2018/092921
PCT Pub. Date: May 24, 2018

(65) Prior Publication Data
US 2019/0345148 A1 Nov. 14, 2019

Related U.S. Application Data

(60) Provisional application No. 62/566,832, filed on Oct. 2, 2017.

(30) Foreign Application Priority Data

Nov. 18, 2016 (GB) ..................... 1619514

(51) Int. Cl.
C07D 413/04 (2006.01)
C07D 311/68 (2006.01)
C07D 401/12 (2006.01)
C07D 401/14 (2006.01)
C07D 407/04 (2006.01)

(52) U.S. Cl.
CPC .......... *C07D 413/04* (2013.01); *C07D 311/68* (2013.01); *C07D 401/12* (2013.01); *C07D 401/14* (2013.01); *C07D 407/04* (2013.01)

(58) Field of Classification Search
CPC .. C07D 413/04; C07D 311/68; C07D 401/04; C07D 401/12; C07D 401/14
See application file for complete search history.

(56) References Cited

FOREIGN PATENT DOCUMENTS

| WO | 96/006098 | 2/1996 |
|----|-----------|--------|
| WO | 96/30333 | 10/1996 |
| WO | 97/23466 | 7/1997 |
| WO | 97/030998 | 8/1997 |
| WO | 99/003859 | 1/1999 |
| WO | 99/05134 | 2/1999 |
| WO | 00/042044 | 7/2000 |
| WO | 01/029034 | 4/2001 |
| WO | 01/36417 | 5/2001 |
| WO | 01/60821 | 8/2001 |

(Continued)

OTHER PUBLICATIONS

Crupi, Frontiers in Mol Neuroscience, vol. 12, article 20, 1-11, 2019. (Year: 2019).*

(Continued)

*Primary Examiner* — D Margaret M Seaman
(74) *Attorney, Agent, or Firm* — Barnes & Thornburg LLP; Scott Rothenberger

(57) ABSTRACT

The present invention provides compounds of formula (I) and pharmaceutically acceptable salts thereof

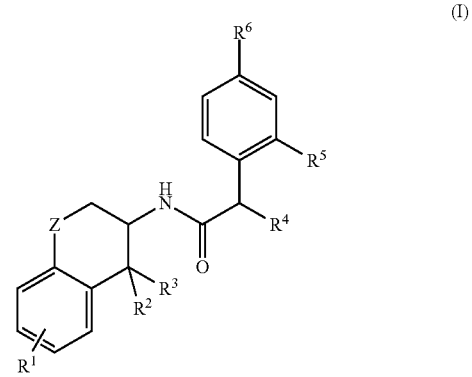

wherein Z, $R^1$, $R^2$, $R^3$, $R^4$, $R^5$ and $R^6$ are as defined in the specification, a process for their preparation, pharmaceutical compositions containing them and their use in therapy. The present invention further provides methods of treating at least one disease, disorder, or condition associated with the glutamatergic and GABAergic signalling pathways regulated in full or in part by metabotropic glutamate receptor 7 (mGluR7) by administering a compound of formula (I) or a pharmaceutically acceptable salt thereof to a subject. The compound may be a selective agonist of mGluR7, which modulates the release of at least one neurotransmitter in the subject.

25 Claims, 10 Drawing Sheets

(56) References Cited

FOREIGN PATENT DOCUMENTS

| WO | 02/08212 | 1/2002 |
|---|---|---|
| WO | 02/094794 | 11/2002 |
| WO | 02/096912 | 12/2002 |
| WO | 03/087102 | 10/2003 |
| WO | 03/087103 | 10/2003 |
| WO | 03/087104 | 10/2003 |
| WO | 2004/016616 | 2/2004 |
| WO | 2004016617 | 2/2004 |
| WO | 2004/019947 | 3/2004 |
| WO | 2007/025709 | 3/2007 |
| WO | 2016100281 A1 | 6/2016 |

OTHER PUBLICATIONS

Copinga, J Med Chem, vol. 36, 2891-2898, 1993. (Year: 1993).*
Conn, PNAS, vol. 103(2), 251-252, 2006. (Year: 2006).*
Tordjman, Current Neuropharmacology, vol. 15(3), 434-443, 2017. (Year: 2017).*
Fischer, Frontiers in Molecular Science, vol. 11, Article 387, pp. 1-14. (Year: 2018).*
Cecchi, R. et al., Synthesis and β-adrenergic activity of atypical β-adrenergic phenylethanolaminotetralin stereoisomers, European Journal of Medical Chemistry (1194) 29, pp. 259-267.
International Search Report and Written Opinion, dated Mar. 14, 2018, for PCT Application No. PCT/JP2017/042308, filed Nov. 17, 2017.
Bahi, "The selected metabotropic glutamate receptor 7 allosteric agonist AMN082 prevents reinstatement of extinguished ethanol-induced conditioned place preference in mice", Pharmacology, Biochemistry and Behavior, 101 (2012)193-200.
Begdoni, et al., "Defects during Mecp2 Null Embryonic Cortex Development Precede the Onset of Overt Neurological Symptoms", Cerebral Cortex, Jun. 2016, 26, 2517-2529.
Bertaso, et al., PICK1 uncoupling from mGluR7a causes absence-like seizures, Nat. Neurosci. Aug. 2008, (11)8;940-948.
Balonna, et al., Polymorphisms in the genes for mGluR 7 and 8: association studies with schizophrenia, Schizophrenia Research 47 (2001) 99-103.
Bough, et al., "Medial Perforant Path Inhibition Mediated mGluR7 is Reduced After Status Epilepticus", Journal of Neurophysiology, 92, 1549-1557, 2004.
Bradley, et al., "Distribution of Group III mGluRs in Rat Basal Ganglia with Subtype-Specific Antibodies", Annals New York Academy of Sciences, pp. 531-534, 1999.
Charng, et al., "Exome sequencing in mostly consanguineous Arab families with neurologic disease provides a high potential molecular diagnosis rate", BMC Medical Genomics, (2016) 9:42, 14 pages.
Choi, "The Role of Glutamate Neurotoxicity in Hypoxic-Ischemic Neuronal Death", Annual Review Neuroscience, 1990, 13: 171-182.
Conn, et al., "mGluR7's lucky number", PNAS, Jan. 10, 2006, vol. 103, No. 2, pp. 251-252.
Dolan, et al., "The selective metabotropic glutamate receptor 7 allosteric agonist AMN082 inhibits inflammatory pain-induced and incision-induced hypersensitvity in rat", Behavioural Pharmacology, 2009, 20: 596-604.
Dolan, et al., "Activation of metabotropic glutamate receptor 7 in spinal cord inhibits pain and hyperalgesia in a novel formalin model in sheep", Behavioural Pharmacology, 2011, 22: 582-588.
Domin, et al., "Neuroprotective effects of the allosteric agonist of metabotropic glutamate receptor 7 AMN082 on oxygen-glucose deprivation and kainate-induced neuronal cell death", Neurochemistry International, 88, 2015, 110-123.
Flor, et al., "Molecular and Cellular Biology of Neuroprotection in the CNS", Advances in Experimental Medicine and Biology, (2002) vol. 513, pp. 197-223.
Friedman, et al., "GRM7 variants confer susceptibility to age-related hearing impairment", Human Molecular Genetics, 2009, vol. 18, No. 4, 785-796.

Greco, et al., "Metabotropic Glutamate 7 Receptor Subtype Modulates Motor Symptoms in Rodent Models of Parkinson's Disease", The Journal of Pharmacology and Experimental Therapeutics, (2010) vol. 332, No. 3, pp. 1064-1071.
Gu, et al., Aβ Selectively Impairs mGluR7 Modulation of NMDA Signaling in Basal Forebrain Cholinergic Neurons Implication in Alzheimer's Disease, The Journal of Neuroscience, Oct. 8, 2014, 34(41), 13614-13628.
Gyetvai, et al., "mGluR7 Genetics and Alcohol: Intersection Yields Clues for Addiction", Neurochem Res., Jun. 2011, 36(6), 1087-1100.
Hovelso, et al., "Therapeutic Potential of Metabotropic Glutamate Receptor Modulators", Current Neuropharmacology, 2012, 10, 12-48.
Hu, et al., "Expression of mGluR7 and PCNA in the subventricularzone in adult rats following focal cerebral ischemia-reperfusion", SciFinder, American Chemical Society, (2008), 23(2), pp. 318-320.
Kahl, et al., "Metabotropic Glutamate Receptors 7 within the Nucleus Accumbens are Involved in Relief Learning in Rats", Current Neuropharmacology, 2016, 14, 405-412.
Kalinichev, et al., "ADX71743, a Potent and Selective Negative Allosteric Modulator of Metabotropic Glutamate Receptor 7: In Vitro and In Vivo Characterization", The Journal of Pharmacology and Experimental Therapeutics, Mar. 2013, 344:624-636.
Kandaswamy, et al., "Allelic Association, DNA Resequencing and Copy Number Variation at the Metabotropic Glutamate Receptor GRM7 Gene Locus in Bipolar Disorder", Am J Med Genet Part B (2014) 165B:365-372.
Konieczny, et al., "Contribution of the mGluR7 Receptor to antiparkinsonian-like effects in rats: a behavior study with the selective agonist AMN082", Pharmacological Reports, 2013, 65, 1194-1203.
Lau, et al., "Glutamate Receptors, neurotoxicity and neurodegeneration", Pflugers Arch—Eur. J. Physiol, (2010), 460:525-542.
Lewerenz, et al., "Chronic Glutamate Toxicity in Neurodegenerative Diseases—What is the Evidence?", Front. Neurosci, [2015,] 9:469.
Li, et al., "Metabotropic Glutamate Receptor 7 Modulates the Rewarding Effects of Cocaine in Rats: Involvement of a Ventral Pallidal GABAergic Mechanism", Neuropsychopharamacology, Jun. 2009, (34)7, 1783-1796.
Liu, et al., "Rare De Novo Deletion of Metabotropic Glutamate Receptor 7 [grm7] Gene in a Patient with Autism Spectrum Disorder", Ame. J. Med. Genet. (2015) Part B 1688:258-264.
Marafi, et al., "Biallelic GRM7 variants cause epilepsy, microcephaly, and cerebral atrophy", Annals of Clinical and Translational Neurology, 2020, pp. 1-18.
Neugebauer, et al., "The Glutamate Receptors", "Group III Metabotropic Glutamate Receptors (mGlu4, mGlu6, mGlu7, and mGlu8)", 2008, pp. 498-508.
Noroozi, et al., "Glutamate Receptor, Metabotropic 7 (GRM7) Gene Variations and Susceptibility to Autism: A Case-Control Study", Autism Research, 2016, 9:1611-1168.
O'Connor, et al., "Metabotropic Glutamate Receptor 7: At the Interface of Cognition and Emotion", European Journal of Pharmacology, 2010 (639), 123-131.
Palucha, et al., "Activation of the mGlu7 Receptor elicits antidepressant like effects in mice", Psychopharmacology, 2007, 194, 555-562.
Palucha-Poniewiera et al., "Activation of the mTOR signaling pathway in the antidepressant-like activity of the mGlu5 antagonist MTEP and the mGlu7 agonist AMN082 in the FST in rats", Neuropharmaology 82 (2014) 59-68.
Tassin, "Phasic and Tonic mGlu7 Receptor Activity Modulates the Thalamocortical Network", Frontiers in Neural Circuits, Apr. 25, 2016, vol. 10, Article 31, 1-19.
Vadasz, et al., "Glutamate Receptor Metabotropic 7 is cis-regulated in the mouse brain and modulates alcohol drinking", Genomics, (2007), 90, 690-702.
Yang, et al., "Role of Metabotropic Glutamate Receptor 7 in autism spectrum disorders: a pilot study", Life Sciences 92 (2013) 149-153.
Azari, et al., GRM7 polymorphisms and risk of schizophrenia in Iranian population, Metabolic Brain Disease, (2019) 34:847-852.

(56) References Cited

OTHER PUBLICATIONS

Besong, et al., Activation of Group III Metabotropic Glutamate Receptors Inhibits the Production of RANTES in Glial Cell Cultures, The Journal of Neuroscience, Jul. 1, 2002, 22(13):5403-5411.

Calabro, et al., Genetic variants associated with psychotic symptoms across psychiatric disorder, Neuroscience Letters, 720 (2020) 134754.

Chang, et al., A Conserved BDNF, Glutamate- and GABA-Enriched Gene Module Related to Human Depression identified by Coexpression Meta-Analysis and DNA Variant Genome-Wide Association Studies, PLOS One, Mar. 2014, vol. 9, Issue 3.

Chang, et al., The Association of GRM7 Single Nucleotide Polymorphisms with Age-Related Hearing Impairement in a Taiwanese Population, The Journal of International Advanced Otology, 2018, 14(2); 170-5.

Chen, et al., A novel relationship for schizophrenia, bipolar and major depressive disorder Part 3: Evidence from chromosome 3 high density association screen, The Journal of Comparative Neurology, 2018: 526; 59-79.

Fabbri, et al., Early antidepressant efficacy modulation by glutamatergic gene variants in the STAR*D, European Neuropsychopharmacology, (2013) 23, 612-621.

Fisher, et al., Metabotropic Glutamate Receptor 7: A New Therapeutic Target in Neurodevelopmental Disorders, Frontiers in Molecular Neuroscience, Oct. 2018, vol. 11, Article 387.

Fisher, et al., Phenotypic profiling mGlu7 knockout mice reveals new implications for neurodevelopmental disorders, Genes, Brain and Behavior, 2020: 1-14.

Fisher, et al., A GRM7 mutation associated with developmental delay reduces mGlu7 expression and produces neurological phenotypes, JCI Insight, 2021. https://doi.org/10.1172/jci.insight.143324.

Ghafouri-Fard, et al., Application of Artificial Neural Network for Prediction of Risk of Multiple Sclerosis Based on Single Nucleotide Polymorphism Genotypes, Journal of Molecular Neuroscience, (2020) 70:1081-1087.

Gogliotti, et al., mGlu7 potentiation rescues cognitive, social, and respiratory phenotypes in a mouse model of Rett syndrome, Sci Transl Med., Aug. 16, 2017, 9:(403).

Haider, et al., Biomarkers of Presbycusis and Tinnitus in a Portuguese Older Population, Frontiers in Aging Neurscience, Nov. 1, 2017, vol. 9, Article 346.

Hajasova, et al., Role of mGlu7 receptor in morphine rewarding effects is uncovered by a novel orthosteric agonist, Neuropharmacology, 131, (2018) 424-430.

Jantas, et al. Neuroprotective effects of metabtropic glutamate receptor group II and III activators against MPP(+)-induced cell death in human neuroblastoma SH-SYSY cells: The impact of cell differentiation state, Neuropharmacology, 83 (2014), 36-53.

Li, et al., Significant associateionof GRM7b and GRM8 genes with schizophrenia and major depressive disorder in the Han Chinese population, European Neuropsychopharmacology (2016) 26, 136-146.

Liang, et al., Variants of GRM7 as risk factor and response to antipsychotic therapy in schizophrenia, Translational Psychiatry, (2020) 10:83.

Luo, et al., Association of GRM7 Variants with Different Phenotype Patterns of Age-Related Hearing Impairment in an Elderly Male Han Chinese Population, PLOS One, Oct. 2013, vol. 8, Issue 10.

Marafi, et al., Biallelic GRM7 variants cause epilepsy, microcephaly, and cerebral atorphy, Annals of Clinical and Translatioinal Neurology, pp. 610-627.

Matyas, et al., Age-Related Hearing Impairment Associated NAT2, GRM7, GRHL2 Susceptibility Gene Polymorphisms and Haplotypes in Roma and Hungarian Populations, Pathology & Oncology Research, (2019) 25:1349-1355.

Mazdeh, et al., A single nucleotide polymorphism in the metabotropic glutamate receptor 7 gene is associated with multiple sclerosis in Iranian population, Multiple Sclerosis and Related Disorders, Dec. 28 (2019), 189-192.

Melroy-Greif, et al., Test for association of common variants in GRM7 with alcohol consumption, Alcohol (2016), 55:43-50.

Muglia, et al., Genome-wide association study of recurrent major depressive disorder in two European case-control cohorts. Molecular Psychology, (2010), 15, 589-601.

Newman, et al., GRM7 variants associated with age-related hearing loss based on auditory perception, Hear Research, Dec. 2012, 294(0), 125-132.

Nho, et al., Comprehensive Gene- and Pathway-Based Analysis of Depressive Symptoms in Older Adults, J Alzheimers Dis, Jan. 1, 2015, 45(4), 1197-1206.

Niu, et al., Association study of GRM7 polmorphisms and schizophrenia in the Chinese Han population, Neuroscience Letters, 604 (2015), 109-112.

Niu, et al., Association study of GRM7 polymorphisms with major depressive disorder in the Chinese Han population, Psychiatrics Genetics, 2017, 27:78-79.

Noroozi, et al., Glutamate receptor metabotropic 7 (GRM7) gene polymorphisms in mood disorders and attention deficit hyperactive disorder, Neurochemistry International, 129 (2019).

Ohtsuki, et al., A polymorphism of the metabotropic glutamate receptor mGluR7 (GRM7) gene is associated with schizophrenia, Science Research 101, (2008) 9-16.

Perez-Palma, et al., Overrepresentation of Glutamate Signaling in Alzheimer's Disease: Network-Based Pathway Enrichment Using Meta-Analysis of Genome-Wide Association Studies, PLOS One, Apr. 2014, vol. 9, Issue 4.

Pinteaux-Jones, et al., Myelin-induced microglial neurotoxicity can be controlled by microglial metabotropic glutamate receptors, Journal of Neurochemistry, 2008, 106, 442,454.

Reuter et al., Diagnostic Yield and Novel Candidate Genes by Exome Sequencing in 152 Consanguineous Families with Neurodevelopmental Disorders, JAMA Psychiatry, 2017, 74:3-293-299.

Ryan, et al., GWAS-identified risk variants for major depressive disorder: Preliminary support for an association with rate-life depressive symptoms and brain structural alterations, European Neuropsychopharmacology, (2016) 26, 113-125.

Sacchetti, et al., The GRM7 gene, early response to risperidone, and schizophrenia: a genome-wide association study and a confirmatory pharmacogenetic analysis, The Pharamcogenomics Journal, (2017), 17, 146-154.

Shyn, et al., Novel loci for major depression identified by genome-wide association study of STAR*D and meta-analysis of three studies, Molecular Psychiatry, Feb. 2011, 16(2), 202-215.

Song, et al., Pathogenic GRM7 mutations associated with neurodevelopmental disorders impair axon outgrowth and presynaptic terminal development, The Journal of Neuroscience, 2021, 10.1523, 2108-20.

Squillario, et al., A telescope GWAS analysis strategy, based on SNPs-genes-pathways ensamble and on multivariate algorithms, to characterize late onset Alzheimer's disease, Scientific Research, 2020, 10:12063.

Stevenson, et al., Antipsychotic pharmacogenomics in first episode psychosis: a role for glutamate genes, Transl Psychiatry (2016), 6, e739.

Strijbis, et al., Gluatarnate gene polymorphisms predict brain volumes in multiple sclerosis, Multiple Sclerosis Journal, 19(3) 281-288.

Sun, et al., GRIK4 and GRM7 gene may be potential indicator of venlafaxine treatment responses in Chinese of Han ethnicity. Medicine (2019), 98:19.

Van Laer, et al., A genome-wide association study for age-related hearing impairment in the Saami, European Journal of Human Genetics, (2010), 18: 685-693.

The Wellcome Trust Case Control Consortium, Genome-wide association study of 14,000 cases of seven common diseases and 3,000 shared controls, Nature, Jun. 7, 2007; 447(7145)1 661-678.

Yu, et al., Effect of GRM7 polymorphisms on the development of noise-induced hearing loss in Chinese Han workers: a nested case-conlrol study, BMC Medical Genetics, (2018) 19:4.

(56) References Cited

OTHER PUBLICATIONS

Zhang, et al., Anxiety-like behavior and dysregulation of miR-34a in triple transgenic mice of Alzheimer's disease, European Review for Medical and Pharmacological Sciences, 2016; 20; 2853-2862.
Zhou, et al., Evidence for selective microRNAs and their effectors as common long-term targets for the actions of mood stabilizers, Neuropsychopharmacology, May 2009, 34(6) 1395-1405.
Abdala, et al., "Deficiency of GABAergic synaptic inhibition in the Kolliker-Fuse area underlies respiratory dysrhythmia in a mouse model of Rett syndrome", Journal of Physiology, 594.1, (2016), pp. 223-237.
Banerjee, et al., Rett syndrome: genes, synapses, circuits, and therapeutics, Frontiers in Psychiatry, published May 8, 2012, vol. 3, Article 34, pp. 1-13.
Bedongi, et al., "Defects During Mecp2 Null Embryonic Cortex Development Precede the Onset of Overt Neurological Symptoms", Cerebral Cortex, Jun. 2016; 26: 2517-2529.
Boggio, et al., "Synaptic derminants of Rett syndrome", Frontiers in Synaptic Neuroscience, published Aug. 6, 2010, vol. 2, Article 29, pp. 1-11.
Chao, et al., Dysfunction in GABA signalling mediates autism-like sterotypies and Rett syndrome phenotypes, Nature, vol. 468, Nov. 11, 2010, pp. 263-269.
Khoury, et al., "GABA and Glutamate Pathways are Spatially and Developmentally Affected in the Brain of Mecp-2 Deficient Mice", PLOS ONE, Mar. 2014, vol. 1, Issue 3, pp. 1-15.
Fisher, et al., "Metabotropic Glutamate Receptor 7: A New Therapeutic Target in Neurodevelopmental Disorders", Frontiers in Molecular Neuroscience, published Oct. 23, 2018, vol. 11, Article 387, pp. 1-14.
Fisher, et al., "Phenotypic profiling of mGlu7 knockout mice reveals new implications for neurodevelopmental disorders". Genes, Brain and Behavior, Revised Mar. 3, 2020, pp. 1-14.
Fisher, et al., "A GRM7 mutation associated with developmental delay reduces mGlu7 expression and produces neurological phenotypes", JCI Insight, 2021,43 pages.
Gogliotti, et al., "mGlu7 protentiation rescues cognitive, social, and respiratory phenotypes in a mouse model of Rett syndrome", Science Translational Medicine, 2 Aug. 16, 2017, pp. 1-11.
Ip, et al., "Rett syndrome: insights into genetic, molecular and circuit mechanisms", Nature, Jun. 2018, vol. 19, pp. 1-15.
Larimore, et al., "Bdnf Overexpression in Hippocampal Neurons Prevents Dendritic Atorphy Caused by Rett-Associated MECP2 Mutations", Neurobiological Disorders, May 2009, 34(2); 199-211.
Masugi, et al., "Metabotropic Glutamate Receptor Subtype 7 Ablation Causes Deficit in Fear Response and Conditioned Taste Aversion", The Journal of Neuroscience, Feb. 1, 1999,10(3); 955-963.
Sansig, et al., "Increased Seizure Susceptibility in Mice Lacking Metabotropic Glutamate Receptor 7", The Journal of Neuroscience, Nov. 15, 2001, 21(22): 8734-8745.
Song, et al., "Pathogenic GRM7 mutations associated with neurodevelopmental disorders impair axon outgrown and presynaptic terminal development", The Journal of Neuroscience, Jan. 11, 2021, 54 pages.
CAS Registry No. 1956140-18-3; Entered STN: Jul. 20, 2016; 2H-1-Benzothiopyran-4-carboxamide, N-(3,4-dihydro-2H-1-benzopyran-3-yl)-3,4-dihydro-, 1,1-dixoxide.

CAS Registry No. 1954118-46-7; Entered STN: Jul. 18, 2016; 2H-1-Benzopyran-4-carboxamide, 3,4-dihydro-2,2-iimethyl-N-(1,2,3,4-tetrahydro-1-oxo-2-napthalenyl)-.
CAS Registry No. 1948238-69-4; Entered STN: Jul. 8, 2016; 1-Naphthalenecarboxamide, N-(3,4-dihydro-4-oxo-2H-1-5enzopyran-3-yl)-1,2,3,4-tetrahydro-1-methyl-.
CAS Registry No. 1797093-03-8; Entered STN: Jul. 8, 2016; 1H-Indazole-3-carboxamide, N-(3,4-dihydro-4-oxo-2H-1-benzopyran-3-yl)-.
CAS Registry No. 1647573-11-2; Entered STN: Feb. 15, 2015; Benzo[b]thiophene-3-carboxamide, N-(3,4-dihydro-2H-1-benzopyran-3-yl)-.
CAS Registry No. 1647374-16-0; Entered STN: Feb. 15, 2015; 1-Naphthalenecarboxamide, N-(3,4-dihydro-2H-1-5enzopyran-3-yl)-4-methoxy-.
CAS Registry No. 1606728-62-4; Entered STN: May 19, 2014; 1-Isoquinolinecarboxamide, N-(3,4-dihydro-2H-1-benzopyran-3-yl)-1,2,3,4-tetrahydro-.
CAS Registry No. 1606541-24-5; Entered STN: May 19, 2014; 1-Isoquinolinecarboxamide, N-(3,4-dihydro-2H-1-benzopyran-3-yl)-1,2,3,4-tetrahydro-, hydrochloride.
CAS Registry No. 1434999-13-9 ; Entered STN: Jun. 5, 2013; 4-Quinolinecarboxamide, 1,2-dihydro-2-oxo-N-(1,2,3,4-tetrahydro-2-naphthalenyl)-.
CAS Registry No. 1434684-24-8; Entered STN: Jun. 5, 2013; 4-Quinolinecarboxamide, N-(3,4-dihydro-2H-1-5enzopyran-3-yl)-1,2-dihydro-2-oxo-.
CAS Registry No. 1317433-16-1; Entered STN: Aug. 14, 2011;. 1-Isoquinolinecarboxamide, N-(1,2,3,4-tetrahydro-2-naphthalenyl)-.
CAS Registry No. 1288200-93-0; Entered STN: May 1, 2011; 4-Quinolinecarboxamide, 2-(4-pyridinyl)-N-(1,2,3,4-tetrahydro-2-naphthalenyl)-.
Selditz, U. et al., "Impact of Substituents on the Enantioseparation of Racemic 2-Amidotetralins on Polysaccharide Stationary Phases I. Chiralcel OD", Chirality, (8), 1996, pp. 574-578.
Selditz, U. et al., "Temperature effects on the chromatographic behaviour of racemic 2-ami-dotetralins on a Whelk-01 stationary phase in super- and subcritical fluid chromatography", Pharmazie, 54(3), 1999, pp. 183-191.
Search Report dated Aug. 10, 2017 for Great Brittain Application No. GB1619514.1.
Abe, et al., "Discovery of VU6005649, a CNS Penetrant mGlu7/8 Receptor PAM Derived from a Series of Pyrazolo [1,5-a]pyrimidines", ACS Med. Chem. Lett., 2017, 8, 1110-1115.
Bolonna, et al., "Polymorphisms in the genes for mGluR types 7 and 8: association studies with schizophrenia", Schizophrenia Research, 47, (2001) 99-103.
Bradley, et al., "Distribution and Developmental Regulation of Metabotropic Glutamate Receptor 7a in Rat Brain", J. Neurochemistry, vol. 71, No. 2,1998, pp. 636-645.
Martin, et al., "The Metabotropic Glutamate Receptor mGlu7 Activates Phosholipase C, Translocates Munc-13-1 Protein, and Potentiates Glutamate Release at Cerebrocortical Nerve Terminals", The Journal of Biological Chemistry, vol. 285, No. 23, pp. 17907-17917, Jun. 4, 2010.
Orellana, et al., "Executive functioning in Schizophrenia", Frontiers in Psychiatry, Published Jun. 24, 2013, vol. 1, Article 35, pp. 1-15.
Palazzo, et al., "Metabotropic Glutamate Receptor 7: From Synaptic Function to Therapeutic Implications", Current Neuropharmacology, 2016, vol. 14, No. 5, pp. 504-513.

* cited by examiner

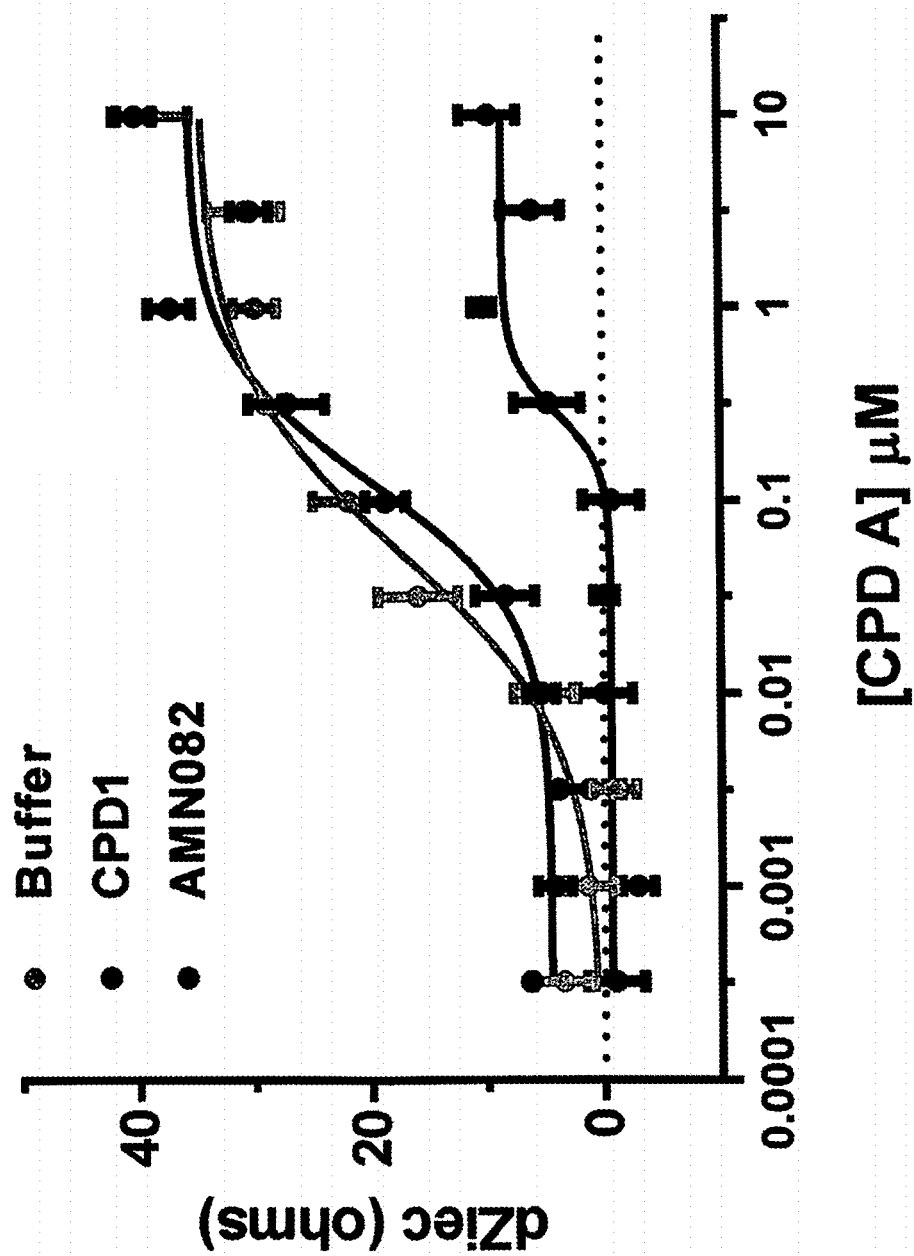

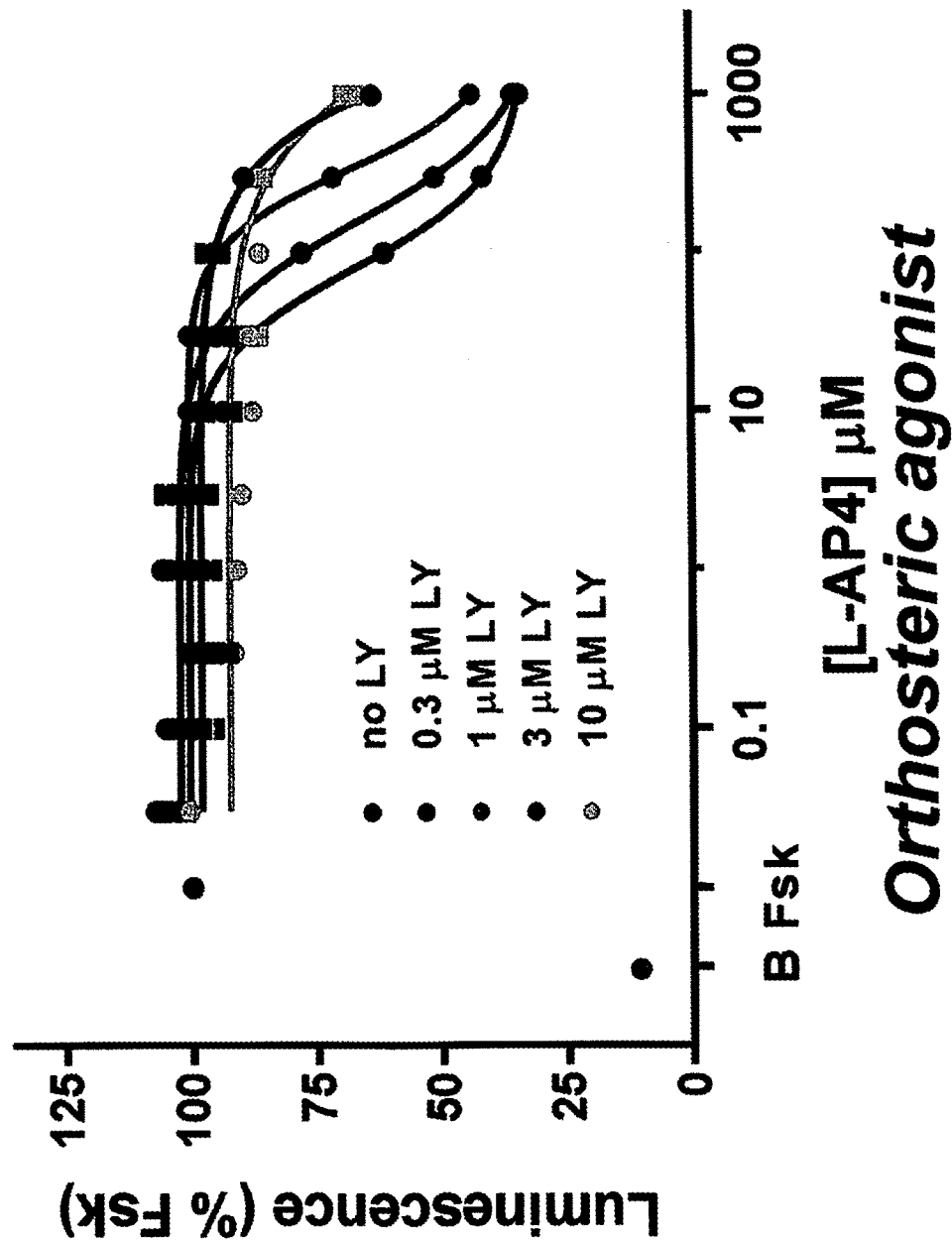

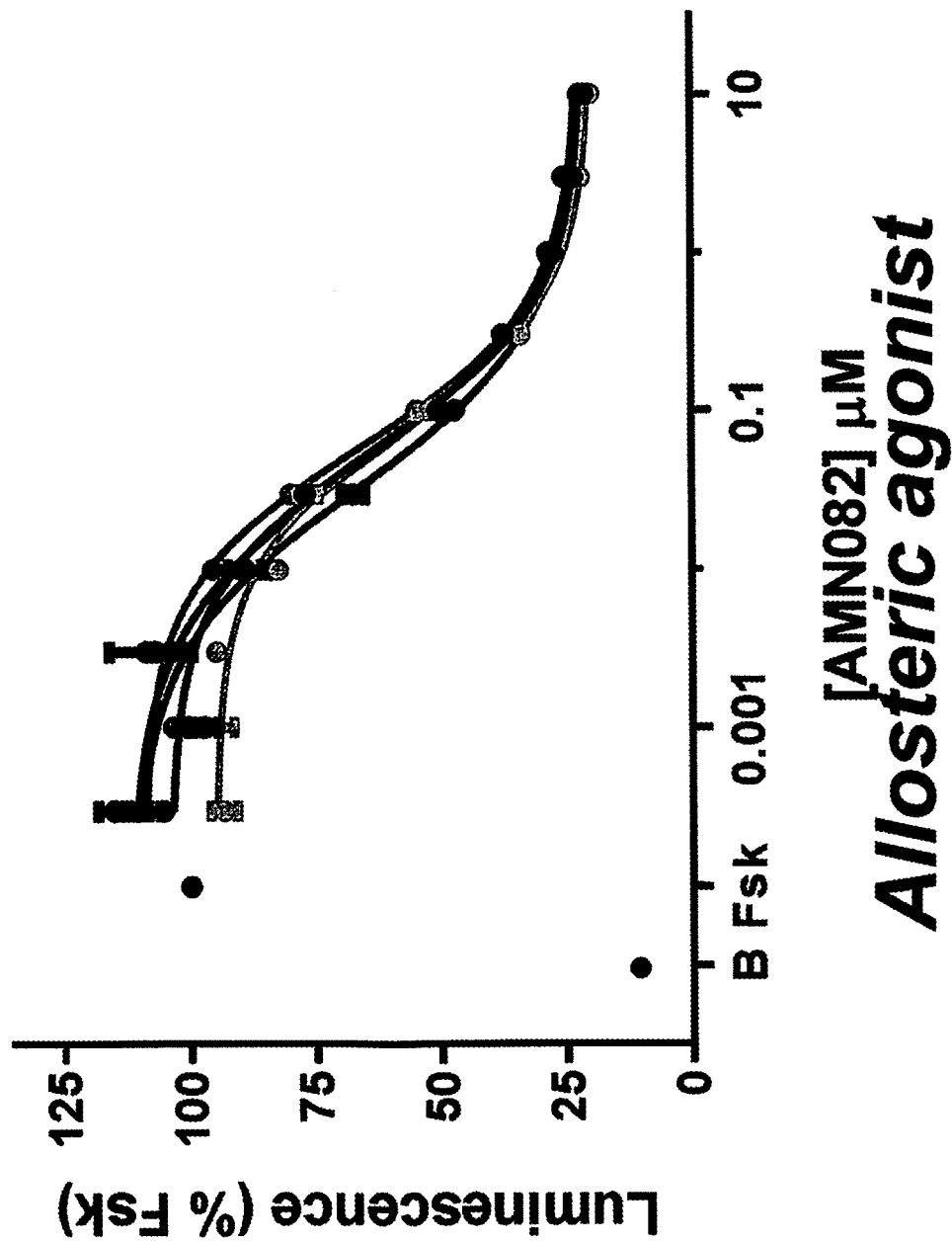

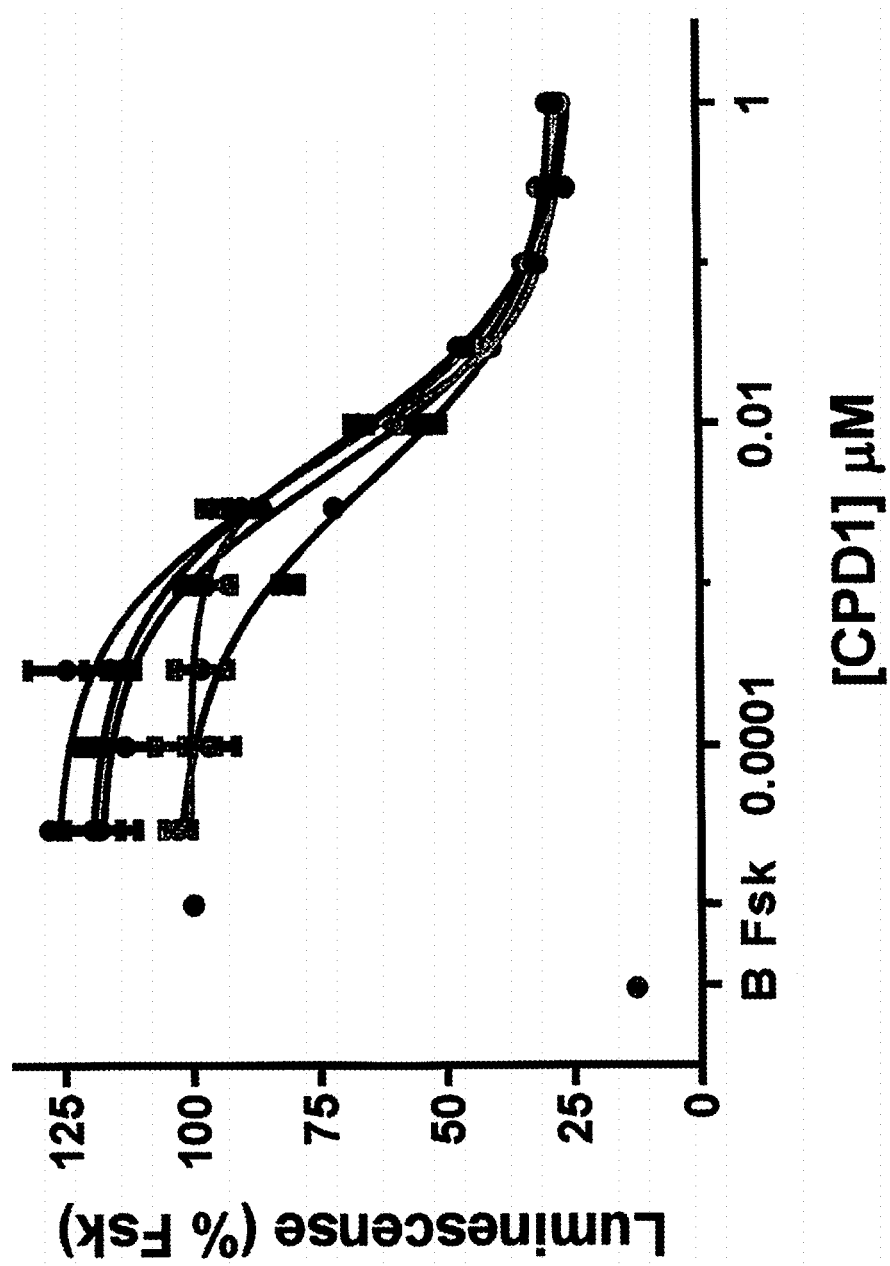

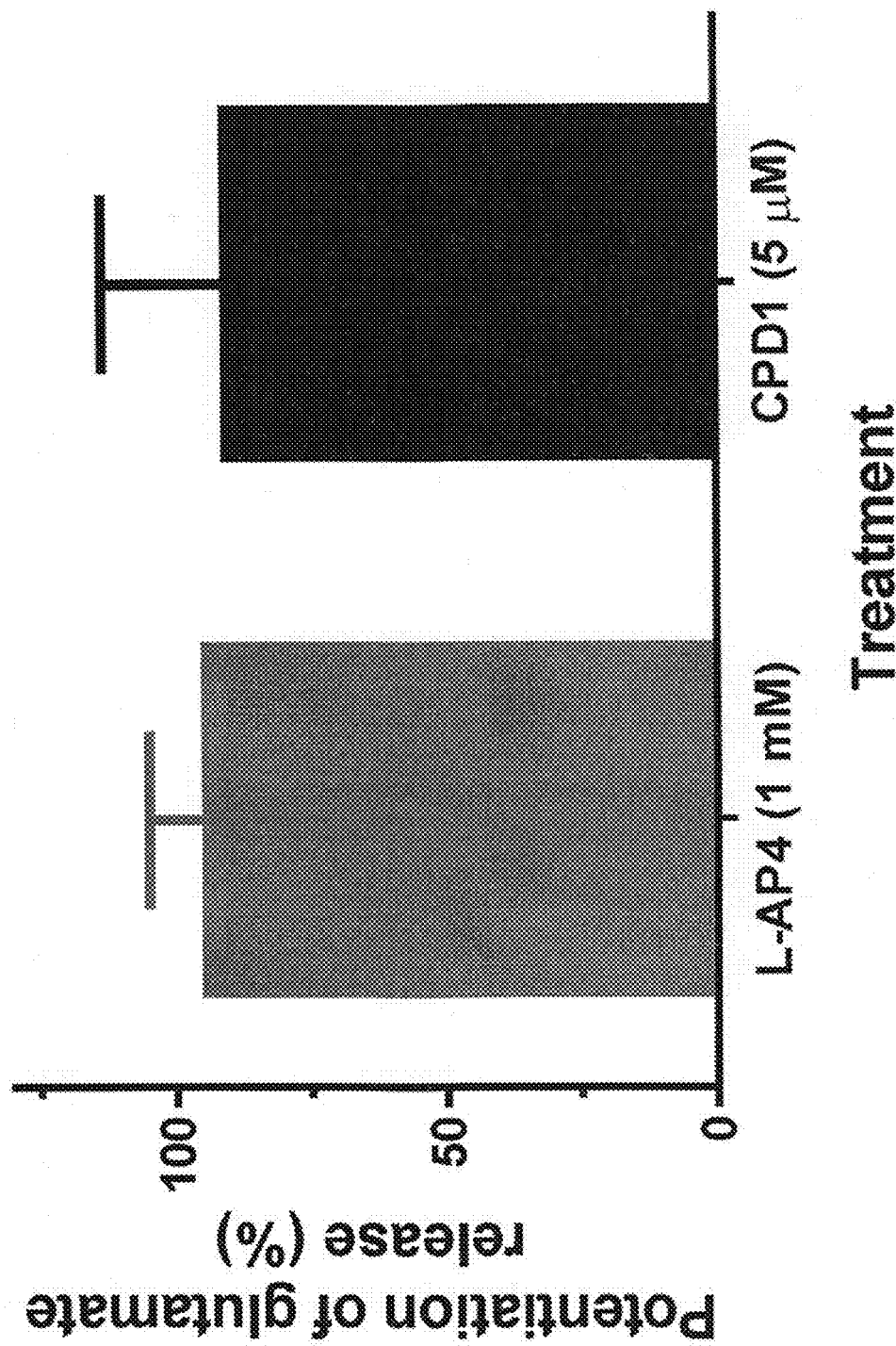

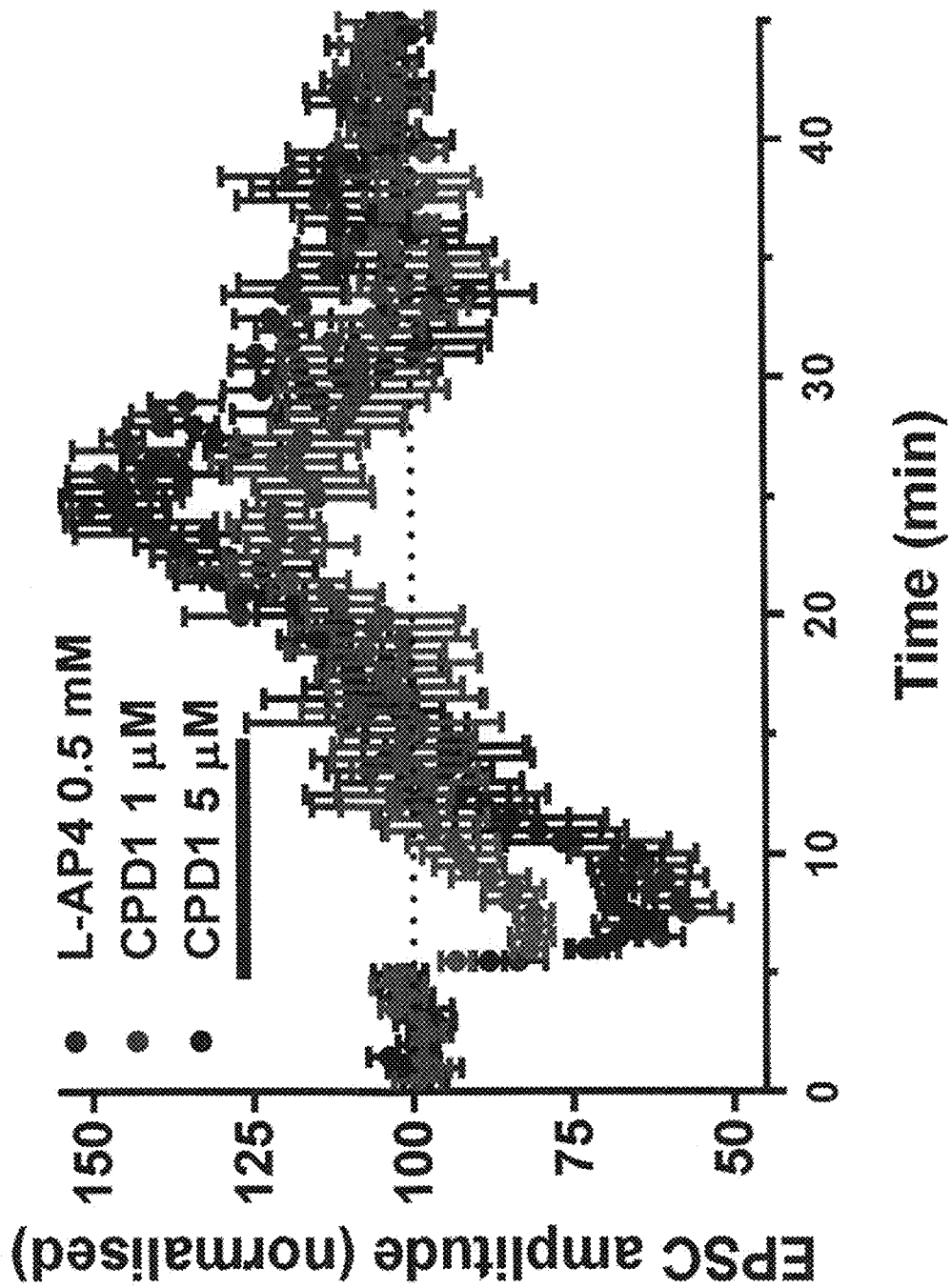

MGLUR7 AGONIST COMPOUNDS FOR TREATING MGLUR7-REGULATED DISEASES, DISORDERS, OR CONDITIONS

CROSS REFERENCE TO RELATED APPLICATIONS

This application is a National Stage Entry of PCT/JP2017/042308 filed Nov. 17, 2017 and claims prior to provisional patent application U.S. 62/566,832 filed Oct. 2, 2017 and to the United Kingdom application GB 1619514.1 filed Nov. 18, 2016, the contents of these applications are hereby incorporated by reference in their entireties.

FIELD OF THE INVENTION

The present invention relates to chromane and tetralin derivatives, processes for their preparation, pharmaceutical compositions containing them and their use in therapy, particularly for use in treating disorders associated with changes in one or both of the glutamatergic and GABAergic signalling pathways regulated in full or in part by metabotropic glutamate receptor 7 (mGluR7).

BACKGROUND OF THE INVENTION mGluR7 is a $G\alpha_{i/o}$ coupled receptor with widespread CNS expression (13). However, a lack of selective compounds has limited investigation of the therapeutic potential of mGluR7 (14). L-Glutamate is the major neurotransmitter in the mammalian central nervous system and activates both ionotropic and metabotropic glutamate receptors. L-Glutamate plays a central role in numerous physiological functions such as learning and memory (1), sensory perception, development of synaptic plasticity, motor control, respiration and regulation of cardiovascular function. Thus, an imbalance in glutamatergic neurotransmission often underlies many neuropathological conditions.

The metabotropic glutamate receptors are a family of G protein-coupled receptors that have been divided into three groups on the basis of sequence homology, putative signal transduction mechanisms and pharmacologic properties. Group I includes mGluR1 and mGluR5 and these receptors have been shown to activate phospholipase C. Group II includes mGluR2 and mGluR3 whilst Group III includes mGluR4, mGluR6, mGluR7 and mGluR8. Group II and III receptors are linked to the inhibition of the cyclic AMP cascade but differ in their agonist selectivity.

mGluR7 is an inhibitory GPCR expressed pre-synaptically at the synaptic cleft on GABAergic and glutamatergic neurons. mGluR7 can influence neuronal excitability by modulating neurotransmitter release and is therefore an attractive target for many neurological and psychiatric diseases, such as Parkinson's disease (2, 3); dementia associated with Parkinson's disease (3, 4); Alzheimer's disease (5); Huntington's Chorea (6); amyotrophic lateral sclerosis and multiple sclerosis; bipolar disorder (6, 7); psychiatric diseases such as schizophrenia, post-traumatic stress disorder, anxiety disorders and depression (1,4, 6, 8-11); and addiction. They may also be useful in treating age-related hearing loss/tinnitus (12).

There is a need for treatment of the above conditions and others described herein with compounds that are mGluR7 modulators. The present invention provides modulators of mGluR7.

SUMMARY OF THE INVENTION

Various embodiments of the inventions described herein describe a compound of formula (I) or a pharmaceutically acceptable salt thereof

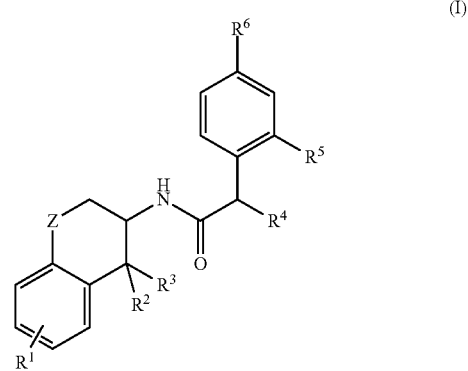

wherein
$R^1$ represents hydrogen or halogen;
$R^2$ represents hydrogen, hydroxyl, $C_1$-$C_6$ alkyl, $C_1$-$C_6$ haloalkyl, $C_1$-$C_6$ alkoxy, $C_1$-$C_6$ haloalkoxy, —N($R^7$)$_2$ or —SO$_2R^8$;
$R^3$ represents hydrogen or $C_1$-$C_3$ alkyl;
or $R^2$ and $R^3$ together form =O;
$R^4$ represents cyano, hydroxyl, —N($R^9$)$_2$, $C_1$-$C_6$ alkyl, $C_3$-$C_6$ cycloalkyl, $C_1$-$C_6$ alkoxy, $C_3$-$C_6$ cycloalkoxy, $C_1$-$C_6$ alkylcarbonyl, $C_3$-$C_6$ cycloalkylcarbonyl, $C_1$-$C_6$ alkoxycarbonyl, $C_3$-$C_6$ cycloalkoxycarbonyl, —(CH$_2$)$_m$R$^{10}$, —O(CH$_2$)$_m$R$^{10}$ or —NH(CH$_2$)$_m$R$^{10}$, wherein each of the alkyl, cycloalkyl, alkoxy, cycloalkoxy, alkylcarbonyl, cycloalkylcarbonyl, alkoxycarbonyl and cycloalkoxycarbonyl moieties is independently unsubstituted or substituted with at least one substituent independently selected from halogen, cyano, hydroxyl, oxo, methylamino, dimethylamino, $C_1$-$C_3$ alkyl, $C_1$-$C_3$ haloalkyl, $C_1$-$C_3$ alkoxy and $C_1$-$C_3$ haloalkoxy;
$R^5$ represents hydrogen or halogen;
or $R^4$ and $R^5$ together with the benzyl group to which they are attached form a 5- to 7-membered carbocyclic or heterocyclic ring, the heterocyclic ring comprising at least one ring heteroatom independently selected from nitrogen, oxygen and sulphur atoms, wherein the carbocyclic or heterocyclic ring is unsubstituted or substituted with at least one substituent independently selected from halogen, cyano, hydroxyl, oxo, amino, methylamino, dimethylamino, $C_1$-$C_6$ alkyl, $C_1$-$C_6$ haloalkyl, $C_1$-$C_6$ alkoxy, $C_1$-$C_6$ haloalkoxy, —(CH$_2$)$_n$R$^{11}$ and —O(CH$_2$)$_n$R$^{11}$;
$R^6$ represents hydrogen, halogen, $C_1$-$C_6$ alkyl or $C_1$-$C_6$ haloalkyl;
$R^7$ independently represents hydrogen, $C_1$-$C_6$ alkyl, $C_1$-$C_6$ haloalkyl, $C_4$-$C_6$ cycloalkyl, ($C_3$-$C_6$ cycloalkyl)methyl, 4- to 6-membered heterocycloalkyl, (3- to 6-membered heterocycloalkyl)methyl or —COR$^{12}$, or two $R^7$ together with the nitrogen atom to which they are attached form a saturated or unsaturated 4- to 7-membered heterocyclic ring optionally comprising one or more further ring heteroatoms independently selected from nitrogen, oxygen and sulphur atoms, the heterocyclic ring being unsubstituted or substituted with at least one substituent independently selected from halogen, cyano, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy;

$R^8$ represents $C_1$-$C_3$ alkyl, $C_3$-$C_6$ cycloalkyl or ($C_3$-$C_6$ cycloalkyl)methyl;

$R^9$ independently represents methyl, $C_3$-$C_6$ alkyl or $C_1$-$C_6$ haloalkyl, or two $R^9$ together with the nitrogen atom to which they are attached form a saturated or unsaturated 4- to 7-membered heterocyclic ring optionally comprising one or more further ring heteroatoms independently selected from nitrogen, oxygen and sulphur atoms, the heterocyclic ring being unsubstituted or substituted with at least one substituent independently selected from halogen, cyano, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy;

$R^{10}$ represents a saturated or unsaturated 3- to 7-membered carbocyclic ring or a saturated or unsaturated 4- to 7-membered heterocyclic ring, the heterocyclic ring comprising at least one ring heteroatom independently selected from nitrogen, oxygen and sulphur atoms, wherein the carbocyclic or heterocyclic ring is unsubstituted or substituted with at least one substituent independently selected from halogen, cyano, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy;

$R^{11}$ represents a saturated or unsaturated 3- to 7-membered carbocyclic ring or a saturated or unsaturated 4- to 7-membered heterocyclic ring, the heterocyclic ring comprising at least one ring heteroatom independently selected from nitrogen, oxygen and sulphur atoms, wherein the carbocyclic or heterocyclic ring is unsubstituted or substituted with at least one substituent independently selected from halogen, cyano, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy;

$R^{12}$ represents a saturated or unsaturated 3- to 7-membered carbocyclic ring or a saturated or unsaturated 4- to 7-membered heterocyclic ring, the heterocyclic ring comprising at least one ring heteroatom independently selected from nitrogen, oxygen and sulphur atoms, wherein the carbocyclic or heterocyclic ring is unsubstituted or substituted with at least one substituent independently selected from halogen, cyano, hydroxyl, oxo, amino, methylamino, dimethylamino, $C_1$-$C_3$ alkyl, $C_1$-$C_3$ haloalkyl, $C_1$-$C_3$ alkoxy, $C_1$-$C_3$ haloalkoxy and —CON($R^{13}$)$_2$;

$R^{13}$ independently represents hydrogen or $C_1$-$C_3$ alkyl;

Z represents —$CH_2$— or —O—;

m is 0, 1, 2 or 3; and n is 0, 1, 2 or 3.

In some embodiments of the compound described herein, $R^1$ represents hydrogen or fluorine. In some embodiments of the compound described herein, $R^2$ represents hydrogen, hydroxyl, $C_1$-$C_3$ alkyl, $C_1$-$C_3$ haloalkyl, $C_1$-$C_3$ alkoxy, $C_1$-$C_3$ haloalkoxy, —N($R^7$)$_2$ or —SO$_2$R$^8$; $R^7$ independently represents hydrogen, $C_1$-$C_3$ alkyl, $C_1$-$C_3$ haloalkyl or —COR$^{12}$, or two $R^7$ together with the nitrogen atom to which they are attached form a saturated or unsaturated 4-, 5- or 6-membered heterocyclic ring optionally comprising one, two or three further ring heteroatoms independently selected from nitrogen and oxygen atoms, the heterocyclic ring being unsubstituted or substituted with one, two, three or four substituents independently selected from halogen, hydroxyl, amino, methylamino, dimethylamino, $C_1$-$C_3$ alkyl, $C_1$-$C_3$ haloalkyl, $C_1$-$C_3$ alkoxy and $C_1$-$C_3$ haloalkoxy; $R^8$ represents $C_1$-$C_3$ alkyl; $R^{12}$ represents a saturated or unsaturated 5- or 6-membered carbocyclic ring or a saturated or unsaturated 5- or 6-membered heterocyclic ring, the heterocyclic ring comprising one, two or three ring heteroatoms independently selected from nitrogen and oxygen atoms, wherein the carbocyclic or heterocyclic ring is unsubstituted or substituted with one, two or three substituents independently selected from halogen, hydroxyl, amino, methylamino, dimethylamino, $C_1$-$C_3$ alkyl, $C_1$-$C_3$ haloalkyl, $C_1$-$C_3$ alkoxy, $C_1$-$C_3$ haloalkoxy and —CON($R^{13}$)$_2$; and $R^{13}$ independently represents hydrogen or $C_1$-$C_3$ alkyl. In some embodiments of the compound described herein, $R^3$ represents hydrogen, methyl, or ethyl.

In some embodiments of the compound described herein, $R^4$ represents hydroxyl, —N($R^9$)$_2$, $C_1$-$C_3$ alkyl, $C_3$-$C_6$ cycloalkyl, $C_1$-$C_3$ alkoxy, $C_3$-$C_6$ cycloalkoxy, $C_1$-$C_3$ alkylcarbonyl, $C_3$-$C_6$ cycloalkylcarbonyl, $C_1$-$C_3$ alkoxycarbonyl, $C_3$-$C_6$ cycloalkoxycarbonyl, —(CH$_2$)$_m$R$^{10}$, —O(CH$_2$)$_m$R$^{10}$ or —NH(CH$_2$)$_m$R$^{10}$, wherein each of the alkyl, cycloalkyl, alkoxy, cycloalkoxy, alkylcarbonyl, cycloalkylcarbonyl, alkoxycarbonyl and cycloalkoxycarbonyl moieties is independently unsubstituted or substituted with one, two or three substituents independently selected from halogen, hydroxyl, methylamino, dimethylamino, $C_1$-$C_3$ alkyl, $C_1$-$C_3$ haloalkyl, $C_1$-$C_3$ alkoxy and $C_1$-$C_3$ haloalkoxy; $R^9$ independently represents methyl, $C_3$-$C_6$ alkyl or $C_1$-$C_6$ haloalkyl, or two $R^9$ together with the nitrogen atom to which they are attached form a saturated or unsaturated 4-, 5- or 6-membered heterocyclic ring optionally comprising one or two further ring heteroatoms independently selected from nitrogen and oxygen atoms, the heterocyclic ring being unsubstituted or substituted with one, two or three substituents independently selected from halogen, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy; $R^{10}$ represents a saturated or unsaturated 3-, 4-, 5- or 6-membered carbocyclic ring or a saturated or unsaturated 4-, 5- or 6-membered heterocyclic ring, the heterocyclic ring comprising one, two or three ring heteroatoms independently selected from nitrogen and oxygen atoms, wherein the carbocyclic or heterocyclic ring is unsubstituted or substituted with one, two or three substituents independently selected from halogen, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy; and m is 0, 1 or 2.

In some embodiments of the compound described herein, $R^5$ represents hydrogen or fluorine. In some embodiments of the compound described herein, $R^4$ and $R^5$ together with the benzyl group to which they are attached form a 5- or 6-membered carbocyclic or heterocyclic ring, the heterocyclic ring comprising one, two or three ring heteroatoms independently selected from nitrogen and oxygen atoms, wherein the carbocyclic or heterocyclic ring is unsubstituted or substituted with one, two or three substituents independently selected from halogen, hydroxyl, oxo, amino, methylamino, dimethylamino, $C_1$-$C_4$ alkyl, $C_1$-$C_4$ haloalkyl, $C_1$-$C_4$ alkoxy, $C_1$-$C_4$ haloalkoxy, —(CH$_2$)$_n$R$^{11}$ and —O(CH$_2$)$_n$R$^{11}$; $R^{11}$ represents a saturated or unsaturated 3-, 4-, 5- or 6-membered carbocyclic ring or a saturated or unsaturated 5- or 6-membered heterocyclic ring, the heterocyclic ring comprising one, two or three ring heteroatoms independently selected from nitrogen and oxygen atoms, wherein the carbocyclic or heterocyclic ring is unsubstituted or substituted with one, two or three substituents independently selected from halogen, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy; and n is 0, 1, 2 or 3.

In some embodiments of the compound described herein, $R^6$ represents hydrogen or halogen. In some embodiments of the compound of formula (I) described herein is selected from: (2S)—N-((cis)-4-hydroxy-3,4-dihydro-2H-1-benzopyran-3-yl)-2-phenylpropanamide; (2S)—N-((trans)-4-hydroxy-3,4-dihydro-2H-1-benzopyran-3-yl)-2-phenylpropanamide; (2S)—N-((cis)-6-fluoro-4-hydroxy-3,4-dihydro-2H-1-benzopyran-3-yl)-2-phenylpropanamide; (2S)—N-(4-oxo-3,4-dihydro-2H-1-benzopyran-3-yl)-2-phenylpropanamide; (2S)—N-((cis)-4-hydroxy-4-methyl-3,4-dihydro-2H-1-benzopyran-3-yl)-2-phenylpropanamide; (2S)—N-[(cis)-4-(methylamino)-3,4-dihydro-2H-1-benzopyran-3-yl]-2-phenylpropanamide; (2S)—N-((trans)-4-methoxy-3,4-dihydro-2H-1-benzopyran-3-yl)-2-phenylpropanamide; (2S)—N-((trans)-4-methanesulfonyl-3,4-dihydro-2H-1-benzopyran-3-yl)-2-phenylpropanamide; (2S)—N-[(trans)-4-(methylamino)-3,4-dihydro-2H-1-benzopyran-3-yl]-2-phenylpropanamide; (1S)-2-(cyclopropylmethyl)-N-((trans)-4-methoxy-3,4-dihydro-2H-1-benzopyran-3-yl)-3-oxo-1,2,3,4-tetrahydroisoquinoline-1-carboxamide; (2S)-2-(4-fluorophenyl)-N-((trans)-4-methanesulfonyl-3,4-dihydro-2H-1-benzopyran-3-yl) propanamide; (2S)-2-(4-chlorophenyl)-N-((trans)-4-methanesulfonyl-3,4-dihydro-2H-1-benzopyran-3-yl) propanamide; (2S)-2-(4-fluorophenyl)-N-[(trans)-4-(methylamino)-3,4-dihydro-2H-1-benzopyran-3-yl] propanamide; (2S)-2-(4-fluorophenyl)-N-[(trans)-4-(methylamino)-3,4-dihydro-2H-1-benzopyran-3-yl] propanamide; 2-(4-fluorophenyl)-N-((trans)-4-methoxy-3,4-dihydro-2H-1-benzopyran-3-yl)-2-[3-(trifluoromethoxy)azetidin-1-yl]acetamide; 2-(2,4-difluorophenyl)-N-((trans)-4-methoxy-3,4-dihydro-2H-1-benzopyran-3-yl)-2-[3-(trifluoromethoxy)azetidin-1-yl]acetamide; (1S)-2-(3-fluoropropyl)-N-((trans)-4-methoxy-3,4-dihydro-2H-1-benzopyran-3-yl)-3-oxo-1,2,3,4-tetrahydroisoquinoline-1-carboxamide; N-((trans)-4-methoxy-3,4-dihydro-2H-1-benzopyran-3-yl)-2-[(oxan-4-yl)methyl]-3-oxo-1,2,3,4-tetrahydroisoquinoline-1-carboxamide; N-((trans)-4-methoxy-3,4-dihydro-2H-1-benzopyran-3-yl)-3-oxo-2-[(pyridin-2-yl)methyl]-1,2,3,4-tetrahydroisoquinoline-1-carboxamide; 2-(cyclopropylmethoxy)-2-(4-fluorophenyl)-N-((trans)-4-methoxy-3,4-dihydro-2H-1-benzopyran-3-yl) acetamide; 2-(2,4-difluorophenyl)-N-((trans)-4-methoxy-3,4-dihydro-2H-1-benzopyran-3-yl)-2-[(2-methylpyrimidin-4-yl)oxy]acetamide; 2-(2,4-difluorophenyl)-N-((trans)-4-methoxy-3,4-dihydro-2H-1-benzopyran-3-yl)-2-(2-oxo-1,2-dihydropyridin-1-yl)acetamide; $N^1$-(trans)-{3-[(2S)-2-(4-fluorophenyl)propanamido]-3,4-dihydro-2H-1-benzopyran-4-yl}-$N^2$-methylbenzene-1,2-dicarboxamide; (2S)-2-(4-fluorophenyl)-N-[(trans)-4-(pyrrolidin-1-yl)-3,4-dihydro-2H-1-benzopyran-3-yl]propanamide; (2S)—N-[(trans)-4-(azetidin-1-yl)-3,4-dihydro-2H-1-benzopyran-3-yl]-2-(4-fluorophenyl)propanamide; (2S)—N-[(trans)-4-(dimethylamino)-3,4-dihydro-2H-1-benzopyran-3-yl]-2-(4-fluorophenyl)propanamide; (2S)—N-[(trans)-4-(3,3-difluoropyrrolidin-1-yl)-3,4-dihydro-2H-1-benzopyran-3-yl]-2-(4-fluorophenyl)propanamide; (2S)-2-(4-fluorophenyl)-N-[(trans)-4-(morpholin-4-yl)-3,4-dihydro-2H-1-benzopyran-3-yl]propanamide; (1S)-2-(cyclopropylmethyl)-N-((trans)-4-hydroxy-3,4-dihydro-2H-1-benzopyran-3-yl)-3-oxo-1,2,3,4-tetrahydroisoquinoline-1-carboxamide; (2S)-2-(4-fluorophenyl)-N-((cis)-4-hydroxy-3,4-dihydro-2H-1-benzopyran-3-yl)propanamide; and enantiomers, diastereoisomers and mixtures thereof; and pharmaceutically acceptable salts of any of the foregoing.

Various embodiments of the invention herein provide a process for the preparation of a compound of formula (I) or a pharmaceutically acceptable salt thereof as defined herein which comprises reacting a compound of formula (II) or a salt thereof

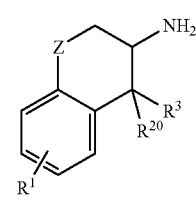

in which Z, $R^1$ and $R^3$ are as defined in formula (I), and $R^{20}$ represents hydrogen, hydroxyl, $C_1$-$C_6$ alkyl, $C_1$-$C_6$ haloalkyl, $C_1$-$C_6$ alkoxy, $C_1$-$C_6$ haloalkoxy, —N($R^7$)$_2$, —SO$_2$$R^8$ or —SR$^8$, with a compound of formula (III) or a salt thereof

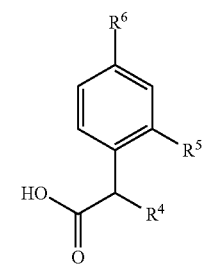

in which $R^4$, $R^5$ and $R^6$ are as defined in formula (I);
and optionally thereafter carrying out one or more of the following procedures:
    converting a compound of formula (I) into another compound of formula (I)
    removing any protecting groups
    forming a pharmaceutically acceptable salt.

Various embodiments of the invention herein provide a pharmaceutical composition comprising a compound of formula (I) or a pharmaceutically acceptable salt thereof, as described herein, in association with a pharmaceutically acceptable adjuvant, diluent or carrier, and optionally one or more other therapeutic agents. Various embodiments of the invention herein provide a compound of formula (I) or a pharmaceutically acceptable salt thereof, as described herein, for use in therapy. Various embodiments of the invention herein provide a compound of formula (I) or a pharmaceutically acceptable salt thereof, as described herein for use in treating alcohol, drug or nicotine addiction. Various embodiments of the invention herein provide a compound of formula (I) or a pharmaceutically acceptable salt thereof, as described herein, for use in treating hearing loss or tinnitus. Various embodiments of the invention herein provide a compound of formula (I) or a pharmaceutically acceptable salt thereof, as claimed in any one of claims 1 to 9, for use in treating schizophrenia.

Various embodiments of the invention herein provide a compound comprising the formula (2S)-2-(4-fluorophenyl)-N-((trans)-4-methanesulfonyl-3,4-dihydro-2H-1-benzopyran-3-yl)propanamide or a pharmaceutically acceptable salt thereof for use as a medicament for treatment of a disease, disorder, or condition associated with glutamatergic and GABAergic signalling pathways regulated in full or in part by metabotropic glutamate receptor 7 (mGluR7).

In some embodiments, the compound is a selective agonist of mGluR7. In some embodiments, the compound has an EC$_{50}$ within at least one range selected from the group of ranges consisting of about 1 nM to about 3 nM, about 2 nM to about 4 nM, about 3 nM to about 5 nM, about 4 nM to about 6 nM, and about 6 nM to about 8 nM. In some embodiments, the compound has an $EC_{50}$ of 1.8+3.5 nM. In some embodiments, the compound has an $EC_{50}$ of 6.9+0.8 nM. In some embodiments, the compound is an allosteric agonist of mGluR7. In some embodiments, the compound is more selective for mGluR7 than for mGluR4 or mGluR8.

Various embodiments of the invention herein provide a method of treating a subject for a disease, disorder, or condition associated with glutamatergic and GABAergic signalling pathways regulated in full or in part by metabotropic glutamate receptor 7 (mGluR7) in a subject, the method comprising: administering to the subject a therapeutically effective amount of compound (2S)-2-(4-fluorophenyl)-N-((trans)-4-methanesulfonyl-3,4-dihydro-2H-1-benzopyran-3-yl)propanamide or a pharmaceutically acceptable salt thereof, thereby selectively agonizing mGluR7 to treat the disease, disorder, or condition.

In some embodiments, the method further comprises modulating by the compound neurotransmitter release in the subject to treat the disease, disorder, or condition. In some embodiments of the method, the neurotransmitter is glutamate. In some embodiments of the method, the disease, disorder, or condition is selected from the group consisting of: Parkinson's disease; dementia associated with Parkinson's disease; Alzheimer's disease; Huntington's Chorea; amyotrophic lateral sclerosis; multiple sclerosis; bipolar disorder; schizophrenia; post-traumatic stress disorder; anxiety disorders; depression; alcohol addiction; drug addiction; nicotine addiction; hearing loss; tinnitus; idiopathic autism; severe neonatal encephalopathy; autism spectrum disorder (ASD); X-linked intellectual; epilepsy; cerebral ischemias; eye disorders; Rett syndrome; and pain. In some embodiments of the method, the compound has a concentration selected from the ranges in the group consisting of: about 0.001 μM to about 0.01 μM, about 0.01 μM to about 0.1 μM, about 0.1 μM to about 1.0 μM, and about 1.0 μM to about 10 μM. In some embodiments of the method, the compound has a concentration greater than about 0.001 μM. In some embodiments of the method, the compound has a concentration selected from the group consisting of about 1 μM, about 5 μM, and about 10 μM.

Various embodiments of the invention herein provide a pharmaceutical composition comprising the compound (2S)-2-(4-fluorophenyl)-N-((trans)-4-methanesulfonyl-3,4-dihydro-2H-1-benzopyran-3-yl)propanamide and a pharmaceutically acceptable excipient. Various embodiments of the invention herein provide a compound comprising the formula (2S)-2-(4-fluorophenyl)-N-((trans)-4-methanesulfonyl-3,4-dihydro-2H-1-benzopyran-3-yl)propanamide or a pharmaceutically acceptable salt, an enantiomer, a diastereoisomer, or a mixture of at least one enantiomer and at least one diastereoisomer thereof.

BRIEF DESCRIPTION OF THE DRAWINGS

FIG. 1B is a graph of the results of an impedance assay comparing the effects of pre-treatment with either the compound from Example 16 (CPD1) or AMN082 on the sample's response to tool compound, CPD A, a tool compound, which is a mGluR7 activator. AMN082 (N,N'-dibenzhydrylethane-1,2-diamine dihydrochloride) is a known selective mGluR7 allosteric agonist.

FIGS. 2A-2D are graphs of the results from in vitro cAMP assays in CHO-CRE-luc cells stably expressing human mGluR7 to determine the mode of action of CPD1. FIG. 2A provides the compound activity of non-selective agonist, L-AP4, with increasing concentrations of orthosteric antagonist, LY341495 (LY). FIG. 2B provides the compound activity of a positive allosteric modulator (PAM) compound, VU0422288, for the same concentrations of LY as shown in FIG. 2A. FIG. 2C provides the compound activity of allosteric agonist, AMN082, for the same concentrations of LY as shown in FIG. 2A. FIG. 2D provides the compound activity of CPD 1 for the same concentrations of LY as shown in FIG. 2A.

FIG. 3B is a graph showing the results of a glutamate release potentiation assay. FIG. 3C and FIG. 3D provide graphs of electrophysiological recordings from the SC-CA1 pathway in mouse hippocampal slices. FIG. 3C is a graph comparing the changes in intracellular recordings of excitatory postsynaptic currents (EPSCs) as a result of contact with L-AP4 at a concentration of 0.5 mM, CPD 1 at a concentration of 1 μM, and CPD 1 at a concentration of 5 μM. FIG. 3D is a graph comparing the changes in intracellular recordings of EPSCs in mice with wild-type (WT) mGluR7 and mice with an mGluR7 knock-out contacted with CPD 1 at a concentration of 5 μM.

DETAILED DESCRIPTION OF THE INVENTION

I. Introduction

Figure 1A:
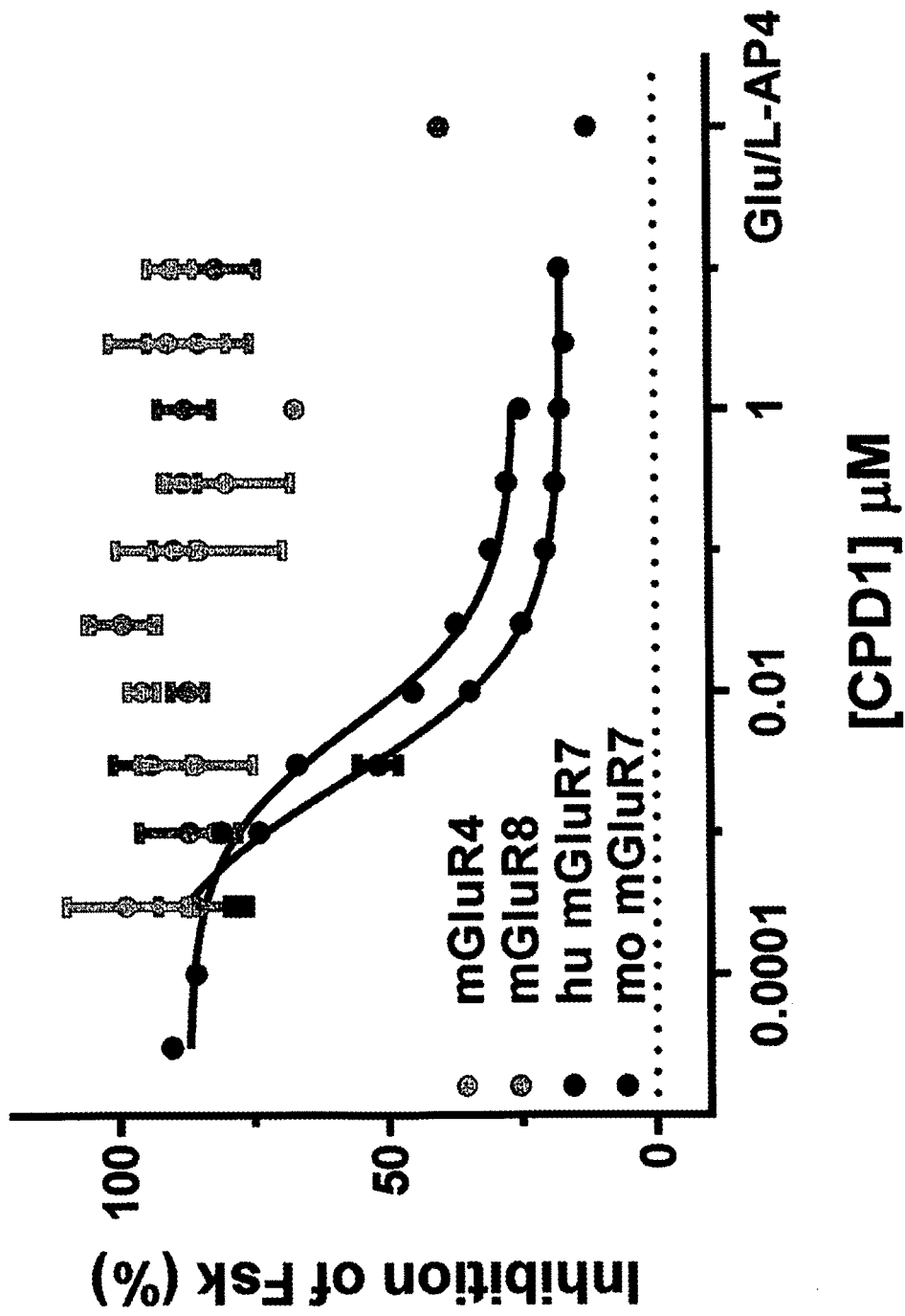
FIG. 1A is a graph of the results of a mGluR7 selectivity assay comparing activation of mGluR4, mGluR8, human mGluR7 (hu mGluR7), and mouse mGluR7 (mo mGluR7) by the compound from Example 16 (CPD1) (data are mean±standard deviation, n=2).

A lack of selective compounds has limited investigation of the therapeutic potential of mGluR7 (14). As identified from a high-throughput screen, agonists, as exemplified by the compound in Example 16 (CPD 1), were tested in a range of assays (recombinant and native) to define their pharmacological profile.

In various embodiments of the present invention, there is provided a compound of formula (I) or a pharmaceutically acceptable salt thereof

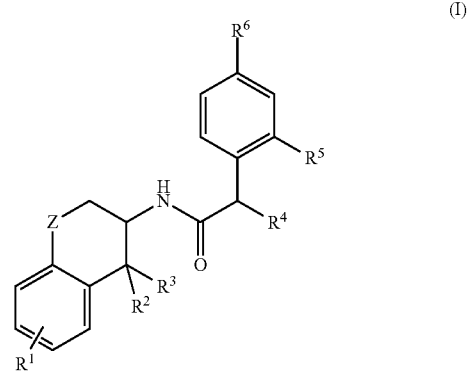

(I)

wherein $R^1$ represents hydrogen or halogen;

$R^2$ represents hydrogen, hydroxyl, $C_1$-$C_6$ alkyl, $C_1$-$C_6$ haloalkyl, $C_1$-$C_6$ alkoxy, $C_1$-$C_6$ haloalkoxy, —N($R^7$)$_2$ or —SO$_2$R$^8$;

R$^3$ represents hydrogen or C$_1$-C$_3$ alkyl;

or R$^2$ and R$^3$ together form =O;

R$^4$ represents cyano, hydroxyl, —N(R$^9$)$_2$, C$_1$-C$_6$ alkyl, C$_3$-C$_6$ cycloalkyl, C$_1$-C$_6$ alkoxy, C$_3$-C$_6$ cycloalkoxy, C$_1$-C$_6$ alkylcarbonyl, C$_3$-C$_6$ cycloalkylcarbonyl, C$_1$-C$_6$ alkoxycarbonyl, C$_3$-C$_6$ cycloalkoxycarbonyl, —(CH$_2$)$_m$R$^{10}$, —O(CH$_2$)$_m$R$^{10}$ or —NH(CH$_2$)$_m$R$^{10}$, wherein each of the alkyl, cycloalkyl, alkoxy, cycloalkoxy, alkylcarbonyl, cycloalkylcarbonyl, alkoxycarbonyl and cycloalkoxycarbonyl moieties is independently unsubstituted or substituted with at least one substituent independently selected from halogen, cyano, hydroxyl, oxo, methylamino, dimethylamino, C$_1$-C$_3$ alkyl, C$_1$-C$_3$ haloalkyl, C$_1$-C$_3$ alkoxy and C$_1$-C$_3$ haloalkoxy;

R$^5$ represents hydrogen or halogen;

or R$^4$ and R$^5$ together with the benzyl group to which they are attached form a 5- to 7-membered carbocyclic or heterocyclic ring, the heterocyclic ring comprising at least one ring heteroatom independently selected from nitrogen, oxygen and sulphur atoms, wherein the carbocyclic or heterocyclic ring is unsubstituted or substituted with at least one substituent independently selected from halogen, cyano, hydroxyl, oxo, amino, methylamino, dimethylamino, C$_1$-C$_6$ alkyl, C$_1$-C$_6$ haloalkyl, C$_1$-C$_6$ alkoxy, C$_1$-C$_6$ haloalkoxy, —(CH$_2$)$_n$R$^{11}$ and —O(CH$_2$)$_n$R$^{11}$;

R$^6$ represents hydrogen, halogen, C$_1$-C$_6$ alkyl or C$_1$-C$_6$ haloalkyl;

R$^7$ independently represents hydrogen, C$_1$-C$_6$ alkyl, C$_1$-C$_6$ haloalkyl, C$_4$-C$_6$ cycloalkyl, (C$_3$-C$_6$ cycloalkyl)methyl, 4- to 6-membered heterocycloalkyl, (3- to 6-membered heterocycloalkyl)methyl or —COR$^{12}$, or two R$^7$ together with the nitrogen atom to which they are attached form a saturated or unsaturated 4- to 7-membered heterocyclic ring optionally comprising one or more further ring heteroatoms independently selected from nitrogen, oxygen and sulphur atoms, the heterocyclic ring being unsubstituted or substituted with at least one substituent independently selected from halogen, cyano, hydroxyl, oxo, amino, methylamino, dimethylamino, C$_1$-C$_3$ alkyl, C$_1$-C$_3$ haloalkyl, C$_1$-C$_3$ alkoxy and C$_1$-C$_3$ haloalkoxy;

R$^8$ represents C$_1$-C$_3$ alkyl, C$_3$-C$_6$ cycloalkyl or (C$_3$-C$_6$ cycloalkyl)methyl;

R$^9$ independently represents methyl, C$_3$-C$_6$ alkyl or C$_1$-C$_6$ haloalkyl, or two R$^9$ together with the nitrogen atom to which they are attached form a saturated or unsaturated 4- to 7-membered heterocyclic ring optionally comprising one or more further ring heteroatoms independently selected from nitrogen, oxygen and sulphur atoms, the heterocyclic ring being unsubstituted or substituted with at least one substituent independently selected from halogen, cyano, hydroxyl, oxo, amino, methylamino, dimethylamino, C$_1$-C$_3$ alkyl, C$_1$-C$_3$ haloalkyl, C$_1$-C$_3$ alkoxy and C$_1$-C$_3$ haloalkoxy;

R$^{10}$ represents a saturated or unsaturated 3- to 7-membered carbocyclic ring or a saturated or unsaturated 4- to 7-membered heterocyclic ring, the heterocyclic ring comprising at least one ring heteroatom independently selected from nitrogen, oxygen and sulphur atoms, wherein the carbocyclic or heterocyclic ring is unsubstituted or substituted with at least one substituent independently selected from halogen, cyano, hydroxyl, oxo, amino, methylamino, dimethylamino, C$_1$-C$_3$ alkyl, C$_1$-C$_3$ haloalkyl, C$_1$-C$_3$ alkoxy and C$_1$-C$_3$ haloalkoxy;

R$^{11}$ represents a saturated or unsaturated 3- to 7-membered carbocyclic ring or a saturated or unsaturated 4- to 7-membered heterocyclic ring, the heterocyclic ring comprising at least one ring heteroatom independently selected from nitrogen, oxygen and sulphur atoms, wherein the carbocyclic or heterocyclic ring is unsubstituted or substituted with at least one substituent independently selected from halogen, cyano, hydroxyl, oxo, amino, methylamino, dimethylamino, C$_1$-C$_3$ alkyl, C$_1$-C$_3$ haloalkyl, C$_1$-C$_3$ alkoxy and C$_1$-C$_3$ haloalkoxy;

R$^{12}$ represents a saturated or unsaturated 3- to 7-membered carbocyclic ring or a saturated or unsaturated 4- to 7-membered heterocyclic ring, the heterocyclic ring comprising at least one ring heteroatom independently selected from nitrogen, oxygen and sulphur atoms, wherein the carbocyclic or heterocyclic ring is unsubstituted or substituted with at least one substituent independently selected from halogen, cyano, hydroxyl, oxo, amino, methylamino, dimethylamino, C$_1$-C$_3$ alkyl, C$_1$-C$_3$ haloalkyl, C$_1$-C$_3$ alkoxy, C$_1$-C$_3$ haloalkoxy and —CON(R$^{13}$)$_2$;

R$^{13}$ independently represents hydrogen or C$_1$-C$_3$ alkyl;

Z represents —CH$_2$— or —O—;

m is 0, 1, 2 or 3; and n is 0, 1, 2 or 3.

In the context of the present specification, unless otherwise stated, an "alkyl" substituent group or an "alkyl" moiety in a substituent group (such as an alkoxy group) may be linear or branched. Examples of C$_1$-C$_6$ alkyl groups/moieties include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, tert-butyl, n-pentyl, and n-hexyl.

A "cycloalkyl" substituent group or a "cycloalkyl" moiety in a substituent group refers to a saturated hydrocarbyl ring containing, for example, from 3 to 8 ring carbon atoms, examples of which include cyclopropyl, cyclobutyl, cyclopentyl and cyclohexyl.

A "heterocycloalkyl" substituent group or a "heterocycloalkyl" moiety in a substituent group refers to a saturated hydrocarbyl ring containing, for example, from 3 to 8 ring carbon atoms, in which one or more (e.g. one, two, three, four, five or six) ring carbon atoms are replaced by a corresponding number of ring heteroatoms independently selected from nitrogen, oxygen and sulphur, particularly nitrogen and oxygen. A "3- to 6-membered heterocycloalkyl" substituent group or moiety has three, four, five or six ring atoms, at least one (e.g. one, two, three, four or five) of which is a ring carbon atom and at least one (e.g. one, two, three, four or five) of which is a ring heteroatom independently selected from nitrogen, oxygen and sulphur, particularly nitrogen and oxygen. Similarly, a "4- to 6-membered heterocycloalkyl" substituent group or moiety has four, five or six ring atoms, at least one (e.g. one, two, three, four or five) of which is a ring carbon atom and at least one (e.g. one, two, three, four or five) of which is a ring heteroatom independently selected from nitrogen, oxygen and sulphur, particularly nitrogen and oxygen. Examples of heterocycloalkyl substituent groups or moieties include tetrahydrofuranyl (oxolanyl), piperidinyl, azetidinyl, piperazinyl, pyrrolidinyl, tetrahydropyranyl (oxanyl), oxazolidinyl, oxetanyl, pyrazolidinyl, imidazolidinyl, thiazolidinyl, dioxolanyl, 1,4-dioxanyl, azepanyl, morpholinyl, and thiomorpholinyl.

The term "halogen" includes fluorine, chlorine, bromine and iodine.

A "haloalkyl" or "haloalkoxy" substituent group/moiety comprises at least one halogen atom, e.g. one, two, three, four or five halogen atoms. Examples of such groups/moieties include fluoromethyl, difluoromethyl, trifluoromethyl, 2,2,2-trifluoroethyl, pentafluoroethyl, fluoromethoxy, difluoromethoxy, trifluoromethoxy, 2,2,2-trifluoroethoxy, and pentafluoroethoxy.

The term "amino" refers to a —NH$_2$ substituent group. Similarly, the term "methylamino" refers to a —NH(CH$_3$) substituent group and the term "dimethylamino" refers to a —N(CH$_3$)$_2$ substituent group.

The term "oxo" refers to an oxygen atom doubly bonded to the carbon atom to which it is attached to form the carbonyl of a ketone or aldehyde.

A "saturated or unsaturated 4- to 7-membered heterocyclic ring" means a saturated, partially unsaturated or fully unsaturated hydrocarbyl group containing four, five, six or seven ring atoms in which one or more (e.g. one, two, three, four, five or six) ring carbon atoms are replaced by a corresponding number of ring heteroatoms independently selected from nitrogen, oxygen and sulphur, particularly nitrogen and oxygen. Examples of such heterocyclic rings include tetrahydrofuranyl (oxolanyl), piperidinyl, azetidinyl, piperazinyl, pyrrolidinyl, tetrahydropyranyl (oxanyl), oxazolidinyl, oxetanyl, pyrazolidinyl, imidazolidinyl, thiazolidinyl, dioxolanyl, 1,4-dioxanyl, azepanyl, morpholinyl, thiomorpholinyl, pyrrolyl, imidazolyl, pyrazolyl, triazolyl, tetrazolyl, pyridinyl, pyrazinyl, pyrimidinyl, pyridazinyl, triazinyl, thienyl, furyl, furazanyl, oxazolyl, thiazolyl, oxadiazolyl, isothiazolyl, isoxazolyl, thiadiazolyl, and tetrazinyl. When a heterocyclic ring is substituted, it should be understood that the substituent(s) may be attached to any suitable ring atom.

A "saturated or unsaturated 3- to 7-membered carbocyclic ring" means a saturated, partially unsaturated or fully unsaturated hydrocarbyl group containing three, four, five, six or seven ring carbon atoms. Examples of such carbocyclic rings include cyclopropyl, cyclobutyl, cyclopentyl, cyclohexyl, cycloheptyl, cyclopropenyl, cyclobutenyl, cyclopentenyl, cyclohexenyl, cycloheptenyl, cyclopentadienyl, cyclohexadienyl, phenyl, cycloheptadienyl, and cycloheptatrienyl.

When $R^4$ and $R^5$ together with the benzyl group to which they are attached form a 5- to 7-membered carbocyclic or heterocyclic ring, the 5- to 7-membered carbocyclic or heterocyclic ring comprises at least one double bond and may optionally comprise one or two further double bonds, so that the ring may be partially unsaturated or fully unsaturated. A "5- to 7-membered carbocyclic or heterocyclic ring" means a hydrocarbyl group containing five, six or seven ring atoms in which one or more (e.g. one, two, three, four, five or six) ring carbon atoms are optionally replaced by a corresponding number of ring heteroatoms independently selected from nitrogen, oxygen and sulphur, particularly nitrogen and oxygen.

For the purposes of the present invention, where a combination of moieties is referred to as one group, for example, alkylcarbonyl, cycloalkylcarbonyl, alkoxycarbonyl, cycloalkoxycarbonyl, methylamino, dimethylamino, haloalkyl, haloalkoxy, ($C_3$-$C_6$ cycloalkyl)methyl or (3- to 6-membered heterocycloalkyl)methyl, the last mentioned moiety contains the atom by which the group is attached to the rest of the molecule.

When any chemical group or moiety in formula (I) is described as substituted, it will be appreciated that the number and nature of substituents will be selected so as to avoid sterically undesirable combinations.

Further, it will be appreciated that the invention does not encompass any unstable ring or other structures (e.g. >NCH$_2$N<, >NCH$_2$O— or aminal groupings of the type >C(NR$_a$R$_b$)(NR$_c$R$_d$)) or any O—O or S—S bonds.

$R^1$ represents hydrogen or halogen. In a preferred embodiment of the invention, $R^1$ represents hydrogen, fluorine, chlorine or bromine. In another preferred embodiment, $R^1$ represents hydrogen, fluorine or chlorine. In another preferred embodiment, $R^1$ represents hydrogen or fluorine.

$R^2$ may represent hydrogen, hydroxyl, $C_1$-$C_6$ alkyl, $C_1$-$C_6$ haloalkyl, $C_1$-$C_6$ alkoxy, $C_1$-$C_6$ haloalkoxy, —N($R^7$)$_2$ or —SO$_2$R$^8$; wherein $R^7$ independently represents hydrogen, $C_1$-$C_6$ alkyl, $C_1$-$C_6$ haloalkyl, $C_4$-$C_6$ cycloalkyl, ($C_3$-$C_6$ cycloalkyl)methyl, 4- to 6-membered heterocycloalkyl, (3- to 6-membered heterocycloalkyl)methyl or —COR$^{12}$, or two $R^7$ together with the nitrogen atom to which they are attached form a saturated or unsaturated 4- to 7-membered heterocyclic ring optionally comprising one or more further ring heteroatoms (e.g. one, two, three, four or five further ring heteroatoms) independently selected from nitrogen, oxygen and sulphur atoms (in particular nitrogen and oxygen atoms), the heterocyclic ring being unsubstituted or substituted with at least one substituent (e.g. one, two, three, four, five, six or seven substituents) independently selected from halogen, cyano, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy;

$R^8$ represents $C_1$-$C_3$ alkyl, $C_3$-$C_6$ cycloalkyl or ($C_3$-$C_6$ cycloalkyl)methyl;

$R^{12}$ represents a saturated or unsaturated 3- to 7-membered carbocyclic ring or a saturated or unsaturated 4- to 7-membered heterocyclic ring, the heterocyclic ring comprising at least one ring heteroatom (e.g. one, two, three, four, five or six ring heteroatoms) independently selected from nitrogen, oxygen and sulphur atoms (in particular nitrogen and oxygen atoms), wherein the carbocyclic or heterocyclic ring is unsubstituted or substituted with at least one substituent (e.g. one, two, three, four, five, six or seven substituents) independently selected from halogen, cyano, hydroxyl, oxo, amino, methylamino, dimethylamino, $C_1$-$C_3$ alkyl, $C_1$-$C_3$ haloalkyl, $C_1$-$C_3$ alkoxy, $C_1$-$C_3$ haloalkoxy and —CON($R^{13}$)$_2$; and $R^{13}$ independently represents hydrogen or $C_1$-$C_3$ alkyl.

In a preferred embodiment of the invention, $R^2$ represents hydrogen, hydroxyl, $C_1$-$C_6$ alkyl, $C_1$-$C_6$ haloalkyl, $C_1$-$C_6$ alkoxy, $C_1$-$C_6$ haloalkoxy, —N($R^7$)$_2$ or —SO$_2$R$^8$; wherein $R^7$ independently represents hydrogen, $C_1$-$C_6$ alkyl, $C_1$-$C_6$ haloalkyl or —COR$^{12}$, or two $R^7$ together with the nitrogen atom to which they are attached form a saturated or unsaturated 4- to 7-membered heterocyclic ring optionally comprising one or more further ring heteroatoms (e.g. one, two, three, four or five further ring heteroatoms) independently selected from nitrogen, oxygen and sulphur atoms (in particular nitrogen and oxygen atoms), the heterocyclic ring being unsubstituted or substituted with at least one substituent (e.g. one, two, three, four, five, six or seven substituents) independently selected from halogen, cyano, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy;

$R^8$ represents $C_1$-$C_3$ alkyl;

$R^{12}$ represents a saturated or unsaturated 3- to 7-membered carbocyclic ring or a saturated or unsaturated 4- to 7-membered heterocyclic ring, the heterocyclic ring comprising at least one ring heteroatom (e.g. one, two, three, four, five or six ring heteroatoms) independently selected from nitrogen, oxygen and sulphur atoms (in particular nitrogen and oxygen atoms), wherein the carbocyclic or heterocyclic ring is unsubstituted or substituted with at least one substituent (e.g. one, two, three, four, five, six or seven substituents) independently selected from halogen, cyano, hydroxyl, oxo, amino, methylamino, dimethylamino, $C_1$-$C_3$ alkyl, $C_1$-$C_3$ haloalkyl, $C_1$-$C_3$ alkoxy, $C_1$-$C_3$ haloalkoxy and —CON($R^{13}$)$_2$; and $R^{13}$ independently represents hydrogen or $C_1$-$C_3$ alkyl.

In another preferred embodiment, $R^2$ represents hydrogen, hydroxyl, $C_1$-$C_3$ alkyl, $C_1$-$C_3$ haloalkyl, $C_1$-$C_3$ alkoxy, $C_1$-$C_3$ haloalkoxy, —N($R^7$)$_2$ or —SO$_2$R$^8$; wherein $R^7$ independently represents hydrogen, $C_1$-$C_3$ alkyl, $C_1$-$C_3$ haloalkyl or COR$^{12}$, or two $R^7$ together with the nitrogen atom to which they are attached form a saturated or unsaturated 4-, 5- or 6-membered heterocyclic ring optionally comprising one, two or three further ring heteroatoms independently selected from nitrogen and oxygen atoms, the heterocyclic ring being unsubstituted or substituted with one, two, three or four substituents independently selected from halogen, hydroxyl, amino, methylamino, dimethylamino, $C_1$-$C_3$ alkyl, $C_1$-$C_3$ haloalkyl, $C_1$-$C_3$ alkoxy and $C_1$-$C_3$ haloalkoxy;

$R^8$ represents $C_1$-$C_3$ alkyl;

$R^{12}$ represents a saturated or unsaturated 5- or 6-membered carbocyclic ring or a saturated or unsaturated 5- or 6-membered heterocyclic ring, the heterocyclic ring comprising one, two or three ring heteroatoms independently selected from nitrogen and oxygen atoms, wherein the carbocyclic or heterocyclic ring is unsubstituted or substituted with one, two or three substituents independently selected from halogen, hydroxyl, amino, methylamino, dimethylamino, $C_1$-$C_3$ alkyl, $C_1$-$C_3$ haloalkyl, $C_1$-$C_3$ alkoxy, $C_1$-$C_3$ haloalkoxy and —CON($R^{13}$)$_2$; and $R^{13}$ independently represents hydrogen or $C_1$-$C_3$ alkyl.

In another preferred embodiment, $R^2$ represents hydrogen, hydroxyl, $C_1$-$C_3$ alkoxy, $C_1$-$C_3$ haloalkoxy, —N($R^7$)$_2$ or —SO$_2$R$^8$; wherein $R^7$ independently represents hydrogen, $C_1$-$C_3$ alkyl or —COR$^{12}$, or two $R^7$ together with the nitrogen atom to which they are attached form a 4-, 5- or 6-membered heterocyclic ring optionally comprising one or two further ring heteroatoms independently selected from nitrogen and oxygen atoms, the heterocyclic ring being unsubstituted or substituted with one, two or three substituents independently selected from halogen, hydroxyl, amino, methylamino, dimethylamino, $C_1$-$C_3$ alkyl, $C_1$-$C_3$ haloalkyl, $C_1$-$C_3$ alkoxy and $C_1$-$C_3$ haloalkoxy;

$R^8$ represents $C_1$-$C_3$ alkyl;

$R^{12}$ represents phenyl which is unsubstituted or substituted with one or two substituents independently selected from halogen, hydroxyl, amino, methylamino, dimethylamino, $C_1$-$C_3$ alkyl, $C_1$-$C_3$ haloalkyl, $C_1$-$C_3$ alkoxy, $C_1$-$C_3$ haloalkoxy and —CON($R^{13}$)$_2$; and $R^{13}$ independently represents hydrogen or $C_1$-$C_3$ alkyl.

In another preferred embodiment of the invention, $R^2$ represents hydrogen, hydroxyl, $C_1$-$C_3$ alkyl, $C_1$-$C_3$ haloalkyl, $C_1$-$C_3$ alkoxy, $C_1$-$C_3$ haloalkoxy, —N($R^7$)$_2$ or —SO$_2$R$^8$. In another preferred embodiment, $R^2$ represents hydrogen, hydroxyl, $C_1$-$C_3$ alkoxy, $C_1$-$C_3$ haloalkoxy, —N($R^7$)$_2$ or —SO$_2$R$^8$. In another preferred embodiment, $R^2$ represents hydrogen, hydroxyl, $C_1$-$C_3$ alkoxy, —N($R^7$)$_2$ or —SO$_2$R$^8$.

In another preferred embodiment of the invention, $R^7$ represents hydrogen, $C_1$-$C_6$ alkyl, $C_1$-$C_6$ haloalkyl or —COR$^{12}$, or two $R^7$ together with the nitrogen atom to which they are attached form a saturated or unsaturated 4- to 7-membered heterocyclic ring optionally comprising one or more further ring heteroatoms (e.g. one, two, three, four or five further ring heteroatoms) independently selected from nitrogen, oxygen and sulphur atoms (in particular nitrogen and oxygen atoms), the heterocyclic ring being unsubstituted or substituted with at least one substituent (e.g. one, two, three, four, five, six or seven substituents) independently selected from halogen, cyano, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy.

In another preferred embodiment, $R^7$ represents hydrogen, $C_1$-$C_3$ alkyl, $C_1$-$C_3$ haloalkyl or —COR$^{12}$, or two $R^7$ together with the nitrogen atom to which they are attached form a saturated or unsaturated 4-, 5- or 6-membered heterocyclic ring optionally comprising one, two or three further ring heteroatoms independently selected from nitrogen and oxygen atoms, the heterocyclic ring being unsubstituted or substituted with one, two, three or four substituents independently selected from halogen, hydroxyl, amino, methylamino, dimethylamino, $C_1$-$C_3$ alkyl, $C_1$-$C_3$ haloalkyl, $C_1$-$C_3$ alkoxy and $C_1$-$C_3$ haloalkoxy.

In another preferred embodiment, $R^7$ represents hydrogen, $C_1$-$C_3$ alkyl or —COR$^{12}$, or two $R^7$ together with the nitrogen atom to which they are attached form a saturated 4-, 5- or 6-membered heterocyclic ring optionally comprising one or two further ring heteroatoms independently selected from nitrogen and oxygen atoms, the heterocyclic ring being unsubstituted or substituted with one, two or three substituents independently selected from halogen, hydroxyl, amino, methylamino, dimethylamino, $C_1$-$C_3$ alkyl, $C_1$-$C_3$ haloalkyl, $C_1$-$C_3$ alkoxy and $C_1$-$C_3$ haloalkoxy.

In another preferred embodiment, $R^7$ represents hydrogen, $C_1$-$C_2$ alkyl or —COR$^{12}$, or two $R^7$ together with the nitrogen atom to which they are attached form a saturated 4-, 5- or 6-membered heterocyclic ring optionally comprising one or two further ring heteroatoms independently selected from nitrogen and oxygen atoms, the heterocyclic ring being unsubstituted or substituted with one or two substituents independently selected from halogen, hydroxyl, $C_1$-$C_3$ alkyl, $C_1$-$C_3$ haloalkyl, $C_1$-$C_3$ alkoxy and $C_1$-$C_3$ haloalkoxy.

In one embodiment, two $R^7$ together with the nitrogen atom to which they are attached form an optionally substituted azetidine

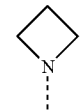

wherein - - - represents the bond by which the azetidine is attached to the rest of the molecule.

In another embodiment, two $R^7$ together with the nitrogen atom to which they are attached form an optionally substituted saturated or unsaturated 5-membered heterocyclic ring selected from:

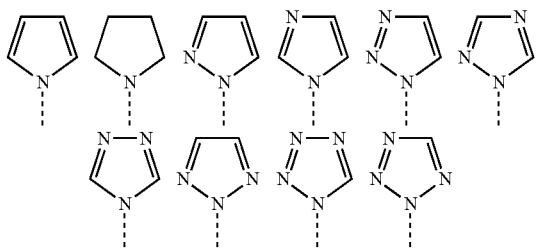

wherein - - - represents the bond by which the heterocyclic ring is attached to the rest of the molecule.

In another embodiment, two $R^7$ together with the nitrogen atom to which they are attached form an optionally substituted saturated or unsaturated 6-membered heterocyclic ring selected from:

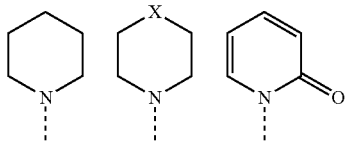

wherein X is —NH—, —O— or —S—, preferably —NH— or —O—, and wherein represents the bond by which the heterocyclic ring is attached to the rest of the molecule.

In another preferred embodiment of the invention, $R^8$ represents $C_1$-$C_3$ alkyl. In another preferred embodiment, $R^8$ represents methyl or ethyl. In another preferred embodiment, $R^8$ represents methyl.

In another preferred embodiment of the invention, $R^{12}$ represents a saturated or unsaturated 5- or 6-membered carbocyclic ring or a saturated or unsaturated 5- or 6-membered heterocyclic ring, the heterocyclic ring comprising one, two or three ring heteroatoms independently selected from nitrogen and oxygen atoms, wherein the carbocyclic or heterocyclic ring is unsubstituted or substituted with one, two or three substituents independently selected from halogen, hydroxyl, amino, methylamino, dimethylamino, $C_1$-$C_3$ alkyl, $C_1$-$C_3$ haloalkyl, $C_1$-$C_3$ alkoxy, $C_1$-$C_3$ haloalkoxy and —CON($R^{13}$)$_2$.

In another preferred embodiment, $R^{12}$ represents phenyl which is unsubstituted or substituted with one or two substituents independently selected from halogen, hydroxyl, amino, methylamino, dimethylamino, $C_1$-$C_3$ alkyl, $C_1$-$C_3$ haloalkyl, $C_1$-$C_3$ alkoxy, $C_1$-$C_3$ haloalkoxy and —CON($R^{13}$)$_2$.

In another preferred embodiment, $R^{12}$ represents phenyl substituted with one or two substituents independently selected from halogen, hydroxyl, $C_1$-$C_3$ alkyl, $C_1$-$C_3$ haloalkyl, $C_1$-$C_3$ alkoxy, $C_1$-$C_3$ haloalkoxy and —CON($R^{13}$)$_2$.

In one embodiment, $R^{12}$ represents an optionally substituted saturated or unsaturated 5-membered heterocyclic ring selected from:

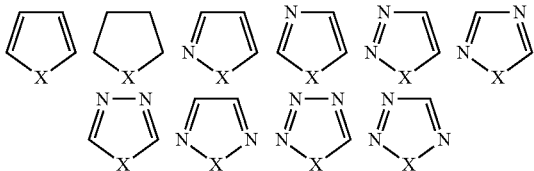

wherein X is —NH—, —O— or —S—, preferably —NH— or —O—, preferably —O—, and wherein any suitable heterocyclic ring atom is attached to the rest of the molecule.

In another embodiment, $R^{12}$ represents an optionally substituted saturated or unsaturated 6-membered heterocyclic ring selected from:

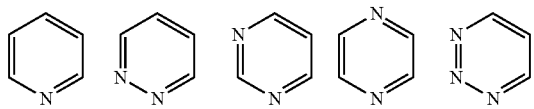

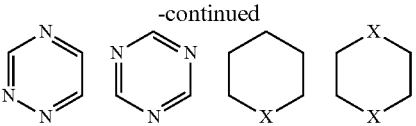

wherein X is —NH—, —O— or —S—, preferably —NH— or —O—, and wherein any suitable heterocyclic ring atom is attached to the rest of the molecule.

In another preferred embodiment of the invention, $R^{13}$ independently represents hydrogen, methyl or ethyl. In another preferred embodiment, $R^{13}$ independently represents hydrogen or methyl.

$R^3$ may represent hydrogen or $C_1$-$C_3$ alkyl. In a preferred embodiment of the invention, $R^3$ represents hydrogen, methyl or ethyl. In another embodiment, $R^3$ represents hydrogen or methyl.

In one embodiment of the invention, $R^2$ and $R^3$ together form =O.

$R^4$ may represent cyano, hydroxyl, —N($R^9$)$_2$, $C_1$-$C_6$ alkyl, $C_3$-$C_6$ cycloalkyl, $C_1$-$C_6$ alkoxy, $C_3$-$C_6$ cycloalkoxy, $C_1$-$C_6$ alkylcarbonyl, $C_3$-$C_6$ cycloalkylcarbonyl, $C_1$-$C_6$ alkoxycarbonyl, $C_3$-$C_6$ cycloalkoxycarbonyl, —(CH$_2$)$_m$R$^{10}$, —O(CH$_2$)$_m$R$^{10}$ or —NH(CH$_2$)$_m$R$^{10}$, wherein each of the alkyl, cycloalkyl, alkoxy, cycloalkoxy, alkylcarbonyl, cycloalkylcarbonyl, alkoxycarbonyl and cycloalkoxycarbonyl moieties is independently unsubstituted or substituted with at least one substituent (e.g. one, two, three, four, five, six or seven substituents) independently selected from halogen, cyano, hydroxyl, oxo, methylamino, dimethylamino, $C_1$-$C_3$ alkyl, $C_1$-$C_3$ haloalkyl, $C_1$-$C_3$ alkoxy and $C_1$-$C_3$ haloalkoxy; wherein $R^9$ independently represents methyl, $C_3$-$C_6$ alkyl or $C_1$-$C_6$ haloalkyl, or two $R^9$ together with the nitrogen atom to which they are attached form a saturated or unsaturated 4- to 7-membered heterocyclic ring optionally comprising one or more further ring heteroatoms (e.g. one, two, three, four or five further ring heteroatoms) independently selected from nitrogen, oxygen and sulphur atoms (in particular nitrogen and oxygen atoms), the heterocyclic ring being unsubstituted or substituted with at least one substituent (e.g. one, two, three, four, five, six or seven substituents) independently selected from halogen, cyano, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy;

$R^{10}$ represents a saturated or unsaturated 3- to 7-membered carbocyclic ring or a saturated or unsaturated 4- to 7-membered heterocyclic ring, the heterocyclic ring comprising at least one ring heteroatom (e.g. one, two, three, four, five or six ring heteroatoms) independently selected from nitrogen, oxygen and sulphur atoms (in particular nitrogen and oxygen atoms), wherein the carbocyclic or heterocyclic ring is unsubstituted or substituted with at least one substituent (e.g. one, two, three, four, five, six or seven substituents) independently selected from halogen, cyano, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy; and m is 0, 1, 2 or 3.

In a preferred embodiment of the invention, $R^4$ represents hydroxyl, —N($R^9$)$_2$, $C_1$-$C_3$ alkyl, $C_3$-$C_6$ cycloalkyl, $C_1$-$C_3$ alkoxy, $C_3$-$C_6$ cycloalkoxy, $C_1$-$C_3$ alkylcarbonyl, $C_3$-$C_6$ cycloalkylcarbonyl, $C_1$-$C_3$ alkoxycarbonyl, $C_3$-$C_6$ cycloalkoxycarbonyl, (CH$_2$)$_m$R$^{10}$, —O(CH$_2$)$_m$R$^{10}$ or —NH(CH$_2$)$_m$R$^{10}$, wherein each of the alkyl, cycloalkyl, alkoxy, cycloalkoxy, alkylcarbonyl, cycloalkylcarbonyl, alkoxycarbonyl and cycloalkoxycarbonyl moieties is independently unsubstituted or substituted with one, two or three substituents independently selected from halogen, hydroxyl, methylamino, dimethylamino, $C_1$-$C_3$ alkyl, $C_1$-$C_3$ haloalkyl, $C_1$-$C_3$ alkoxy and $C_1$-$C_3$ haloalkoxy; wherein $R^9$ independently represents methyl, $C_3$-$C_6$ alkyl or $C_1$-$C_6$ haloalkyl, or two $R^9$ together with the nitrogen atom to which they are attached form a saturated or unsaturated 4-, 5- or 6-membered heterocyclic ring optionally comprising one or two further ring heteroatoms independently selected from nitrogen and oxygen atoms, the heterocyclic ring being unsubstituted or substituted with one, two or three substituents independently selected from halogen, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy;

$R^{10}$ represents a saturated or unsaturated 3-, 4-, 5- or 6-membered carbocyclic ring or a saturated or unsaturated 4-, 5- or 6-membered heterocyclic ring, the heterocyclic ring comprising one, two or three ring heteroatoms independently selected from nitrogen and oxygen atoms, wherein the carbocyclic or heterocyclic ring is unsubstituted or substituted with one, two or three substituents independently selected from halogen, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy; and m is 0, 1 or 2.

In another preferred embodiment, $R^4$ represents hydroxyl, —N($R^9$)$_2$, $C_1$-$C_3$ alkyl, $C_3$-$C_6$ cycloalkyl, $C_1$-$C_3$ alkoxy, $C_3$-$C_6$ cycloalkoxy, —(CH$_2$)$_m$R$^{10}$, —O(CH$_2$)$_m$R$^{10}$ or —NH(CH$_2$)$_m$R$^{10}$, wherein each of the alkyl, cycloalkyl, alkoxy and cycloalkoxy moieties is independently unsubstituted or substituted with one or two substituents independently selected from halogen, hydroxyl, methylamino, dimethylamino, $C_1$-$C_3$ alkyl, $C_1$-$C_3$ haloalkyl, $C_1$-$C_3$ alkoxy and $C_1$-$C_3$ haloalkoxy; wherein $R^9$ independently represents methyl, $C_3$-$C_6$ alkyl or $C_1$-$C_6$ haloalkyl, or two $R^9$ together with the nitrogen atom to which they are attached form a saturated or unsaturated 4-, 5- or 6-membered heterocyclic ring optionally comprising one or two further ring heteroatoms independently selected from nitrogen and oxygen atoms, the heterocyclic ring being unsubstituted or substituted with one or two substituents independently selected from halogen, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy;

$R^{10}$ represents a saturated or unsaturated 3-, 4-, 5- or 6-membered carbocyclic ring or a saturated or unsaturated 4-, 5- or 6-membered heterocyclic ring, the heterocyclic ring comprising one, two or three ring heteroatoms independently selected from nitrogen and oxygen atoms, wherein the carbocyclic or heterocyclic ring is unsubstituted or substituted with one or two substituents independently selected from halogen, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy; and m is 0, 1 or 2.

In another preferred embodiment, $R^4$ represents —N($R^9$)$_2$, $C_1$-$C_3$ alkyl, —(CH$_2$)$_m$R$^{10}$, —O(CH$_2$)$_m$R$^{10}$ or —NH(CH$_2$)$_m$R$^{10}$, wherein the alkyl moiety is unsubstituted or substituted with one or two substituents independently selected from halogen, hydroxyl, methylamino, dimethylamino, $C_1$-$C_3$ alkyl, $C_1$-$C_3$ haloalkyl, $C_1$-$C_3$ alkoxy and $C_1$-$C_3$ haloalkoxy; wherein two $R^9$ together with the nitrogen atom to which they are attached form a saturated or unsaturated 4-, 5- or 6-membered heterocyclic ring optionally comprising one or two further ring heteroatoms independently selected from nitrogen and oxygen atoms, the heterocyclic ring being unsubstituted or substituted with one or two substituents independently selected from halogen, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy;

$R^{10}$ represents a saturated or unsaturated 3-, 4-, 5- or 6-membered carbocyclic ring or a saturated or unsaturated 4-, 5- or 6-membered heterocyclic ring, the heterocyclic ring comprising one, two or three ring heteroatoms independently selected from nitrogen and oxygen atoms, wherein the carbocyclic or heterocyclic ring is unsubstituted or substituted with one or two substituents independently selected from halogen, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy; and m is 0, 1 or 2.

In another preferred embodiment of the invention, $R^4$ represents hydroxyl, —N($R^9$)$_2$, $C_1$-$C_3$ alkyl, $C_3$-$C_6$ cycloalkyl, $C_1$-$C_3$ alkoxy, $C_3$-$C_6$ cycloalkoxy, $C_1$-$C_3$ alkylcarbonyl, $C_3$-$C_6$ cycloalkylcarbonyl, $C_1$-$C_3$ alkoxycarbonyl, $C_3$-$C_6$ cycloalkoxycarbonyl, —(CH$_2$)$_m$R$^{10}$, —O(CH$_2$)$_m$R$^{10}$ or —NH(CH$_2$)$_m$R$^{10}$, wherein each of the alkyl, cycloalkyl, alkoxy, cycloalkoxy, alkylcarbonyl, cycloalkylcarbonyl, alkoxycarbonyl and cycloalkoxycarbonyl moieties is independently unsubstituted or substituted with one, two or three substituents independently selected from halogen, hydroxyl, methylamino, dimethylamino, $C_1$-$C_3$ alkyl, $C_1$-$C_3$ haloalkyl, $C_1$-$C_3$ alkoxy and $C_1$-$C_3$ haloalkoxy.

In another preferred embodiment, $R^4$ represents hydroxyl, —N($R^9$)$_2$, $C_1$-$C_3$ alkyl, $C_3$-$C_6$ cycloalkyl, $C_1$-$C_3$ alkoxy, $C_3$-$C_6$ cycloalkoxy, —(CH$_2$)$_m$R$^{10}$, —O(CH$_2$)$_m$R$^{10}$ or —NH(CH$_2$)$_m$R$^{10}$, wherein each of the alkyl, cycloalkyl, alkoxy and cycloalkoxy moieties is independently unsubstituted or substituted with one or two substituents independently selected from halogen, hydroxyl, methylamino, dimethylamino, $C_1$-$C_3$ alkyl, $C_1$-$C_3$ haloalkyl, $C_1$-$C_3$ alkoxy and $C_1$-$C_3$ haloalkoxy.

In another preferred embodiment, $R^4$ represents —N($R^9$)$_2$, $C_1$-$C_3$ alkyl, —(CH$_2$)$_m$R$^{10}$, —O(CH$_2$)$_m$R$^{10}$ or —NH(CH$_2$)$_m$R$^{10}$, wherein the alkyl moiety is unsubstituted or substituted with one or two substituents independently selected from halogen, hydroxyl, methylamino, dimethylamino, $C_1$-$C_3$ alkyl, $C_1$-$C_3$ haloalkyl, $C_1$-$C_3$ alkoxy and $C_1$-$C_3$ haloalkoxy.

In another preferred embodiment, $R^4$ represents —N($R^9$)$_2$, $C_1$-$C_3$ alkyl (e.g. unsubstituted methyl) or —O(CH$_2$)$_m$R$^{10}$, wherein the alkyl moiety is unsubstituted or substituted with one or two substituents independently selected from halogen, hydroxyl, methylamino, dimethylamino, $C_1$-$C_3$ alkyl, $C_1$-$C_3$ haloalkyl, $C_1$-$C_3$ alkoxy and $C_1$-$C_3$ haloalkoxy.

In another preferred embodiment of the invention, $R^9$ represents methyl, $C_3$-$C_6$ alkyl or $C_1$-$C_6$ haloalkyl, or two $R^9$ together with the nitrogen atom to which they are attached form a saturated or unsaturated 4-, 5- or 6-membered heterocyclic ring optionally comprising one or two further ring heteroatoms independently selected from nitrogen and oxygen atoms, the heterocyclic ring being unsubstituted or substituted with one, two or three substituents independently selected from halogen, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy.

In another preferred embodiment, $R^9$ represents methyl, $C_3$-$C_6$ alkyl or $C_1$-$C_6$ haloalkyl, or two $R^9$ together with the nitrogen atom to which they are attached form a saturated or unsaturated 4-, 5- or 6-membered heterocyclic ring optionally comprising one or two further ring heteroatoms independently selected from nitrogen and oxygen atoms, the heterocyclic ring being unsubstituted or substituted with one or two substituents independently selected from halogen, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy.

In another preferred embodiment, two $R^9$ together with the nitrogen atom to which they are attached form a saturated or unsaturated 4-, 5- or 6-membered heterocyclic ring optionally comprising one or two further ring heteroatoms independently selected from nitrogen and oxygen atoms, the heterocyclic ring being unsubstituted or substituted with one or two substituents independently selected from halogen, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy.

In one embodiment, two $R^9$ together with the nitrogen atom to which they are attached form an optionally substituted azetidine

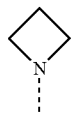

wherein - - - represents the bond by which the azetidine is attached to the rest of the molecule.

In another embodiment, two $R^9$ together with the nitrogen atom to which they are attached form an optionally substituted saturated or unsaturated 5-membered heterocyclic ring selected from:

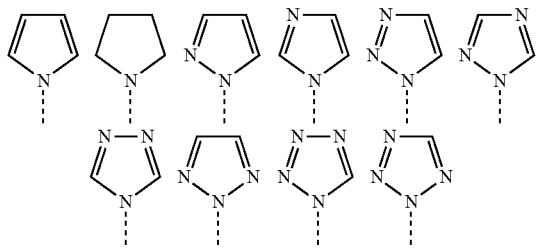

wherein - - - represents the bond by which the heterocyclic ring is attached to the rest of the molecule.

In another embodiment, two $R^9$ together with the nitrogen atom to which they are attached form an optionally substituted saturated or unsaturated 6-membered heterocyclic ring selected from:

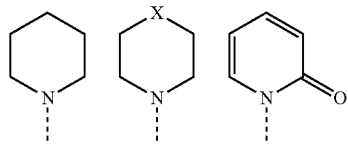

wherein X is —NH—, —O— or —S—, preferably —NH— or —O—, and wherein ------ represents the bond by which the heterocyclic ring is attached to the rest of the molecule.

In another preferred embodiment of the invention, $R^{10}$ represents a saturated or unsaturated 3-, 4-, 5- or 6-membered carbocyclic ring or a saturated or unsaturated 4-, 5- or 6-membered heterocyclic ring, the heterocyclic ring comprising one, two or three ring heteroatoms independently selected from nitrogen and oxygen atoms, wherein the carbocyclic or heterocyclic ring is unsubstituted or substituted with one, two or three substituents independently selected from halogen, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy.

In another preferred embodiment, $R^{10}$ represents a saturated or unsaturated 3-, 4-, 5- or 6-membered carbocyclic ring or a saturated or unsaturated 4-, 5- or 6-membered heterocyclic ring, the heterocyclic ring comprising one, two or three ring heteroatoms independently selected from nitrogen and oxygen atoms, wherein the carbocyclic or heterocyclic ring is unsubstituted or substituted with one or two substituents independently selected from halogen, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy.

In one embodiment, $R^{10}$ represents an optionally substituted saturated or unsaturated 5-membered heterocyclic ring selected from:

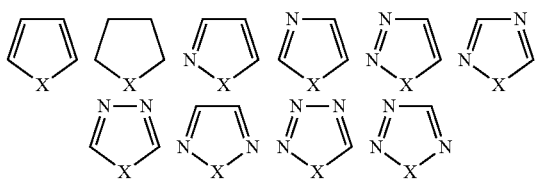

wherein X is —NH—, —O— or —S—, preferably —NH— or —O—, preferably —O—, and wherein any suitable heterocyclic ring atom is attached to the rest of the molecule.

In another embodiment, $R^{10}$ represents an optionally substituted saturated or unsaturated 6-membered heterocyclic ring selected from:

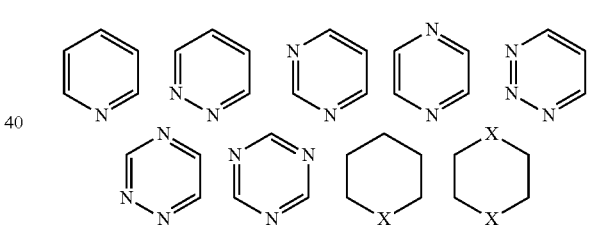

wherein X is —NH—, —O— or —S—, preferably —NH— or —O—, and wherein any suitable heterocyclic ring atom is attached to the rest of the molecule.

In another preferred embodiment of the invention, m is 0, 1 or 2. In another preferred embodiment, m is 0 or 1. In another preferred embodiment, m is 1. In another preferred embodiment, m is 0.

$R^5$ may represent hydrogen or halogen. In a preferred embodiment of the invention, $R^5$ represents hydrogen, fluorine, chlorine or bromine. In another preferred embodiment, $R^5$ represents hydrogen, fluorine or chlorine. In another preferred embodiment, $R^5$ represents hydrogen or fluorine. In another preferred embodiment, $R^5$ represents hydrogen.

$R^4$ and $R^5$ together with the benzyl group to which they are attached may form a 5- to 7-membered carbocyclic or heterocyclic ring, the heterocyclic ring comprising at least one ring heteroatom (e.g. one, two, three, four, five or six ring heteroatoms) independently selected from nitrogen, oxygen and sulphur atoms (in particular nitrogen and oxygen atoms), wherein the carbocyclic or heterocyclic ring is unsubstituted or substituted with at least one substituent (e.g. one, two, three, four, five, six or seven substituents) independently selected from halogen, cyano, hydroxyl, oxo, amino, methylamino, dimethylamino, $C_1$-$C_6$ alkyl, $C_1$-$C_6$ haloalkyl, $C_1$-$C_6$ alkoxy, $C_1$-$C_6$ haloalkoxy, —$(CH_2)_nR^{11}$ and —$O(CH_2)_nR^{11}$; wherein $R^{11}$ represents a saturated or unsaturated 3- to 7-membered carbocyclic ring or a saturated or unsaturated 4- to 7-membered heterocyclic ring, the heterocyclic ring comprising at least one ring heteroatom (e.g. one, two, three, four, five or six ring heteroatoms) independently selected from nitrogen, oxygen and sulphur atoms (in particular nitrogen and oxygen atoms), wherein the carbocyclic or heterocyclic ring is unsubstituted or substituted with at least one substituent (e.g. one, two, three, four, five, six or seven substituents) independently selected from halogen, cyano, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy; and n is 0, 1, 2 or 3.

In a preferred embodiment of the invention, $R^4$ and $R^5$ together with the benzyl group to which they are attached form a 5- or 6-membered carbocyclic or heterocyclic ring, the heterocyclic ring comprising one, two or three ring heteroatoms independently selected from nitrogen and oxygen atoms, wherein the carbocyclic or heterocyclic ring is unsubstituted or substituted with one, two or three substituents independently selected from halogen, hydroxyl, oxo, amino, methylamino, dimethylamino, $C_1$-$C_4$ alkyl, $C_1$-$C_4$ haloalkyl, $C_1$-$C_4$ alkoxy, $C_1$-$C_4$ haloalkoxy, —$(CH_2)_nR^{11}$ and —$O(CH_2)_nR^{11}$; wherein $R^{11}$ represents a saturated or unsaturated 3-, 4-, 5- or 6-membered carbocyclic ring or a saturated or unsaturated 5- or 6-membered heterocyclic ring, the heterocyclic ring comprising one, two or three ring heteroatoms independently selected from nitrogen and oxygen atoms, wherein the carbocyclic or heterocyclic ring is unsubstituted or substituted with one, two or three substituents independently selected from halogen, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy; and n is 0, 1, 2 or 3.

In another preferred embodiment, $R^4$ and $R^5$ together with the benzyl group to which they are attached form a 6-membered heterocyclic ring, the heterocyclic ring comprising one or two ring heteroatoms independently selected from nitrogen and oxygen atoms, wherein the heterocyclic ring is substituted with one, two or three substituents independently selected from halogen, hydroxyl, oxo, amino, methylamino, dimethylamino, $C_1$-$C_4$ alkyl, $C_1$-$C_4$ haloalkyl, $C_1$-$C_4$ alkoxy, $C_1$-$C_4$ haloalkoxy, —$(CH_2)_nR^{11}$ and —$O(CH_2)_nR^{11}$; wherein R11 represents a saturated or unsaturated 3-, 4-, 5- or 6-membered carbocyclic ring or a saturated or unsaturated 5- or 6-membered heterocyclic ring, the heterocyclic ring comprising one or two ring heteroatoms independently selected from nitrogen and oxygen atoms, wherein the carbocyclic or heterocyclic ring is unsubstituted or substituted with one or two substituents independently selected from halogen, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy; and n is 0, 1, 2 or 3.

In another preferred embodiment of the invention, $R^4$ and $R^5$ together with the benzyl group to which they are attached form a 5- or 6-membered carbocyclic or heterocyclic ring, the heterocyclic ring comprising one, two or three ring heteroatoms independently selected from nitrogen and oxygen atoms, wherein the carbocyclic or heterocyclic ring is unsubstituted or substituted with one, two or three substituents independently selected from halogen, hydroxyl, oxo, amino, methylamino, dimethylamino, $C_1$-$C_4$ alkyl, $C_1$-$C_4$ haloalkyl, $C_1$-$C_4$ alkoxy, $C_1$-$C_4$ haloalkoxy, —$(CH_2)_nR^{11}$ and —$O(CH_2)_nR^{11}$.

In another preferred embodiment, $R^4$ and $R^5$ together with the benzyl group to which they are attached form a 6-membered heterocyclic ring, the heterocyclic ring comprising one or two ring heteroatoms independently selected from nitrogen and oxygen atoms, wherein the heterocyclic ring is substituted with one, two or three substituents independently selected from halogen, hydroxyl, oxo, amino, methylamino, dimethylamino, $C_1$-$C_4$ alkyl, $C_1$-$C_4$ haloalkyl, $C_1$-$C_4$ alkoxy, $C_1$-$C_4$ haloalkoxy, —$(CH_2)_nR^{11}$ and —$O(CH_2)_nR^{11}$.

In one embodiment, $R^4$ and $R^5$ together with the benzyl group to which they are attached form an optionally substituted 5-membered heterocyclic ring selected from:

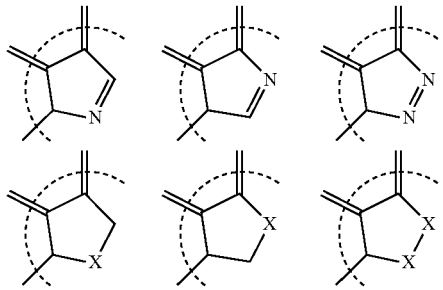

wherein X is —NH—, —O— or —S—, preferably —NH— or —O—.

In another embodiment, $R^4$ and $R^5$ together with the benzyl group to which they are attached form an optionally substituted 6-membered heterocyclic ring selected from:

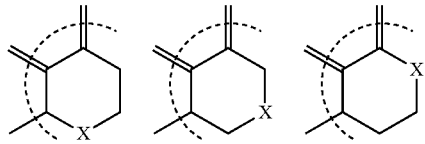

wherein X is —NH—, —O— or —S—, preferably —NH— or —O—.

In another preferred embodiment of the invention, $R^{11}$ represents a saturated or unsaturated 3-, 4-, 5- or 6-membered carbocyclic ring or a saturated or unsaturated 5- or 6-membered heterocyclic ring, the heterocyclic ring comprising one, two or three ring heteroatoms independently selected from nitrogen and oxygen atoms, wherein the carbocyclic or heterocyclic ring is unsubstituted or substituted with one, two or three substituents independently selected from halogen, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy.

In another preferred embodiment, $R^{11}$ represents a saturated or unsaturated 3-, 4-, 5- or 6-membered carbocyclic ring or a saturated or unsaturated 5- or 6-membered heterocyclic ring, the heterocyclic ring comprising one or two ring heteroatoms independently selected from nitrogen and oxygen atoms, wherein the carbocyclic or heterocyclic ring is unsubstituted or substituted with one or two substituents independently selected from halogen, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy.

In one embodiment, $R^{11}$ represents an optionally substituted saturated or unsaturated 5-membered heterocyclic ring selected from:

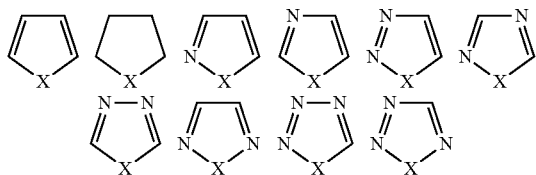

wherein X is —NH—, —O— or —S—, preferably —NH— or —O—, preferably —O—, and wherein any suitable heterocyclic ring atom is attached to the rest of the molecule.

In another embodiment, $R^{11}$ represents an optionally substituted saturated or unsaturated 6-membered heterocyclic ring selected from:

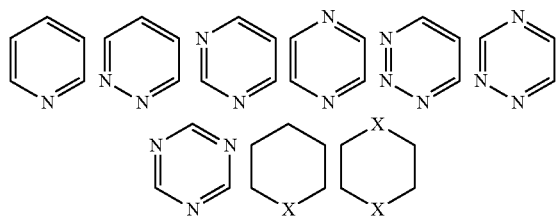

wherein X is —NH—, —O— or —S—, preferably —NH— or —O—, and wherein any suitable heterocyclic ring atom is attached to the rest of the molecule.

In another preferred embodiment of the invention, n is 0, 1 or 2. In another preferred embodiment, n is 0 or 1. In another preferred embodiment, n is 1.

$R^6$ represents hydrogen, halogen, $C_1$-$C_6$ alkyl or $C_1$-$C_6$ haloalkyl. In a preferred embodiment of the invention, $R^6$ represents hydrogen, halogen, $C_1$-$C_3$ alkyl or $C_1$-$C_3$ haloalkyl. In another preferred embodiment, $R^6$ represents hydrogen or halogen. In another preferred embodiment, $R^6$ represents hydrogen, fluorine, chlorine or bromine. In another preferred embodiment, $R^6$ represents hydrogen, fluorine or chlorine. In another preferred embodiment, $R^6$ represents hydrogen or fluorine. In another preferred embodiment, $R^6$ represents hydrogen.

In a preferred embodiment of the invention, Z represents —O—. In another embodiment, Z represents —$CH_2$—.

Examples of compounds of the invention include:
(2S)—N-((cis)-4-hydroxy-3,4-dihydro-2H-1-benzopyran-3-yl)-2-phenylpropanamide;
(2S)—N-((trans)-4-hydroxy-3,4-dihydro-2H-1-benzopyran-3-yl)-2-phenylpropanamide;
(2S)—N-((cis)-6-fluoro-4-hydroxy-3,4-dihydro-2H-1-benzopyran-3-yl)-2-phenylpropanamide;
(2S)—N-(4-oxo-3,4-dihydro-2H-1-benzopyran-3-yl)-2-phenylpropanamide;
(2S)—N-((cis)-4-hydroxy-4-methyl-3,4-dihydro-2H-1-benzopyran-3-yl)-2-phenylpropanamide;
(2S)—N-[(cis)-4-(methylamino)-3,4-dihydro-2H-1-benzopyran-3-yl]-2-phenylpropanamide;
(2S)—N-((trans)-4-methoxy-3,4-dihydro-2H-1-benzopyran-3-yl)-2-phenylpropanamide;
(2S)—N-((trans)-4-methanesulfonyl-3,4-dihydro-2H-1-benzopyran-3-yl)-2-phenylpropanamide;
(2S)—N-[(trans)-4-(methylamino)-3,4-dihydro-2H-1-benzopyran-3-yl]-2-phenylpropanamide;
(1S)-2-(cyclopropylmethyl)-N-((trans)-4-methoxy-3,4-dihydro-2H-1-benzopyran-3-yl)-3-oxo-1,2,3,4-tetrahydroisoquinoline-1-carboxamide;
(2S)-2-(4-fluorophenyl)-N-((trans)-4-methanesulfonyl-3,4-dihydro-2H-1-benzopyran-3-yl)propanamide;
(2S)-2-(4-chlorophenyl)-N-((trans)-4-methanesulfonyl-3,4-dihydro-2H-1-benzopyran-3-yl)propanamide;
(2S)-2-(4-fluorophenyl)-N-[(trans)-4-(methylamino)-3,4-dihydro-2H-1-benzopyran-3-yl]propanamide;
(2S)-2-(4-fluorophenyl)-N-[(trans)-4-(methylamino)-3,4-dihydro-2H-1-benzopyran-3-yl]propanamide;
2-(4-fluorophenyl)-N-((trans)-4-methoxy-3,4-dihydro-2H-1-benzopyran-3-yl)-2-[3-(trifluoromethoxy)azetidin-1-yl]acetamide;
2-(2,4-difluorophenyl)-N-((trans)-4-methoxy-3,4-dihydro-2H-1-benzopyran-3-yl)-2-[3-(trifluoromethoxy)azetidin-1-yl]acetamide;
(1S)-2-(3-fluoropropyl)-N-((trans)-4-methoxy-3,4-dihydro-2H-1-benzopyran-3-yl)-3-oxo-1,2,3,4-tetrahydroisoquinoline-1-carboxamide;
N-((trans)-4-methoxy-3,4-dihydro-2H-1-benzopyran-3-yl)-2-[(oxan-4-yl)methyl]-3-oxo-1,2,3,4-tetrahydroisoquinoline-1-carboxamide;
N-((trans)-4-methoxy-3,4-dihydro-2H-1-benzopyran-3-yl)-3-oxo-2-[(pyridin-2-yl)methyl]-1,2,3,4-tetrahydroisoquinoline-1-carboxamide;
2-(cyclopropylmethoxy)-2-(4-fluorophenyl)-N-((trans)-4-methoxy-3,4-dihydro-2H-1-benzopyran-3-yl)acetamide;
2-(2,4-difluorophenyl)-N-((trans)-4-methoxy-3,4-dihydro-2H-1-benzopyran-3-yl)-2-[(2-methylpyrimidin-4-yl)oxy]acetamide;
2-(2,4-difluorophenyl)-N-((trans)-4-methoxy-3,4-dihydro-2H-1-benzopyran-3-yl)-2-(2-oxo-1,2-dihydropyridin-1-yl)acetamide;
$N^1$-(trans)-{3-[(2S)-2-(4-fluorophenyl)propanamido]-3,4-dihydro-2H-1-benzopyran-4-yl}-$N^2$-methylbenzene-1,2-dicarboxamide;
(2S)-2-(4-fluorophenyl)-N-[(trans)-4-(pyrrolidin-1-yl)-3,4-dihydro-2H-1-benzopyran-3-yl]propanamide;
(2S)—N-[(trans)-4-(azetidin-1-yl)-3,4-dihydro-2H-1-benzopyran-3-yl]-2-(4-fluorophenyl)propanamide;
(2S)—N-[(trans)-4-(dimethylamino)-3,4-dihydro-2H-1-benzopyran-3-yl]-2-(4-fluorophenyl)propanamide;
(2S)—N-[(trans)-4-(3,3-difluoropyrrolidin-1-yl)-3,4-dihydro-2H-1-benzopyran-3-yl]-2-(4-fluorophenyl)propanamide;
(2S)-2-(4-fluorophenyl)-N-[(trans)-4-(morpholin-4-yl)-3,4-dihydro-2H-1-benzopyran-3-yl]propanamide;
(1S)-2-(cyclopropylmethyl)-N-((trans)-4-hydroxy-3,4-dihydro-2H-1-benzopyran-3-yl)-3-oxo-1,2,3,4-tetrahydroisoquinoline-1-carboxamide;
(2S)-2-(4-fluorophenyl)-N-((cis)-4-hydroxy-3,4-dihydro-2H-1-benzopyran-3-yl)propanamide;
and enantiomers, diastereoisomers and mixtures thereof; and pharmaceutically acceptable salts of any of the foregoing.

It should be noted that each of the chemical compounds listed above represents a particular and independent aspect of the invention.

II. Methods of Preparation

The present invention further provides a process for the preparation of a compound of formula (I) or a pharmaceutically acceptable salt thereof as defined above, which comprises reacting a compound of formula (II) or a salt (e.g. hydrochloride salt) thereof

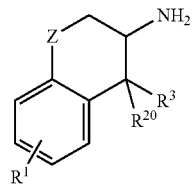

in which Z, $R^1$ and $R^3$ are as defined in formula (I) above, and $R^{20}$ represents hydrogen, hydroxyl, $C_1$-$C_6$ alkyl, $C_1$-$C_6$ haloalkyl, $C_1$-$C_6$ alkoxy, $C_1$-$C_6$ haloalkoxy, —N($R^7$)$_2$, —SO$_2$R$^8$ or —SR$^8$, with a compound of formula (III) or a salt (e.g. hydrochloride salt) thereof

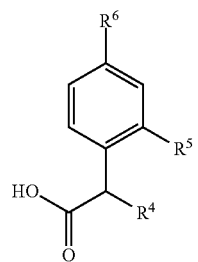

in which $R^4$, $R^5$ and $R^6$ are as defined in formula (I) above; and optionally thereafter carrying out one or more of the following procedures:
  converting a compound of formula (I) into another compound of formula (I)
  removing any protecting groups
  forming a pharmaceutically acceptable salt.

The above process may conveniently be carried out by combining the amine of formula (II) with the carboxylic acid of formula (III) in the presence of a coupling reagent such as:
(1) HATU (1-[bis(dimethylamino)methylene]-1H-1,2,3-triazolo[4,5-b]pyridinium 3-oxid hexafluorophosphate) with N,N-diisopropylethylamine in a solvent such as dichloromethane at room temperature to 60° C.; or
(2) propylphosphonic anhydride with triethylamine in a solvent such as dichloromethane or tetrahydrofuran at room temperature to 60° C.;
followed, if necessary, by removal of any protecting groups.

$R^{20}$ may represents —SR$^8$. —SR$^8$ may be converted into —SO$_2$R$^8$ by treatment with, for example, meta-chloroperbenzoic acid in a solvent such as dichloromethane.

Compounds of formulae (II) and (III) are known compounds or may be prepared according to processes known in the art.

A compound of formula (I), (II) or (III) may be converted into another compound of formula (I), (II) or (III) respectively. For example, a hydroxyl substituent group (—OH) may be converted into:
(1) —OMe by treatment with, for example, sodium hydride in a solvent such as dimethylformamide, followed by treatment with methyl iodide; or alternatively by treatment with methyl iodide and silver oxide in a solvent such as acetonitrile;
(2) —OCH$_2$-cyclopropyl by treatment with, for example, sodium hydride in a solvent such as dichloromethane, followed by treatment with (bromomethyl)cyclopropane;
(3) —NHMe by treatment with, for example, methanesulfonic anhydride and triethylamine in a solvent such as tetrahydrofuran, followed by treatment with methanamine;
(4) —SMe by treatment with, for example, methanesulfonic anhydride and triethylamine in a solvent such as tetrahydrofuran, followed by treatment with sodium methanethiolate and 15-crown-5;
(5) pyrrolidin-1-yl by treatment with, for example, methanesulfonic anhydride and triethylamine in a solvent such as tetrahydrofuran, followed by treatment with pyrrolidine;
(6) 3,3-difluoropyrrolidin-1-yl by treatment with, for example, methanesulfonic anhydride and triethylamine in a solvent such as tetrahydrofuran, followed by treatment with 3,3-difluoropyrrolidine hydrochloride and triethylamine;
(7) 1,3-dioxo-2,3-dihydro-1H-isoindol-2-yl by treatment with, for example, methanesulfonic anhydride and triethylamine in a solvent such as tetrahydrofuran, followed by treatment with potassium 1,3-dioxoisoindolin-2-ide and 18-crown-6;
(8)

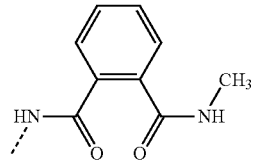

by treatment with, for example, methanesulfonic anhydride and triethylamine in a solvent such as tetrahydrofuran, followed by treatment with potassium 1,3-dioxoisoindolin-2-ide and 18-crown-6, followed by treatment with methanamine in a solvent such as ethanol.

A bromine substituent group (—Br) may be converted into:
(1) —O-(2-methylpyrimidin-4-yl) by treatment with, for example, caesium carbonate and 2-methylpyrimidin-4-ol in a solvent such as dimethylformamide;
(2) —O-(2-oxo-1,2-dihydropyridin-1-yl) by treatment with, for example, caesium carbonate and pyridin-2-ol in a solvent such as dimethylformamide.

A carbonyl substituent group (C=O) may be converted into:
(1) C(OH)(Me) by treatment with, for example, methylmagnesium bromide in a solvent such as diethyl ether or tetrahydrofuran;
(2) CH(NHMe) by treatment with, for example, methanamine in a solvent such as ethanol, followed by treatment with NaBH$_4$.

It will be appreciated by those skilled in the art that in the process of the present invention certain functional groups such as phenol, hydroxyl or amino groups in the reagents may need to be protected by protecting groups. Thus, the preparation of the compounds of formula (I) may involve, at an appropriate stage, the introduction and/or removal of one or more protecting groups.

The protection and deprotection of functional groups is described, for example, in 'Protective Groups in Organic Chemistry', edited by J. W. F. McOmie, Plenum Press (1973); 'Greene's Protective Groups in Organic Synthesis', 4th edition, T. W. Greene and P. G. M. Wuts, Wiley-Interscience (2007); and 'Protecting Groups', 3rd edition, P. J. Kocienski, Thieme (2005).

The compounds of formula (I) above may be converted to a pharmaceutically acceptable salt thereof, preferably an acid addition salt such as a formate, hemi-formate, hydrochloride, hydrobromide, benzenesulphonate (besylate), saccharin (e.g. monosaccharin), trifluoroacetate, sulphate, nitrate, phosphate, acetate, fumarate, maleate, tartrate, lactate, citrate, pyruvate, succinate, valerate, propanoate, butanoate, malonate, oxalate, 1-hydroxy-2-napthoate (xinafoate), methanesulphonate or p-toluenesulphonate salt. In one embodiment of the invention, the compounds of formula (I) are in the form of a hydrochloride salt.

In one aspect of the invention, compounds of formula (I) may bear one or more radiolabels. Such radiolabels may be introduced by using radiolabel-containing reagents in the synthesis of the compounds of formula (I), or may be introduced by coupling the compounds of formula (I) to chelating moieties capable of binding to a radioactive metal atom. Such radiolabeled versions of the compounds may be used, for example, in diagnostic imaging studies.

Unless stated otherwise, any atom specified herein may also be an isotope of said atom. For example, the term "hydrogen" encompasses $^1H$, $^2H$ and $^3H$. Similarly, carbon atoms are to be understood to include $^{12}C$, $^{13}C$ and $^{14}C$, nitrogen atoms are to be understood to include $^{14}N$ and $^{15}N$, and oxygen atoms are to be understood to include $^{16}O$, $^{17}O$ and $^{18}O$.

In a further aspect of the invention, compounds of formula (I) may be isotopically labelled. As used herein, an "isotopically labelled" compound is one in which the abundance of a particular nuclide at a particular atomic position within the molecule is increased above the level at which it occurs in nature.

Compounds of formula (I) and their salts may be in the form of hydrates or solvates which form an aspect of the present invention. Such solvates may be formed with common organic solvents, including but not limited to, alcoholic solvents e.g. methanol, ethanol or isopropanol.

Where compounds of formula (I) are capable of existing in stereoisomeric forms, it will be understood that the invention encompasses the use of all geometric and optical isomers (including atropisomers) of the compounds of formula (I) and mixtures thereof including racemates. The use of tautomers and mixtures thereof also forms an aspect of the present invention. Enantiomerically pure forms are particularly desired. "Enantiomerically pure" denotes the presence of at least 75% w (percent by weight), in particular at least 90% w and, more particularly, at least 95% w of a single enantiomer of a compound.

Compounds of formula (I) and their salts may be amorphous or in a polymorphic form or a mixture of any of these, each of which forms an aspect of the present invention.

In some embodiments, the compound comprises the formula (2S)-2-(4-fluorophenyl)-N-((trans)-4-methanesulfonyl-3,4-dihydro-2H-1-benzopyran-3-yl)propanamide or a pharmaceutically acceptable salt thereof.

III. Treatment of Disease, Disorders, or Conditions

The compounds of formula (I) and their pharmaceutically acceptable salts have activity as pharmaceuticals and may be used in treating conditions or disorders associated with changes in one or both of the glutamatergic and GABAergic signalling pathways regulated in full or in part by metabotropic glutamate receptor 7.

Thus, the present invention provides a compound of formula (I) or a pharmaceutically acceptable salt thereof as hereinbefore defined for use in therapy, in particular for the treatment of conditions associated with metabotropic glutamate receptor 7 (mGluR7).

The present invention also provides the use of a compound of formula (I) or a pharmaceutically acceptable salt thereof as hereinbefore defined for the preparation of a medicament for the treatment of conditions associated with metabotropic glutamate receptor 7 (mGluR7).

The present invention still further provides embodiments of a method of treating a condition associated with metabotropic glutamate receptor 7 which comprises administering to a patient in need thereof a therapeutically effective amount of a compound of formula (I) or a pharmaceutically acceptable salt thereof as hereinbefore defined. In some embodiments, the compound is (2S)-2-(4-fluorophenyl)-N-((trans)-4-methanesulfonyl-3,4-dihydro-2H-1-benzopyran-3-yl)propanamide or a pharmaceutically acceptable salt thereof for use as a medicament for treatment of a disease, disorder, or condition associated with glutamatergic and GABAergic signalling pathways regulated in full or in part by metabotropic glutamate receptor 7 (mGluR7).

Alternatively, in various embodiments of the invention herein include a compound comprising the formula (2S)-2-(4-fluorophenyl)-N-((trans)-4-methanesulfonyl-3,4-dihydro-2H-1-benzopyran-3-yl)propanamide or a pharmaceutically acceptable salt thereof for use as a medicament for treatment of a disease, disorder, or condition of the central nervous system.

In some embodiments, the compound is a selective agonist of mGluR7. In certain embodiments, the compound is more selective for mGluR7 than for mGluR4 or mGluR8. In some embodiments, the compound has an $EC_{50}$ within at least one range selected from the group of ranges consisting of about 1 nM to about 3 nM, about 2 nM to about 4 nM, about 3 nM to about 5 nM, about 4 nM to about 6 nM, and about 6 nM to about 8 nM. In certain embodiments, the compound has an $EC_{50}$ of 1.8+3.5 nM. In certain embodiments, the compound has an $EC_{50}$ of 6.9+0.8 nM. In some embodiments, the compound is an allosteric agonist of mGluR7.

Additionally, various embodiments of the invention herein include a method of treating a subject for a disease, disorder, or condition of the central nervous system in a subject, the method comprising: administering to the subject a therapeutically effective amount of compound (2S)-2-(4-fluorophenyl)-N-((trans)-4-methanesulfonyl-3,4-dihydro-2H-1-benzopyran-3-yl)propanamide or a pharmaceutically acceptable salt thereof, thereby selectively agonizing mGluR7 to treat the disease, disorder, or condition. The method further comprising modulating by the compound neurotransmitter release in the subject to treat the disease, disorder, or condition. For example, the neurotransmitter is glutamate.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disorder or condition in question. Persons at risk of developing a particular disorder or condition generally include those having a family history of the disorder or condition, or those who have been identified by genetic testing or screening to be particularly susceptible to developing the disorder or condition or those in the prodromal phase of a disorder.

The terms "treat", "treatment" and "treating" include improvement of the conditions described herein. The terms "treat", "treatment" and "treating" include all processes providing slowing, interrupting, arresting, controlling, or stopping of the state or progression of the conditions described herein, but does not necessarily indicate a total elimination of all symptoms or a cure of the condition. The terms "treat", "treatment" and "treating" are intended to include therapeutic as well as prophylactic treatment of such conditions.

As used herein the terms "condition", "disorder" and "disease" relate to any unhealthy or abnormal state. The term "conditions associated with metabotropic glutamate receptor 7" includes conditions, disorders and diseases in which the modulation of mGluR7 may provide a therapeutic benefit, examples of which include:

(1) Nervous system disorders: Parkinson's disease, including dementia associated with Parkinson's disease; Alzheimer's disease; Huntington's Chorea; amyotrophic lateral sclerosis; multiple sclerosis; bipolar disorder; and psychiatric disorders such as schizophrenia, post-traumatic stress disorder, anxiety disorders and depression (e.g. major depressive disorder);
(2) Addiction disorders: alcohol, drug or nicotine addiction;
(3) Hearing disorders: hearing loss and/or tinnitus caused by age, noise or trauma; and
(4) Others: idiopathic autism; severe neonatal encephalopathy; autism spectrum disorder (ASD); X-linked intellectual disability (also known as X-linked mental retardation); epilepsy; cerebral ischemias; eye disorders; Rett syndrome (17); and pain (e.g. inflammatory pain or neuropathic pain).

Schizophrenia is a debilitating psychiatric disorder characterised by a combination of negative symptoms (such as social withdrawal, anhedonia, avolition and apathy) and positive symptoms (including hallucinations, delusions and paranoia) as well as marked cognitive deficits (such as impairment of executive function). The executive function (EF) has been defined as "a set of abilities, which allows us to invoke voluntary control of our behavioral responses. These functions enable human beings to develop and carry out plans, make up analogies, obey social rules, solve problems, adapt to unexpected circumstances, do many tasks simultaneously, and locate episodes in time and place. EF includes divided attention and sustained attention, working memory (WM), set-shifting, flexibility, planning, and the regulation of goal directed behavior and can be defined as a brain function underlying the human faculty to act or think not only in reaction to external events but also in relation with internal goals and states" (Orellana G. and Slachevsky A., 2013. Executive Functioning in Schizophrenia. *Front. Psychiatry*, 4, 35).

Accordingly, the present invention also provides a method of treating a negative symptom, a positive symptom and/or a cognitive deficit associated with a psychiatric disorder, especially schizophrenia, which comprises administering to a patient in need thereof a therapeutically effective amount of a compound of formula (I) or a pharmaceutically acceptable salt thereof as hereinbefore defined.

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight (µg/kg) to 100 micrograms per kilogram body weight (µg/kg). Alternatively, if the compound is administered orally, then the daily dosage of the compound of the invention may be in the range from 0.01 micrograms per kilogram body weight (µg/kg) to 100 milligrams per kilogram body weight (mg/kg).

IV. Pharmaceutical Compositions

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier.

Therefore, the present invention further provides a pharmaceutical composition comprising a compound of formula (I) or a pharmaceutically acceptable salt thereof as hereinbefore defined, in association with a pharmaceutically acceptable adjuvant, diluent or carrier.

The invention still further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

Conventional procedures for the selection and preparation of suitable pharmaceutical formulations are described in, for example, "Pharmaceutics—The Science of Dosage Form Design", M. E. Aulton, Churchill Livingstone, 1988.

Pharmaceutically acceptable adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins such as human serum albumin, buffer substances such as phosphates, glycerine, sorbic acid, potassium sorbate, partial glyceride mixtures of saturated vegetable fatty acids, water, salts or electrolytes such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the present invention may be administered orally, parenterally, by inhalation spray, rectally, nasally, buccally, vaginally or via an implanted reservoir. Oral administration is preferred. The pharmaceutical compositions of the invention may contain any conventional non-toxic pharmaceutically acceptable adjuvants, diluents or carriers. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. The suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable diluents and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant.

The pharmaceutical compositions of this invention may be orally administered in any orally acceptable dosage form including, but not limited to, capsules, tablets, powders, granules, and aqueous suspensions and solutions. These dosage forms are prepared according to techniques well-known in the art of pharmaceutical formulation. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of the invention may also be administered in the form of suppositories for rectal administration. These compositions can be prepared by mixing the active ingredient with a suitable non-irritating excipient which is solid at room temperature but liquid at the rectal temperature and therefore will melt in the rectum to release the active ingredient. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The compounds of the invention (that is, compounds of formula (I) and pharmaceutically acceptable salts thereof) may also be administered in conjunction with other compounds used for the treatment of the above conditions.

The invention therefore further relates to combination therapies wherein a compound of the invention or a pharmaceutical composition or formulation comprising a compound of the invention is administered with another therapeutic agent or agents for the treatment of one or more of the conditions previously indicated. Such therapeutic agents may be selected from the following:

(i) anti-addiction drugs including, for example, acamprosate, disulfiram, naltrexone and nalmefene for alcohol dependency, and gabapentin, modafinil, topiramate, vigabatrin and baclofen for drug, particularly cocaine, addiction;

(ii) antidepressants such as amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, reboxetine, robaizotan, sertraline, sibutramine, tianeptine, thionisoxetine, tranylcypromaine, trazodone, trimipramine, venlafaxine, vortioxetine and equivalents and pharmaceutically active isomer(s) and/or metabolite(s) thereof;

(iii) antipsychotics including, for example, amisulpride, aripiprazole, asenapine, benzisoxidil, bifeprunox, brexpiprazole, carbamazepine, cariprazine, clozapine, chlorpromazine, debenzapine, divalproex, duloxetine, eszopiclone, fluphenazine, haloperidol, iloperidone, lamotrigine, loxapine, lurasidone, mesoridazine, olanzapine, paliperidone, perlapine, perphenazine, phenothiazine, phenylbutlypiperidine, pimozide, prochlorperazine, quetiapine, risperidone, sertindole, sulpiride, suproclone, suriclone, thioridazine, trifluoperazine, trimetozine, valproate, valproic acid, zopiclone, zotepine, zicronapine, ziprasidone, and equivalents and pharmaceutically active isomer(s) and/or metabolite(s) thereof;

(iv) anxiolytics including, for example, alnespirone, azapirones, benzodiazepines, barbiturates, and equivalents and pharmaceutically active isomer(s) and/or metabolite(s) thereof. Example anxiolytics include adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, prazosin, quazepam, reclazepam, tracazolate, trepipam, temazepam, triazolam, uldazepam, and zolazepam; and equivalents and pharmaceutically active isomer(s) and/or metabolite(s) thereof;

(v) anticonvulsants including, for example, carbamazepine, valproate, lamotrigine, levetiracetam and gabapentin, and equivalents and pharmaceutically active isomer(s) and/or metabolite(s) thereof;

(vi) Alzheimer's therapies including, for example, donepezil, galantamine, memantine, rivastigmine, tacrine, and equivalents and pharmaceutically active isomer(s) and/or metabolite(s) thereof;

(vii) Parkinson's therapies including, for example, L-dopa, ropinirole, pramipexole, monoamine oxidase type B (MAO-B) inhibitors such as deprenyl, selegiline, and rasagiline, catechol-O-methyl transferase (COMT) inhibitors such as entacapone or tolcapone, adenosine A-2 inhibitors, dopamine re-uptake inhibitors, NMDA antagonists, Nicotine agonists, and Dopamine agonists and inhibitors of neuronal nitric oxide synthase, and equivalents and pharmaceutically active isomer(s) and/or metabolite(s) thereof;

(viii) migraine therapies including, for example, almotriptan, amantadine, botulinum toxin A, bromocriptine, butalbital, cabergoline, dichloralphenazone, dihydroergotamine, eletriptan, frovatriptan, lisuride, naratriptan, pergolide, pramipexole, rizatriptan, ropinirole, sumatriptan, topiramate, zolmitriptan, and zomitriptan, and equivalents and pharmaceutically active isomer(s) and/or metabolite(s) thereof;

(ix) stroke therapies including, for example, abciximab, activase, citicoline, desmoteplase, and equivalents and pharmaceutically active isomer(s) and/or metabolite(s) thereof;

(x) urinary incontinence therapies including, for example, darafenacin, duloxetine, falvoxate, mirabegron, oxybutynin, propiverine, robalzotan, solifenacin, and tolterodine, and equivalents and pharmaceutically active isomer(s) and/or metabolite(s) thereof;

(xi) neuropathic pain therapies including, for example, capsaicin, gabapentin, lidoderm, and pregabalin, and equivalents and pharmaceutically active isomer(s) and/or metabolite(s) thereof;
(xii) nociceptive pain therapies such as celecoxib, etoricoxib, lumiracoxib, rofecoxib, valdecoxib, diclofenac, loxoprofen, naproxen, and paracetamol, and equivalents and pharmaceutically active isomer(s) and/or metabolite(s) thereof;
(xiii) insomnia therapies including, for example, allobarbital, alonimid, amobarbital, benzoctamine, butabarbital, capuride, chloral, cloperidone, clorethate, dexclamol, ethchlorvynol, eszopiclone, etomidate, glutethimide, halazepam, hydroxyzine, lorediplon, mecloqualone, melatonin, mephobarbital, methaqualone, midaflur, nisobamate, pentobarbital, phenobarbital, propofol, ralmeteon, roletamide, suvorexant, triclofos, secobarbital, zaleplon, and zolpidem, zopiclone and equivalents and pharmaceutically active isomer(s) and/or metabolite(s) thereof;
(xiv) mood stabilizers including, for example, carbamazepine, divalproex, gabapentin, lamotrigine, lithium, olanzapine, quetiapine, valproate, valproic acid, and verapamil, and equivalents and pharmaceutically active isomer(s) and/or metabolite(s) thereof;
(xv) 5HT1B ligands such as, for example, compounds disclosed in WO 99/05134 and WO 02/08212;
(xvi) mGluR2 agonists;
(xvii) alpha 7 nicotinic agonists such as, for example, compounds disclosed in WO 96/006098, WO 97/030998, WO 99/003859, WO 00/042044, WO 01/029034, WO 01/60821, WO 01/36417, WO 02/096912, WO 03/087102, WO 03/087103, WO 03/087104, WO 2004/016617, WO 2004/016616, and WO 2004/019947;
(xviii) chemokine receptor CCR1 inhibitors; and
(xix) delta opioid agonists such as, for example, compounds disclosed in WO 97/23466 and WO 02/094794.

Such combination products employ the compounds of this invention within the dosage range described herein and the other pharmaceutically active agent within approved dosage ranges.

The pharmaceutical composition comprising a compound of formula (I) or a pharmaceutically acceptable salt thereof may be administered by any route which results in a therapeutically effective outcome. These include, but are not limited to enteral, gastroenteral, epidural, oral, transdermal, epidural (peridural), intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intraarterial (into an artery), intramuscular (into a muscle), intrathecal (into the spinal canal), intraperitoneal (infusion or injection into the peritoneum), intravesical infusion, extraamniotic administration, transdermal (diffusion through the intact skin for systemic distribution), transmucosal (diffusion through a mucous membrane), insufflation (snorting), sublingual, intratympanic, enema, eye drops (onto the conjunctiva), or in ear drops. In specific embodiments, compositions may be administered in a way which allows them to cross the blood-brain barrier, vascular barrier, or other epithelial barrier.

In some embodiments, the pharmaceutical composition comprising a compound of formula (I) or a pharmaceutically acceptable salt thereof may be administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired effect. The desired dosage may be delivered three times a day, two times a day, once a day, every other day, every third day, every week, every two weeks, every three weeks, or every four weeks. In some embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used.

As used herein, a "split dose" is the division of single unit dose or total daily dose into two or more doses, e.g, two or more administrations of the single unit dose. As used herein, a "single unit dose" is a dose of any therapeutic administered in one dose/at one time/single route/single point of contact, i.e., single administration event. As used herein, a "total daily dose" is an amount given or prescribed in 24 hr period. It may be administered as a single unit dose. In one embodiment, the pharmaceutical composition comprising a compound of formula (I) or a pharmaceutically acceptable salt thereof are administered to a subject in split doses.

EC50 within at least one range selected from the group of ranges consisting of about 1 nM to about 3 nM, about 2 nM to about 4 nM, about 3 nM to about 5 nM, about 4 nM to about 6 nM, and about 6 nM to about 8 nM. In some embodiments, the compound has an EC50 of 1.8+3.5 nM. In some embodiments, the compound has an EC50 of 6.9+0.8 nM. In some embodiments, the compound is an allosteric agonist of mGluR7. In some embodiments, the compound is more selective for mGluR7 than for mGluR4 or mGluR8.

In some embodiments, a method of treating a subject for a disease, disorder, or condition associated with glutamatergic and GABAergic signalling pathways regulated in full or in part by metabotropic glutamate receptor 7 (mGluR7) in a subject comprises administering to the subject a therapeutically effective amount of compound (2S)-2-(4-fluorophenyl)-N-((trans)-4-methanesulfonyl-3,4-dihydro-2H-1-benzopyran-3-yl)propanamide or a pharmaceutically acceptable salt thereof, thereby selectively agonizing mGluR7 to treat the disease, disorder, or condition.

In some embodiments, the method further comprises modulating by the compound neurotransmitter release in the subject to treat the disease, disorder, or condition. In some embodiments of the method, the neurotransmitter is glutamate. In some embodiments of the method, the disease, disorder, or condition is selected from the group consisting of: Parkinson's disease; dementia associated with Parkinson's disease; Alzheimer's disease; Huntington's Chorea; amyotrophic lateral sclerosis; multiple sclerosis; bipolar disorder; schizophrenia; post-traumatic stress disorder; anxiety disorders; depression; alcohol addiction; drug addiction; nicotine addiction; hearing loss; tinnitus; idiopathic autism; severe neonatal encephalopathy; autism spectrum disorder (ASD); X-linked intellectual; epilepsy; cerebral ischemias; eye disorders; Rett syndrome; and pain. In some embodiments of the method, the compound is formulated in a concentration selected from the ranges in the group consisting of: about 0.001 µM to about 0.01 µM, about 0.01 µM to about 0.1 µM, about 0. 1 µM to about 1.0 µM, and about 1.0 µM to about 10 µM. In some embodiments of the method, the compound has a concentration greater than about 0.001 µM. In some embodiments of the method, the compound has a concentration selected from the group consisting of about 1 µM, about 5 µM, and about 10 µm.

EXAMPLES

The present invention will now be further explained by reference to the following illustrative examples, in which the starting materials and reagents used are available from commercial suppliers or prepared via literature procedures.
Experimental Procedures
1. Nuclear Magnetic Resonance (NMR)

NMR spectra were recorded at 400 MHz or 300 MHz as stated and at 300.3 K, 298.2 K or 293 K unless otherwise stated; the chemical shifts (δ) are reported in parts per million. Spectra were recorded using a Bruker (trade mark) 400 AVANCE instrument fitted with a 5 mm BBFO probe with instrument controlled by Bruker TopSpin 2.1 software, or by a Bruker 400 AVANCE-III HD instrument fitted with a 5 mm BBFO smart probe or a 5 mm BBFO probe with instrument controlled by Bruker TopSpin 3.2 software, or by a Bruker 400 AVANCE-III instrument fitted with a 5 mm BBFO probe with instrument controlled by Bruker Topspin 3.0 software or by a Bruker 300 MHz AVANCE II instrument fitted with a 5 mm DUL probe with instrument controlled by Bruker TopSpin 1.3 software, or 5 mm BBFO probe controlled by Bruker Topspin 3.2 software, or by a JEOL 400 Lambda instrument fitted with a 5 mm 40TH5 probe with instrument controlled by a Windows 7 workstation running Delta 4.3.6 software.
2. Purification Purity was assessed using one or more of the following:
Ultra Performance Liquid Chromatography (UPLC) with UV (photodiode array) detection over a wide range of wavelengths, normally 220-450 nm, using a Waters (trade mark) Acquity UPLC system equipped with Acquity UPLC BEH, HSS or HSS T3 C18 columns (2.1 mm id×50 mm long) operated at 50 or 60° C. Mobile phases typically consisted of acetonitrile mixed with water containing either 0.1% formic acid, 0.1% trifluoroacetic acid (TFA) or 0.025% ammonia. Mass spectra were recorded with a Waters SQD single quadrupole mass spectrometer using atmospheric pressure ionisation.
UPLC with UV (photodiode array) detection over a wide range of wavelengths, normally 220-450 nm, using Shimadzu (trade mark) Nexera X2 UPLC controlled by Lab Solution software equipped with Acquity UPLC BEH, HSS or HSS T3 C18 columns (2.1 mm id×50 mm long) operated at 50° C. Mobile phases typically consisted of acetonitrile mixed with water containing either 0.1% formic acid, 0.1% TFA or 0.025% ammonia. Mass spectra were recorded with a Shimadzu single quadrupole mass spectrometer using DUIS ionisation.
UPLC with UV (photodiode array) detection over a wide range of wavelengths, normally 210-315 nm, using Agilent 1260 Infinity series LC equipped with Agilent Poroshell 120 EC-C18 (2.7 µm, 3.0 mm id×50 mm long). Mobile phases typically consisted of acetonitrile mixed with water containing either 0.1% formic acid. Mass spectra were recorded with a API 2000 mass spectrometer using electrospray ionisation.

Compounds were purified using normal phase chromatography on silica, using Biotage (trade mark) KP-Sil cartridges, Interchim (trade mark) PuriFlash cartridges or Kinesis (trade mark) Telos silica cartridges, or on basic silica using Biotage KP-NH cartridges, or by reverse phase chromatographic methods using Biotage KP-C18-HS cartridges or by Biotage Isolute SCX-2 or Phenomenex (trade mark) Strata ABW catch-release cartridges, or by preparative high performance liquid chromatography (HPLC).

Preparative HPLC was performed using Agilent Technologies (trade mark) 1100 Series system or a Waters autopurification LC/MS system or a Shimadzu semi prep HPLC system, typically using Waters 19 mm id×250 mm long C18 columns such as XBridge (trade mark) or SunFire (trade mark) 5 µm materials at room temperature. Mobile phases typically consisted of acetonitrile mixed with water containing either 0.1% formic acid or 0.1% ammonia, unless otherwise stated.
3. Super Critical Fluid Chromatography (SFC)

SFC chiral separations were performed on a Waters prep30/MS system, using a flow rate of 30 mL/min, temperature of 40° C. and a pressure of 100 bar or on a Sepiatec prep 100 system, using a flow rate of 60 mL/min, temperature of 40° C. and pressure of 100 bar. Mobile phases typically consisted of supercritical $CO_2$ and a polar solvent such as methanol, ethanol or isopropanol. Column type and eluent are detailed for individual examples.

'Room temperature', as used in the present specification, means a temperature in the range from about 18° C. to about 25° C.
4. Abbreviations
  AIBN: Azobisisobutyronitrile
  Boc tert-Butyloxycarbonyl
  15-Crown-5 1,4,7,10,13-Pentaoxacyclopentadecane
  18-Crown-6 1,4,7,10,13,16-Hexaoxacyclooctadecane
  DCM: Dichloromethane
  DIPEA: N,N-Diisopropylethylamine
  DMF: Dimethylformamide
  DMSO: Dimethylsulfoxide
  $Et_2O$: diethyl ether
  EtOAc: Ethyl acetate
  EtOH: Ethanol
  HATU: 1-[Bis(dimethylamino)methylene]-1H-1,2,3-triazolo[4,5-b]pyridinium 3-oxid hexafluorophosphate
  HPLC: High-Performance Liquid Chromatography
  mCPBA: meta-Chloroperbenzoic acid
  MeCN: Acetonitrile
  MeOH: Methanol
  NBS: N-Bromosuccinamide
  TBME: tert-Butylmethylether
  TEA: Triethylamine
  THF: Tetrahydrofuran
  T3P: Propylphosphonic anhydride
5. cAMP Assay Compound activities were determined in CHO-CRE-luc cells stably expressing hu/mo mGluR7, using a cAMP reporter gene assay (Steady Glo, Promega). Selectivity was assessed in stable CHO-mGluR4 cells (DiscoverX) and CHO-mGluR8 transients using an HTRF cAMP assay (Cisbio).
6. Impedance Assay Stable CHO-mGluR7 cells (DiscoverX) were pre-incubated with compounds (EC80, 1 h), washed and after 30 min, impedance changes upon addition of a tool mGluR7 activator (CPD A) were determined (Cellkey, Molecular Devices).
7. Glutamate Release Assay Stimulus induced glutamate release from mouse cortical synaptosomes was monitored using a fluorescence based glutamate dehydrogenase assay [3]. Compounds were incubated for 1 or 10 min for the inhibition or potentiation modes respectively.

8. Electrophysiology

Intracellular recordings were made from CA1 pyramidal cells following SC stimulation in mouse hippocampal slices. Compounds were applied to the slices for 10 min, with recordings made over a 45 minutes period. mGluR7 KO mice were obtained from the Toronto Centre for Phenogenomics.

9. Compounds

L-2-amino-4-phosphonobutyric acid (herein "L-AP4") was a non-selective agonist used in the experiments herein. L-AP4 has the IUPAC name (2S)-2-amino-4-phosphonobutanoic acid and the CAS number 23052-81-5.

LY341495 (also herein referred to as "LY") was a orthosteric antagonist used in the experiments herein. LY341495 has the IUPAC name 2-[(1S,2S)-2-carboxycyclopropyl]-3-(9H-xanthen-9-yl)-D-alanine and the CAS number 201943-63-7.

VU0422288 was a positive allosteric modulator (PAM) compound used in the experiments herein. VU0422288 has the IUPAC name N-[3-Chloro-4-[(5-chloro-2-pyridinyl)oxy]phenyl]-2-pyridinecarboxamide and the CAS number 1630936-95-6.

Intermediates

Intermediate A1:
3-amino-3,4-dihydro-2H-1-benzopyran-4-ol hydrochloride

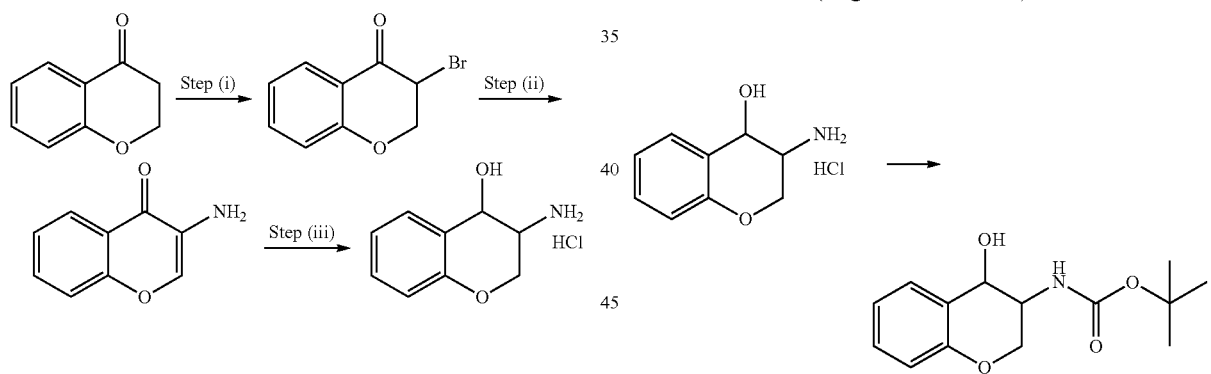

Step (i):
3-bromo-3,4-dihydro-2H-1-benzopyran-4-one

To a stirred solution of CuBr (90.5 g, 405 mmol) in EtOAc (150 mL) was added a solution of 3,4-dihydro-2H-1-benzopyran-4-one (30 g, 202 mmol) in chloroform (150 mL). The reaction was heated to reflux for 18 hours. The reaction was cooled and filtered through diatomaceous earth, washing with EtOAc. The filtrate was concentrated in vacuo to afford the title compound.

$^1$H NMR (400 MHz, CDCl$_3$) δ ppm 4.57-4.75 (m, 3 H), 7.02-7.13 (m, 2 H), 7.51-7.58 (m, 1 H), 7.91-7.98 (m, 1 H)
MS ES$^+$: 224

Step (ii): 3-amino-4H-chromen-4-one

A solution of 3-bromo-3,4-dihydro-2H-1-benzopyran-4-one (46.8 g, 206 mmol) in DMF (450 mL) under N$_2$ was cooled to −10° C. and sodium azide (20.1 g, 309 mmol) was added portion wise. The reaction was warmed to room temperature and stirred for 18 hours. The mixture was partitioned between EtOAc and water. The water was further extracted with EtOAc. The aqueous was basified with 2 M NaOH and extracted with EtOAc. The combined organics were dried (Na$_2$SO$_4$) and concentrated in vacuo. The resulting residue was triturated with Et$_2$O/water, filtered and dried to afford the title compound.

$^1$H NMR (400 MHz, CDCl$_3$) δ ppm 3.65 (br. s., 2 H), 7.33-7.46 (m, 2 H), 7.57-7.65 (m, 1 H), 7.79 (s, 1 H), 8.21-8.30 (m, 1 H)

Step (iii):
3-amino-3,4-dihydro-2H-1-benzopyran-4-ol hydrochloride

A solution of 3-amino-4H-chromen-4-one (15 g, 90 mmol) in EtOH (500 mL) was treated with HCl in EtOH (1.25M, 72 mL, 90 mmol). Pd/C (10% wt/wt, 6.7g, 6.3 mmol) was slurried in EtOH and added to the reaction. The reaction vessel was evacuated and refilled with hydrogen three times and stirred at room temperature for 22 hours. The reaction was filtered through diatomaceous earth, washing with EtOH and the filtrate was concentrated in vacuo to afford the title compound.

$^1$H NMR (400 MHz, DMSO-d$_6$) δ ppm 3.57-3.69 (m, 1 H), 4.10-4.34 (m, 2 H), 6.15-6.43 (m, 1 H), 6.81-6.89 (m, 1 H), 6.96-7.04 (m, 1 H), 7.20-7.28 (m, 1 H), 7.34-7.44 (m, 1 H), 8.31 (br. s., 3 H)

Intermediates A2 and A3: tert-butyl N-(4-hydroxy-3,4-dihydro-2H-1-benzopyran-3-yl)carbamate (single diastereomers)

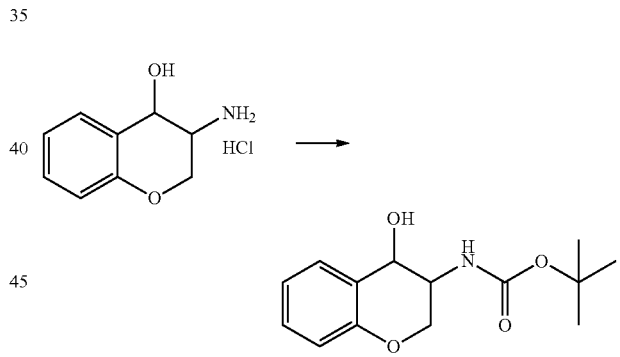

3-Amino-3,4-dihydro-2H-1-benzopyran-4-ol hydrochloride (Intermediate A1, 21.7 g, 90 mmol) in THF (150 mL) was treated with a solution of Na$_2$CO$_3$ (19.1 g, 180 mmol) in water (3 mL). Boc anhydride (21.6 g, 99 mmol) in THF (70 mL) was added and the reaction was stirred at room temperature for 1 hour. The mixture was partitioned between DCM and water. The organic was collected, dried (Na$_2$SO$_4$) and concentrated in vacuo. The crude material was purified by column chromatography on silica, eluted with 0-20% EtOAc/hexane to afford the title compounds.

Intermediate A2—1$^{st}$ Eluting Peak—Racemic cis $^1$H NMR (400 MHz, DMSO-d$_6$) δ ppm 1.41 (s, 9 H), 3.71-3.84 (m, 1 H), 3.92-4.05 (m, 2 H), 4.54-4.64 (m, 1 H), 5.53-5.59 (m, 1 H), 6.28-6.35 (m, 1 H), 6.75-6.82 (m, 1 H), 6.90 (s, 1 H), 7.15-7.22 (m, 1 H), 7.23-7.30 (m, 1 H)
MS ES$^+$: 266

Intermediate A3—2nd Eluting Peak—Racemic trans $^1$H NMR (400 MHz, DMSO-d$_6$) δ ppm 1.39 (s, 9 H), 3.60-3.69 (m, 1 H), 3.88-3.98(m, 1 H), 4.08-4.16 (m, 1 H), 4.39-4.49 (m, 1 H), 5.54-5.64 (m, 1 H), 6.72-6.86 (m, 2 H), 6.88-6.95 (m, 1 H), 7.11-7.21 (m, 1 H), 7.29-7.38 (m, 1 H)
MS ES$^+$: 266

Intermediate A: (cis)-3-amino-3,4-dihydro-2H-1-benzopyran-4-ol hydrochloride

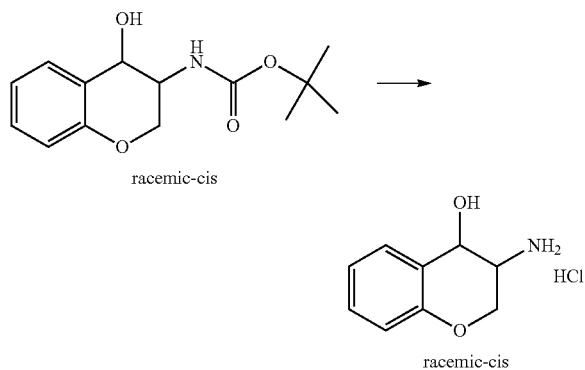

A solution of tert-butyl N-((cis)-4-hydroxy-3,4-dihydro-2H-1-benzopyran-3-yl)carbamate (Intermediate A2, 0.50 g, 1.9 mmol) in MeOH (8 mL) was cooled to 0° C. and treated with HCl (4 N in dioxane, 4.75 mL, 19 mmol) in a dropwise fashion. The reaction was allowed to warm to room temperature for 2.5 hours. The reaction was concentrated in vacuo and the resulting residue was triturated with TBME, filtered and dried to afford the title compound.

$^1$H NMR (400 MHz, DMSO-d$_6$) δ 3.58-3.66 (m, 1 H), 4.09-4.20 (m, 1 H), 4.25-4.34 (m, 1 H), 4.79-4.88 (m, 1 H), 6.42 (br. s., 1 H), 6.77-6.87 (m, 1 H), 6.92-7.02 (m, 1 H), 7.18-7.28 (m, 1 H), 7.34-7.43 (m, 1 H), 8.46 (br. s., 3 H)
MS ES$^+$: 166

Intermediate B: (trans)-3-amino-3,4-dihydro-2H-1-benzopyran-4-ol hydrochloride

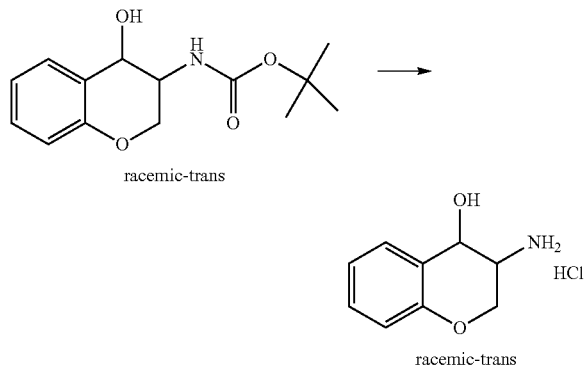

Prepared as described for (cis)-3-amino-3,4-dihydro-2H-1-benzopyran-4-ol hydrochloride (Intermediate A) using tert-butyl N-((trans)-4-hydroxy-3,4-dihydro-2H-1-benzopyran-3-yl)carbamate (Intermediate A3, 0.50 g, 1.9 mmol). The crude material was purified by trituration with TBME to afford the title compound.

$^1$H NMR (400 MHz, DMSO-d$_6$) δ 3.53-4.03 (m, 1 H), 4.10-4.42 (m, 2 H), 4.61-4.86 (m, 1 H), 5.33-6.71 (m, 1 H), 6.71-7.05 (m, 2 H), 7.14-7.30 (m, 1 H), 7.32-7.51 (m, 1 H), 8.65 (br. s., 3 H)
MS ES$^+$: 166

Intermediate C: 3-amino-6-fluoro-3,4-dihydro-2H-1-benzopyran-4-ol

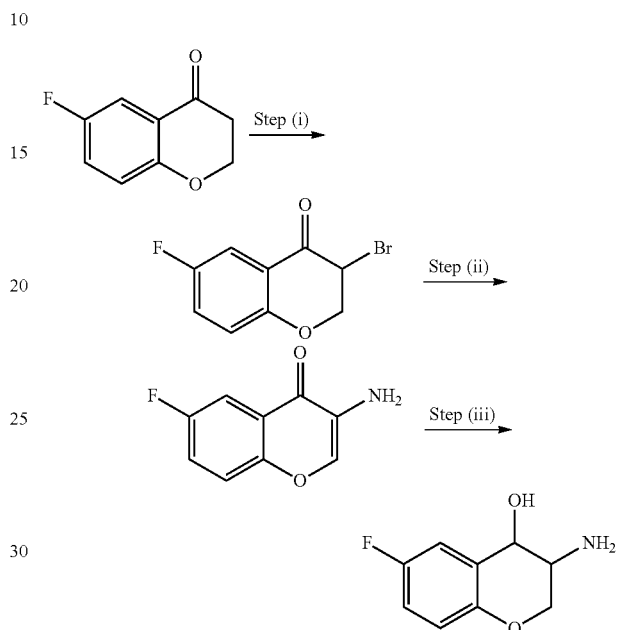

Step (i): 3-bromo-6-fluoro-3,4-dihydro-2H-1-benzopyran-4-one

Cupric bromide (40.3 g, 180.4 mmol) in EtOAc (75 mL) was heated to reflux. A solution of 6-fluoro-3,4-dihydro-2H-1-benzopyran-4-one (15 g, 90 mmol) in chloroform (75 mL) was added dropwise to the hot cupric bromide solution and then stirred at reflux overnight. The mixture was allowed to cool to room temperature, filtered through a pad of diatomaceous earth, washing with EtOAc and concentrated in vacuo to afford the title compound.
ES$^+$=245

Step (ii): 3-amino-6-fluoro-4H-chromen-4-one

A solution of 3-bromo-6-fluoro-3,4-dihydro-2H-1-benzopyran-4-one (15 g, 61.2 mmol) in DMF (160 mL) was cooled to 0° C. and treated with sodium azide (5.97 g, 91.8 mmol) in portions over 20 minutes. After addition was complete, the mixture was stirred at 0° C. for 3 hours. The reaction mixture was poured into water and the resultant precipitate was collected by filtration, washing with diethyl ether to afford the title compound.

$^1$H NMR (400 MHz, DMSO-d$_6$) δ ppm 4.62 (br. s, 2 H), 7.50-7.80 (m, 3 H), 8.00 (s, 1 H)
ES$^+$=180

Step (iii): 3-amino-6-fluoro-3,4-dihydro-2H-1-benzopyran-4-ol

A mixture of 3-amino-6-fluoro-4H-chromen-4-one (4 g, 22.3 mmol) and Pd/C (10% wt/wt, 400 mg, 0.38 mmol) in EtOH (200 mL) was treated with HCl in EtOH (1.25 M, 20 mL, 25 mmol). The reaction vessel was evacuated and refilled with hydrogen and stirred at room temperature for 1 hour. Further HCl in EtOH (1.25 M, 20 mL, 25 mmol) was added to the reaction. The reaction was stirred at room temperature for 2 hours. A further portion of Pd/C (10% wt/wt, 400 mg, 0.38 mmol) was added to the reaction. The reaction was stirred at room temperature for a further 4 days. The reaction was filtered through diatomaceous earth, washing with DCM and the filtrate was concentrated in vacuo. Water was added to the residue and the pH was adjusted to approximately 9 with saturated aq. NaHCO$_3$. The mixture was washed with diethyl ether and concentrated in vacuo. The residue was suspended in DCM, filtered and the filtrate concentrated in vacuo then purified by column chromatography on silica, eluted with 0-10% methanol/DCM to afford the title compound.

ES$^+$=184

Intermediate D: (2S)—N-[(trans)-4-(methylsulfanyl)-3,4-dihydro-2H-1-benzopyran-3-yl]-2-phenylpropanamide

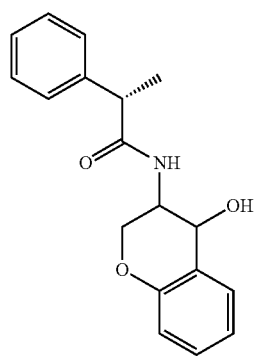

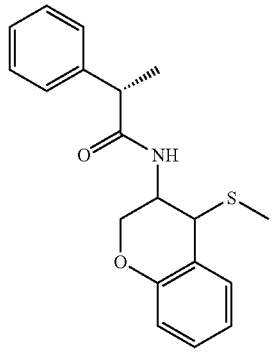

Methanesulfonic anhydride (117 mg, 0.673 mmol) as a solution in THF (1 mL) was added to a solution of (2S)—N-((cis)-4-hydroxy-3,4-dihydro-2H-1-benzopyran-3-yl)-2-phenylpropanamide (Example 1, 100 mg, 0.336 mmol) and TEA (0.136 mL, 1.009 mmol) in THF (2 mL) under nitrogen. The reaction was warmed to 0° C. and stirred for 30 minutes. Sodium methanethiolate (118 mg, 1.682 mmol) and 15-crown-5 (74 mg, 0.336 mmol) were added and the reaction was allowed to warm to room temperature for 18 hours. The reaction mixture was partitioned between EtOAc and water. The organics were collected, dried (phase separator) and concentrated in vacuo to afford the title compound.

MS ES$^-$: 326

Intermediate E1: ethyl 2-bromo-2-[2-(2-ethoxy-2-oxoethyl)phenyl]acetate

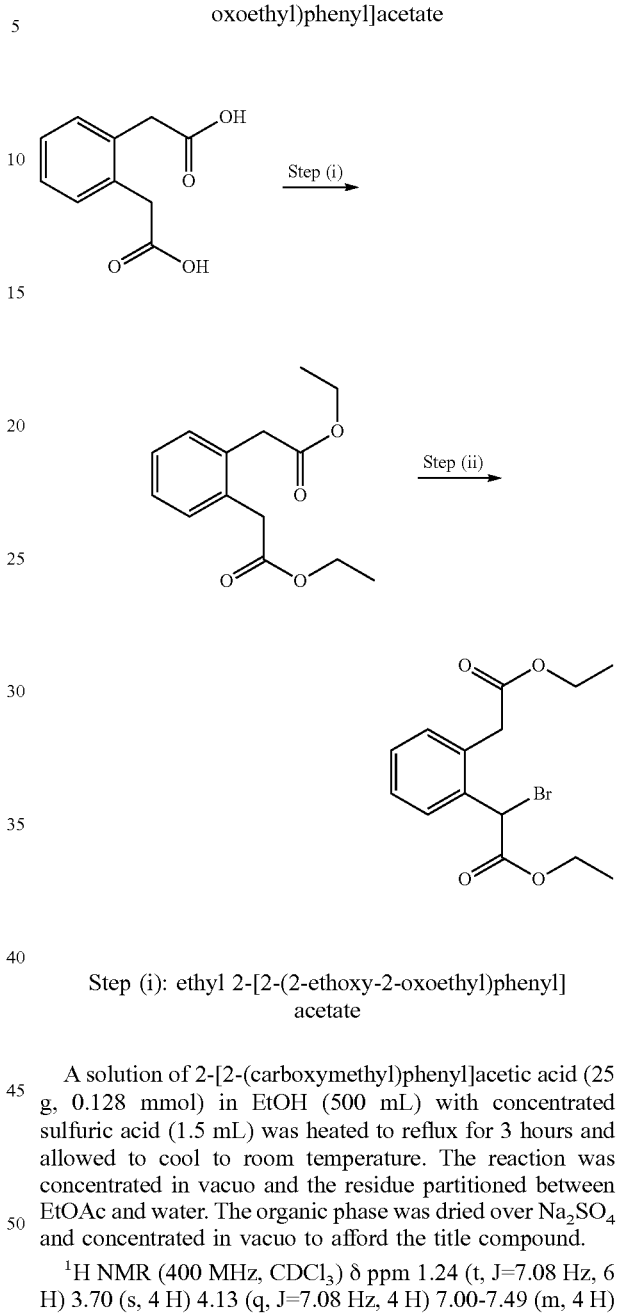

Step (i): ethyl 2-[2-(2-ethoxy-2-oxoethyl)phenyl]acetate

A solution of 2-[2-(carboxymethyl)phenyl]acetic acid (25 g, 0.128 mmol) in EtOH (500 mL) with concentrated sulfuric acid (1.5 mL) was heated to reflux for 3 hours and allowed to cool to room temperature. The reaction was concentrated in vacuo and the residue partitioned between EtOAc and water. The organic phase was dried over Na$_2$SO$_4$ and concentrated in vacuo to afford the title compound.

$^1$H NMR (400 MHz, CDCl$_3$) δ ppm 1.24 (t, J=7.08 Hz, 6 H) 3.70 (s, 4 H) 4.13 (q, J=7.08 Hz, 4 H) 7.00-7.49 (m, 4 H)

Step (ii): ethyl 2-bromo-2-[2-(2-ethoxy-2-oxoethyl)phenyl]acetate

NBS (0.712 g, 4 mmol) was added to a solution of ethyl 2-[2-(2-ethoxy-2-oxoethyl)phenyl]acetate (1.00 g, 4 mmol) in CCl$_4$ (15 mL). AIBN (66 mg, 0.4 mmol) was added and the reaction heated to 60° C. for 18 hours. After cooling to room temperature, the reaction mixture was filtered and the filtrate concentrated in vacuo to afford the title compound.

$^1$H NMR (400 MHz, CDCl$_3$) δ ppm 1.03-1.35 (m, 6 H) 3.44-3.81 (m, 2 H) 4.00-4.38 (m, 4 H) 5.52-5.86 (m, 1 H) 7.02-7.86 (m, 4 H)

Intermediate E2: 2-(cyclopropylmethyl)-3-oxo-1,2,3,4-tetrahydroisoquinoline-1-carboxylic acid

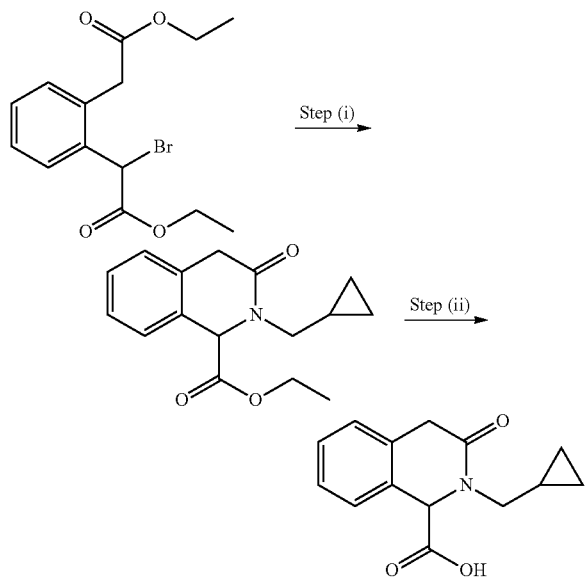

Step (i): ethyl 2-(cyclopropylmethyl)-3-oxo-1,2,3,4-tetrahydroisoquinoline-1-carboxylate Ethyl 2-bromo-2-[2-(2-ethoxy-2-oxoethyl)phenyl]acetate (Intermediate E1, 8.5 g, 25.9 mmol), $K_2CO_3$ (17.0 g, 51.8 mmol), (aminomethyl)cyclopropane (2.6 g, 36.48 mmol) and DMF (65 mL) were combined in a tube, sealed and heated to 100° C. for 18 hours. The reaction mixture was allowed to cool to room temperature, filtered and the filtrate concentrated in vacuo. The residue was purified by column chromatography on silica, eluted with 0-20% EtOAc/toluene to afford the title compound.

$^1$H NMR (400 MHz, $CDCl_3$) δ ppm 0.19-0.34 (m, 2 H), 0.43-0.62 (m, 2 H), 0.90-1.05 (m, 1 H), 1.23 (t, J=7.22 Hz, 3 H), 3.22-3.34 (m, 1 H), 3.53-3.67 (m, 2 H), 3.84-3.95 (m, 1 H), 4.05-4.24 (m, 2 H), 5.17 (s, 1 H), 7.14-7.21 (m, 1 H), 7.25-7.35 (m, 2 H), 7.38-7.46 (m, 1 H)

MS ES$^+$: 274

Step (ii): 2-(cyclopropylmethyl)-3-oxo-1,2,3,4-tetrahydroisoquinoline-1-carboxylic acid LiOH.$H_2O$ (0.65 g, 16.1 mmol) was added to a solution of ethyl 2-(cyclopropylmethyl)-3-oxo-1,2,3,4-tetrahydroisoquinoline-1-carboxylate (4.82 g, 14.0 mmol) in THF (75 mL) and water (25 mL) and stirred for 18 hours. The reaction was concentrated in vacuo. Aqueous HCl was added to pH 7 and the resulting solid filtered, azeotroped with toluene and dried in vacuo to afford the title compound.

$^1$H NMR (400 MHz, DMSO-$d_6$) δ ppm 0.05-0.50 (m, 4 H) 0.86-1.02 (m, 1 H) 2.63-2.79 (m, 1 H) 3.12-3.31 (m, 2 H) 3.63-3.85 (m, 2 H) 4.78 (s, 1 H) 7.02-7.19 (m, 3 H) 7.33-7.43 (m, 1 H)

ES$^-$: 244

Intermediates E3 and E4: (1S)-1-[(4S)-4-benzyl-2-oxo-1,3-oxazolidine-3-carbonyl]-2-(cyclopropylmethyl)-1,2,3,4-tetrahydroisoquinolin-3-one and (1R)-1-[(4S)-4-benzyl-2-oxo-1,3-oxazolidine-3-carbonyl]-2-(cyclopropylmethyl)-1,2,3,4-tetrahydroisoquinolin-3-one

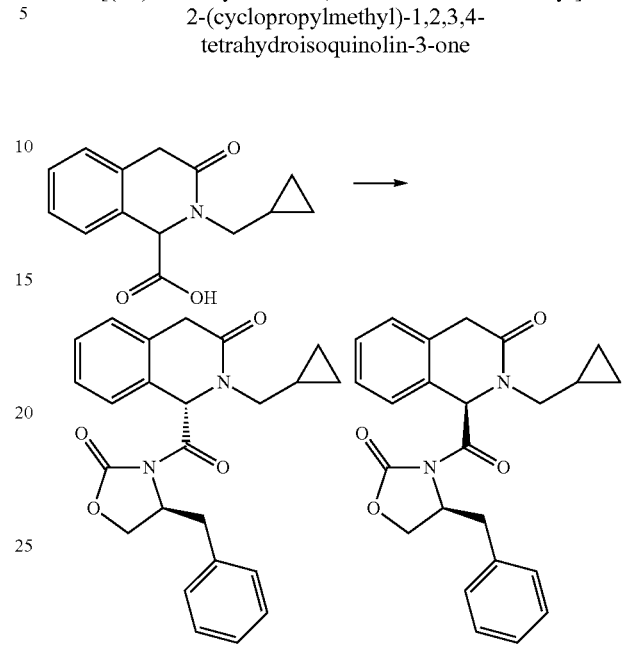

A solution of 2-(cyclopropylmethyl)-3-oxo-1,2,3,4-tetrahydroisoquinoline-1-carboxylic acid (Intermediate E2, 16.7 g, 58.2 mmol) in THF (500 mL) at −10° C. was treated with TEA (9.73 mL, 69.8 mmol) followed by pivolyl chloride (7.53 mL, 61.1 mmol) in a dropwise fashion. The reaction was stirred at −10° C. for 1 hour. In a separate flask, a solution of (4S)-4-benzyl-1,3-oxazolidin-2-one (10.32 g, 58.2 mmol) in THF (100 mL) was cooled to −78° C. and treated with n-butyllithium (2.5 M in hexanes, 24.5 mL, 61.1 mmol) in a dropwise fashion. The reaction was stirred at −78° C. for 20 min. The solution was cannulated into the previously reacted solution of acid, TEA and pivolyl chloride at −78° C. and the reaction was allowed to warm to room temperature over 18 hours. The reaction was quenched with $NH_4Cl$ solution and extracted with EtOAc. The organic was collected, washed with 2 M HCl, $NaHCO_3$ solution and brine, dried ($Na_2SO_4$) and concentrated in vacuo. The resulting residue was purified by column chromatography on silica, eluted with 17-33% EtOAc/hexanes to afford the title compounds.

Intermediate E3—First Eluting Diastereomer (1S)-1-[(4S)-4-benzyl-2-oxo-1,3-oxazolidine-3-carbonyl]-2-(cyclopropylmethyl)-1,2,3,4-tetrahydroisoquinolin-3-one $^1$H NMR (400 MHz, $CDCl_3$) δ ppm 0.22-0.41 (m, 2 H), 0.44-0.64 (m, 2 H), 0.93-1.07 (m, 1 H), 2.62-2.76 (m, 1 H), 2.95-3.05 (m, 1 H), 3.39-3.50 (m, 1 H), 3.64 (d, J=19.30 Hz, 1 H), 3.89-4.00 (m, 1 H), 4.06-4.18 (m, 2 H), 4.19-4.28 (m, 1 H), 4.42-4.53 (m, 1 H), 6.85 (s, 1 H), 7.17-7.26 (m, 4 H), 7.28-7.37 (m, 4 H), 7.53-7.61 (m, 1 H)

MS ES$^+$: 405

Intermediate E4—Second Eluting Diastereomer (1R)-1-[(4S)-4-benzyl-2-oxo-1,3-oxazolidine-3-carbonyl]-2-(cyclopropylmethyl)-1,2,3,4-tetrahydroisoquinolin-3-one $^1$H NMR (400 MHz, CDCl$_3$) δ ppm 0.15-0.32 (m, 2 H), 0.35-0.45 (m, 1 H), 0.48-0.59 (m, 1 H), 0.83-1.00 (m, 1 H), 2.59-2.70 (m, 1 H), 2.75-2.83 (m, 1 H), 2.89-3.02 (m, 1 H), 3.61 (d, J=19.35 Hz, 1 H), 3.81-3.91 (m, 1 H), 4.05 (d, J=19.62 Hz, 1 H), 4.18-4.25 (m, 1 H), 4.29-4.41 (m, 1 H), 4.69-4.81 (m, 1 H), 6.73-6.84 (m, 3 H), 7.05-7.23 (m, 4 H), 7.26-7.38 (m, 2 H), 7.66-7.76 (m, 1 H)

MS ES$^+$: 405

Intermediate E5: (1S)-2-(cyclopropylmethyl)-3-oxo-1,2,3,4-tetrahydroisoquinoline-1-carboxylic acid (single enantiomer)

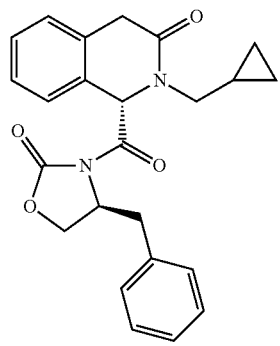

To a stirring solution of (1S)-1-[(4S)-4-benzyl-2-oxo-1,3-oxazolidine-3-carbonyl]-2-(cyclopropylmethyl)-1,2,3,4-tetrahydroisoquinolin-3-one (Intermediate E3 5.00 g, 12.37 mmol) in THF (90 mL) and water (30 mL) at 0° C. was added LiOH.H$_2$O (1.04 g, 24.8 mmol) followed by H$_2$O$_2$ (30% in H$_2$O, 11.22 g, 100.0 mmol) in a portionwise fashion. The reaction was stirred at 0° C. for 2 hours and allowed to warm to room temperature over 18 hours. Sodium thiosulfate solution was added carefully and the pH was adjusted to pH 4-5 with aqueous HCl. The aqueous was extracted with EtOAc, dried (Na$_2$SO$_4$) and concentrated in vacuo. The resulting residue was triturated with DCM to afford the title compound.

$^1$H NMR (400 MHz, DMSO-d$_6$) δ ppm 0.17-0.29 (m, 2 H), 0.33-0.50 (m, 2 H), 0.88-1.00 (m, 1 H), 3.15-3.25 (m, 2 H), 3.48 (d, J=19.07 Hz, 1 H), 3.65 (d, J=19.35 Hz, 1 H), 5.33 (s, 1 H), 7.20-7.35 (m, 3 H), 7.42-7.48 (m, 1 H)

MS ES$^+$: 246

Intermediate E: (1S)-2-(cyclopropylmethyl)-N-((trans)-4-hydroxy-3,4-dihydro-2H-1-benzopyran-3-yl)-3-oxo-1,2,3,4-tetrahydroisoquinoline-1-carboxamide (example 40)

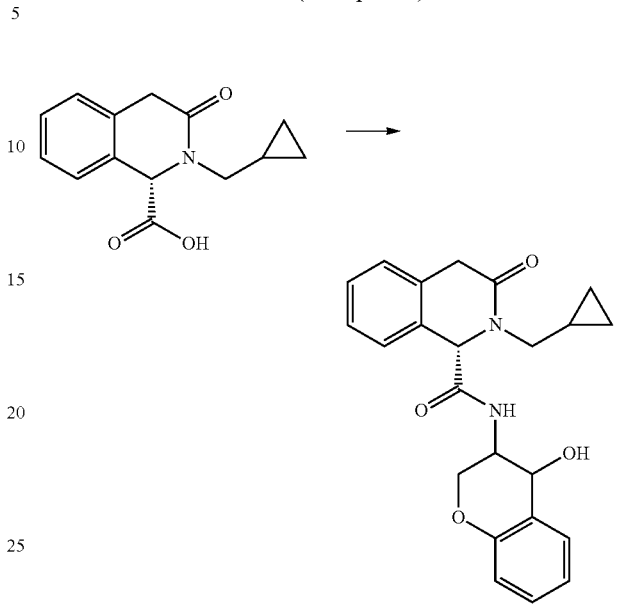

HATU (186 mg, 0.489 mmol) was added to a stirred solution of (1S)-2-(cyclopropyl-methyl)-3-oxo-1,2,3,4-tetrahydroisoquinoline-1-carboxylic acid (Intermediate E5, 100 mg, 0.408 mmol), (trans)-3-amino-3,4-dihydro-2H-1-benzopyran-4-ol hydrochloride (Intermediate B, 67.3 mg, 0.408 mmol) and DIPEA (0.142 mL, 0.815 mmol) in DCM (2 mL) and stirred for 1 hour. The reaction was washed with water, dried (phase separator) and concentrated in vacuo. The resulting residue was purified by column chromatography on silica, eluted with 0-100% ethyl acetate/petroleum ether to afford the title compound.

$^1$H NMR (400 MHz, DMSO-d$_6$) δ ppm 0.00-0.52 (m, 4 H), 0.66-0.97 (m, 1 H), 3.07-3.28 (m, 2 H), 3.35-3.50 (m, 1 H), 3.73-3.98 (m, 3 H), 4.08-4.50 (m, 3 H), 5.56-5.80 (m, 1 H), 6.81-7.55 (m, 8 H), 8.48-8.65 (m, 1 H)

MS ES$^+$: 393

Intermediate F1: (2S)-2-(4-fluorophenyl)propanoic acid

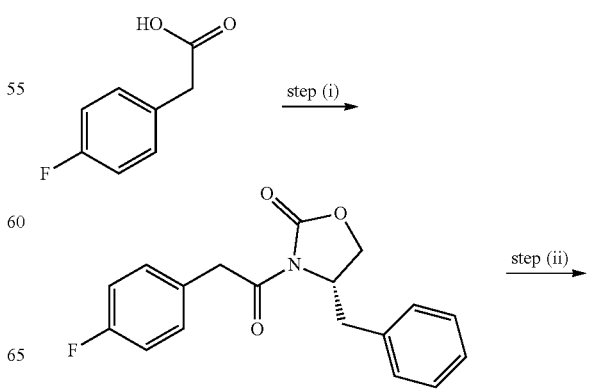

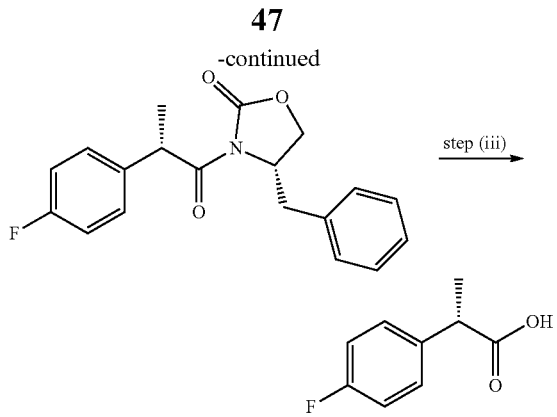

Step (i): (S)-4-benzyl-3-(2-(4-fluorophenyl)acetyl)oxazolidin-2-one n-Butyllithium (2.5 M solution in hexanes, 34.75 mL, 87 mmol) was added slowly to a solution of (S)-4-benzyloxazolidin-2-one (14.0 g, 79.09 mmol) in THF (280 mL) under nitrogen at −70° C. The mixture was stirred at −70° C. for 30 minutes. Meanwhile, TEA (20 g, 197.51 mmol) was added to a solution of 2-(4-fluorophenyl)acetic acid (13.4 g, 86.9 mmol) in THF (280 mL) at 0° C. and stirred for 30 minutes. Pivaloyl chloride (18.96 g, 158.01 mmol) was added dropwise over 30 minutes at 0° C. and then stirred for 1 hour at 0° C. The benzyloxazolidinone solution was then transferred by cannula to the previously prepared anhydride solution at −70° C. and stirred for 30 minutes at −70° C. The mixture was quenched with saturated NH$_4$Cl solution, diluted with water and extracted with EtOAc. The combined organics were washed with brine, dried (Na$_2$SO$_4$) and concentrated in vacuo. The crude product was purified by column chromatography on silica, eluted with 0-7% ethyl acetate/hexane to afford the title compound.

$^1$H NMR (400 MHz, DMSO-d$_6$) δ ppm 2.85-3.03 (m, 2 H) 4.09-4.29 (m, 3 H) 4.31-4.39 (m, 1 H) 4.62-4.70 (m, 1 H) 7.09-7.21 (m, 4 H) 7.22-7.36 (m, 5 H)

MS ES$^+$: 314

Step (ii): (S)-4-benzyl-3-((S)-2-(4-fluorophenyl)propanoyl)oxazolidin-2-one

Sodium bis(trimethylsilyl)amide (1M solution in THF, 62.3 mL, 62.30 mmol) was added slowly to a solution of (S)-4-benzyl-3-(2-(4-fluorophenyl)acetyl)oxazolidin-2-one (13 g, 41.53 mmol) in THF (180 mL) at −70° C. and stirred for 1 hour. Methyl iodide (29.50 g, 207.60 mmol) was then added at −70° C., the mixture was allowed to warm to 0° C. and stirred for 30 minutes. The mixture was quenched with saturated NH$_4$Cl solution, diluted with water and extracted with EtOAc. The combined organics were washed with brine, dried (Na$_2$SO$_4$) and concentrated in vacuo. The crude product was purified by column chromatography on silica, eluted with 0-4% ethyl acetate/hexane to afford the title compound. $^1$H NMR (400 MHz, DMSO-d$_6$) δ ppm 1.44 (d, J=7.09 Hz, 3 H) 2.93-3.07 (m, 2 H) 4.16-4.23 (m, 1 H) 4.24-4.32 (m, 1 H) 4.62-4.69 (m, 1 H) 4.93-5.01 (m, 1 H) 7.09-7.18 (m, 2 H) 7.19-7.38 (m, 7 H)

MS ES$^+$: 328

Step (iii): (2S)-2-(4-fluorophenyl)propanoic acid

Lithium hydroxide (2.15 g, 51.98 mmol) was added to a solution of (S)-4-benzyl-3-((S)-2-(4-fluorophenyl)propanoyl)oxazolidin-2-one (8.5 g, 25.99 mmol) in THF (360 mL) and water (120 mL). Hydrogen peroxide (24 mL, 207.9 mmol) was then added slowly at 0° C. and stirred for 3 hours at 0° C. The mixture was quenched with saturated sodium thiosulfate solution, diluted with water and extracted with ethyl acetate. The aqueous phase was acidified with glacial acetic acid to pH 5 then extracted with ethyl acetate. The residue was lyophilized from acetonitrile to afford the title compound.

$^1$H NMR (400 MHz, DMSO-d$_6$) δ ppm 1.34 (d, J=7.02 Hz, 3 H) 3.69 (q, J=7.02 Hz, 1 H) 7.10-7.19 (m, 2 H) 7.28-7.36 (m, 2 H) 12.37 (br. s., 1 H)

Intermediate F2: (2S)-2-(4-fluorophenyl)-N-((cis)-4-hydroxy-3,4-dihydro-2H-1-benzopyran-3-yl)propanamide (example 41)

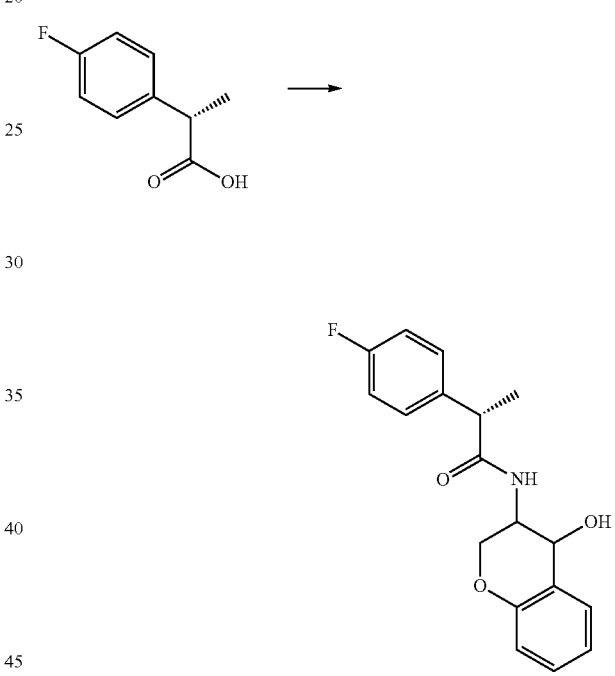

HATU (713 mg, 1.874 mmol) was added to a solution of (cis)-3-amino-3,4-dihydro-2H-1-benzopyran-4-ol hydrochloride (Intermediate A, 258 mg, 1.562 mmol), (2S)-2-(4-fluorophenyl)propanoic acid (Intermediate F1, 263 mg, 1.562 mmol) and DIPEA (0.546 mL, 3.12 mmol) in DCM (10 mL). The reaction was stirred at room temperature for 1.5 hours. Saturated NaHCO$_3$ was added to the mixture. The phases were separated and the aqueous extracted with DCM. The combined organics were dried (phase separator) and concentrated in vacuo. The crude product was purified by reverse phase chromatography on C18 silica eluted with 5-95% methanol/water (with 0.1% ammonia) to afford the title compound.

$^1$H NMR (400 MHz, CD$_2$Cl$_2$) δ ppm 1.35-1.51 (m, 4 H), 3.51-3.61 (m, 1 H), 3.80-3.98 (m, 1 H), 4.03-4.19 (m, 1 H), 4.29-4.42 (m, 1 H), 4.64-4.77 (m, 1 H), 5.99-6.09 (m, 1 H), 6.78-6.87 (m, 1 H), 6.90-6.98 (m, 1 H), 6.98-7.07 (m, 2 H), 7.20-7.34 (m, 4 H)

MS ES$^+$: 314

Intermediate F: (2S)-2-(4-fluorophenyl)-N-[(trans)-4-(methylsulfanyl)-3,4-dihydro-2H-1-benzopyran-3-yl]propanamide

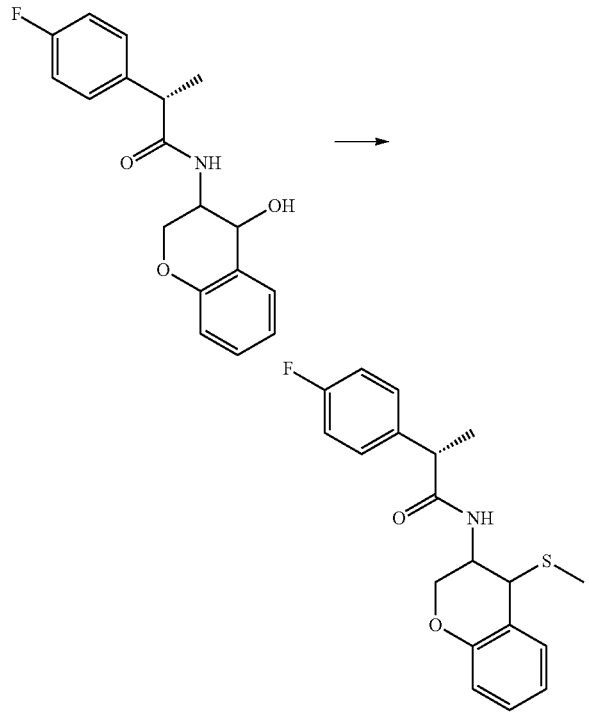

A solution of methanesulfonic anhydride (345 mg, 1.979 mmol) in THF (2 mL) was added dropwise to a solution of (2S)-2-(4-fluorophenyl)-N-((cis)-4-hydroxy-3,4-dihydro-2H-1-benzopyran-3-yl)propanamide (Intermediate F2, 312 mg, 0.989 mmol) and TEA (0.414 ml, 2.97 mmol) in THF (2 mL) at −78° C. under nitrogen. The reaction was stirred at −78° C. for 10 minutes and then −5° C. for 45 minutes. A suspension of sodium methanethiolate (347 mg, 4.95 mmol) and 15-crown-5 (0.979 mL, 4.95 mmol) in THF (2 mL) was added. The reaction was stirred at −5° C. for 1 hour. Further sodium methanethiolate (139 mg, 1.979 mmol) and 15-crown-5 (0.392 mL, 1.979 mmol) were added to the reaction mixture. The reaction was stirred at −5° C. for 30 minutes, then allowed to warm to room temperature and stirred for 18 hours. The mixture was partitioned between EtOAc and water. The phases were separated and the aqueous extracted with EtOAc. The combined organics were dried (phase separator) and concentrated in vacuo to afford the title compound.

MS ES−: 344

Intermediate G1: (2S)-2-(4-chlorophenyl)propanoic acid

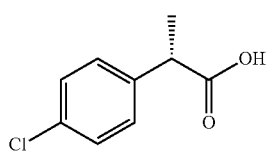

Prepared as described for (2S)-2-(4-fluorophenyl)propanoic acid (Intermediate F1) using 2-(4-chlorophenyl)acetic acid (15.40 g, 90 mmol) and (S)-4-benzyloxazolidin-2-one (8 g, 45.1 mmol).

$^1$H NMR (400 MHz, CD$_2$Cl$_2$) δ ppm 1.49 (d, J=7.15 Hz, 3 H), 3.74 (q, J=7.21 Hz, 1 H), 7.22-7.35 (m, 4 H)

MS ES−: 183

Intermediate G: (2S)-2-(4-chlorophenyl)-N-[(trans)-4-(methylsulfanyl)-3,4-dihydro-2H-1-benzopyran-3-yl]propanamide

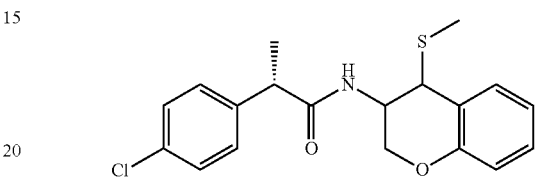

Prepared as described for (2S)-2-(4-fluorophenyl)-N-[(trans)-4-(methylsulfanyl)-3,4-dihydro-2H-1-benzopyran-3-yl]propanamide (Intermediate F) using (cis)-3-amino-3,4-dihydro-2H-1-benzopyran-4-ol hydrochloride (Intermediate A, 172 mg, 1.041 mmol) and (2S)-2-(4-chlorophenyl)propanoic acid (Intermediate G1, 192 mg, 1.041 mmol) to afford the title compound.

MS ES−: 360

Intermediates H and I: (2S)-2-(4-fluorophenyl)-N-((cis)-4-hydroxy-3,4-dihydro-2H-1-benzopyran-3-yl)propanamide (single stereoisomers)

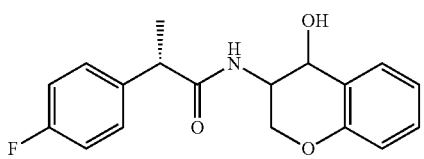 [SMILES: C[C@H](C(=O)NC1COc2ccccc2C1O)c1ccc(F)cc1]

(2S)-2-(4-fluorophenyl)-N-((cis)-4-hydroxy-3,4-dihydro-2H-1-benzopyran-3-yl)propanamide Intermediate F2 was purified by column chromatography on silica, eluted with 0-50% ethyl acetate/petroleum ether to afford the title compounds.

Intermediate H—First Eluting Stereoisomer $^1$H NMR (400 MHz, DMSO-d$_6$) δ ppm 1.33 (d, J=7.06 Hz, 3 H), 3.83-3.92 (m, 1 H), 3.96-4.13 (m, 3 H), 4.41-4.51 (m, 1 H), 5.62-5.71 (m, 1 H), 6.80 (d, J=8.16 Hz, 1 H), 6.85-6.93 (m, 1 H), 7.08-7.27 (m, 4 H), 7.36-7.43 (m, 2 H), 7.80 (d, J=7.43 Hz, 1 H)

Intermediate I—Second Eluting Stereoisomer $^1$H NMR (400 MHz, DMSO-d$_6$) δ ppm 1.34 (d, J=7.15 Hz, 3 H), 3.80-3.95 (m, 3 H), 4.02-4.16 (m, 1 H), 4.54-4.64 (m, 1 H), 5.64-5.72 (m, 1 H), 6.74-6.81 (m, 1 H), 6.87-6.97 (m, 1 H), 7.08-7.23 (m, 3 H), 7.26-7.31 (m, 1 H), 7.34-7.42 (m, 2 H), 7.82 (d, J=7.52 Hz, 1 H)

Intermediate J1: ethyl 2-bromo-2-(4-fluorophenyl)acetate

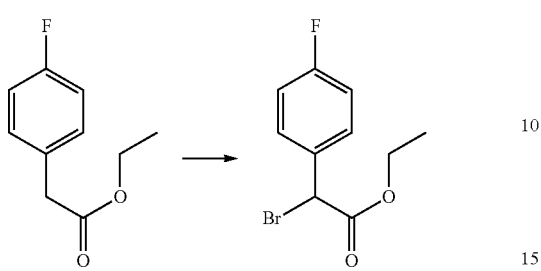

1,1'-Azobis(cyclohexanecarbonitrile) (2.012 g, 8.23 mmol) was added to a suspension of NBS (14.80 g, 83 mmol) and ethyl 2-(4-fluorophenyl)acetate (15 g, 82 mmol) in chlorobenzene (350 mL) under nitrogen. The reaction was stirred at 70° C. for 18 hours. The mixture was partitioned between DCM and water. The phases were separated and the aqueous extracted with DCM. The combined organics were washed with water followed by brine, dried (phase separator) and concentrated in vacuo. The crude product was purified by column chromatography on silica, eluted with 0-5% ethyl acetate/petroleum ether to afford the title compound.

$^1$H NMR (400 MHz, CD$_2$Cl$_2$) δ ppm 1.27 (t, J=7.06 Hz, 3 H) 4.15-4.29 (m, 2 H) 5.37 (s, 1 H) 7.07 (t, J=8.67 Hz, 2 H) 7.49-7.62 (m, 2 H)

Intermediate J: lithio 2-(4-fluorophenyl)-2-[3-(trifluoromethoxy)azetidin-1-yl]acetate

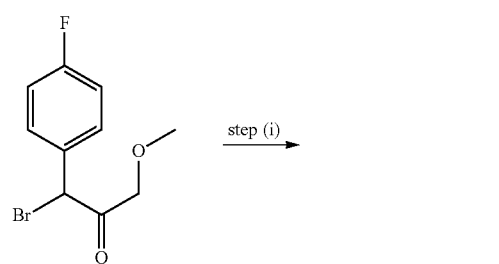

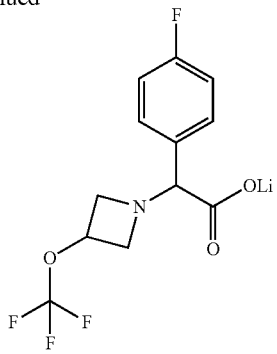

Step (i): ethyl 2-(4-fluorophenyl)-2-[3-(trifluoromethoxy)azetidin-1-yl]acetate Caesium carbonate (0.505 g, 1.549 mmol) was added to a solution of ethyl 2-bromo-2-(4-fluorophenyl)acetate (0.184 g, 0.704 mmol) and 3-(trifluoromethoxy)azetidine hydrochloride (0.125 g, 0.704 mmol) in DMF (2 mL) under nitrogen. The reaction was stirred at room temperature for 18 hours. The mixture was partitioned between DCM and water. The phases were separated, dried (phase separator) and concentrated in vacuo. The crude product was purified by column chromatography on silica, eluted with 0-20% ethyl acetate/petroleum ether to afford the title compound.

$^1$H NMR (400 MHz, CD$_2$Cl$_2$) δ ppm 1.21 (t, J=7.15 Hz, 3 H), 3.13-3.20 (m, 1 H), 3.26-3.36 (m, 1 H), 3.48-3.60 (m, 1 H), 3.85-3.95 (m, 1 H), 4.07-4.23 (m, 3 H), 4.80-4.94 (m, 1 H), 7.03-7.16 (m, 2 H), 7.35-7.46 (m, 2 H)

Step (ii): lithio 2-(4-fluorophenyl)-2-[3-(trifluoromethoxy)azetidin-1-yl]acetate Lithium hydroxide (1M aq, 0.374 mL, 0.374 mmol) was added to a solution of ethyl 2-(4-fluorophenyl)-2-[3-(trifluoromethoxy)azetidin-1-yl]acetate (60 mg, 0.187 mmol) in THF (0.5 mL). The reaction was stirred at room temperature for 24 hours. Further THF (0.5 mL) and lithium hydroxide (0.374 mL, 0.374 mmol) were added and the reaction was stirred at room temperature for a further 2 hours. The reaction was concentrated in vacuo to afford the title compound.

MS ES$^+$: 294

Intermediate K1: ethyl 2-bromo-2-(2,4-difluorophenyl)acetate

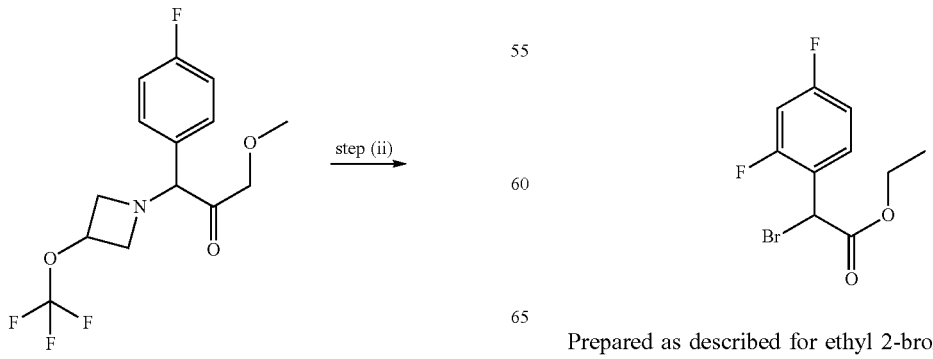

Prepared as described for ethyl 2-bromo-2-(4-fluorophenyl)acetate (Intermediate J1) using ethyl 2-(2,4-difluorophenyl)acetate (12.46 g, 62.2 mmol). The crude product was purified by column chromatography on silica, eluted with 0-5% ethyl acetate/petroleum ether to afford the title compound.

$^1$H NMR (400 MHz, DMSO-d$_6$) δ ppm 1.18 (t, J=7.15 Hz, 3 H) 4.20 (q, J=7.15 Hz, 2 H) 6.13 (s, 1 H) 7.11-7.18 (m, 1 H) 7.28-7.36 (m, 1 H) 7.60-7.70 (m, 1 H)

Intermediate K: lithio 2-(2,4-difluorophenyl)-2-[3-(trifluoromethoxy)azetidin-1-yl]acetate

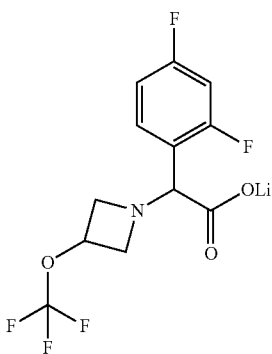

Prepared as described for lithio 2-(4-fluorophenyl)-2-[3-(trifluoromethoxy)azetidin-1-yl]acetate Intermediate J using ethyl 2-bromo-2-(2,4-difluorophenyl)acetate (Intermediate K1, 0.196 g, 0.704 mmol) and 3-(trifluoromethoxy)azetidine hydrochloride (125 mg, 0.704 mmol) to afford the title compound.

MS ES$^+$: 312

Intermediate L1: 2-(3-fluoropropyl)-3-oxo-1,2,3,4-tetrahydroisoquinoline-1-carboxylic acid

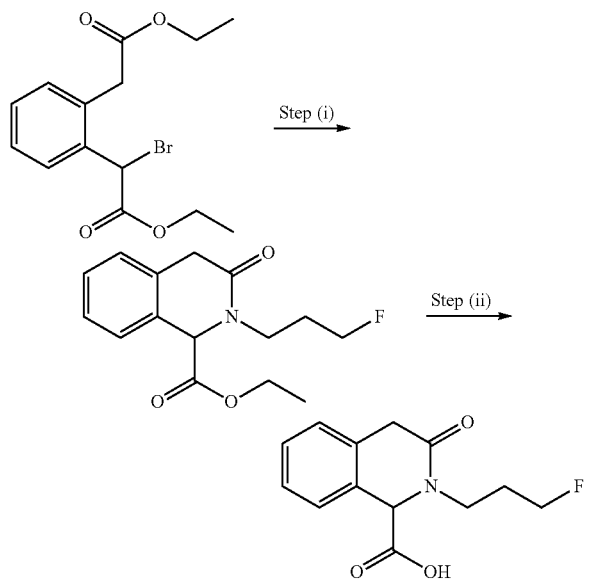

Step (i): ethyl 2-(3-fluoropropyl)-3-oxo-1,2,3,4-tetrahydroisoquinoline-1-carboxylate ethyl 2-bromo-2-[2-(2-ethoxy-2-oxoethyl)phenyl]acetate (Intermediate E1, 13.36 g, 41.3 mmol), K$_2$CO$_3$ (19.0 g, 57.82 mmol), 3-fluoropropan-1-amine hydrochloride (4.7 g, 41.3 mmol) and DMF (100 mL) were combined in a tube, sealed and heated to 100° C. for 18 hours. The reaction mixture was allowed to cool to room temperature, filtered and the filtrate was concentrated in vacuo. The residue was purified by column chromatography on silica, eluted with 0-20% EtOAc/toluene to afford the title compound.

$^1$H NMR (400 MHz, CDCl$_3$) δ ppm 1.22 (t, J=7.08 Hz, 3 H), 1.88-2.03 (m, 2 H), 3.25-3.36 (m, 1 H), 3.58 (d, J=19.35 Hz, 1 H), 3.83 (d, J=19.07 Hz, 1 H), 3.87-3.97 (m, 1 H), 4.06-4.22 (m, 2 H), 4.32-4.60 (m, 2 H), 5.05 (s, 1 H), 7.16 (d, J=7.36 Hz, 1 H), 7.22-7.30 (m, 2 H), 7.39 (d, J=7.63 Hz, 1 H)

MS ES$^+$: 280

Step (ii): 2-(3-fluoropropyl)-3-oxo-1,2,3,4-tetrahydroisoquinoline-1-carboxylic acid LiOH.H$_2$O (0.71 g, 17.6 mmol) was added to a solution of ethyl 2-(3-fluoropropyl)-3-oxo-1,2,3,4-tetrahydroisoquinoline-1-carboxylate (4.50 g, 16.1 mmol) in THF (100 mL) and water (33 mL) and stirred for 18 hours. The reaction was concentrated in vacuo. Aqueous HCl was added to pH 7 and the resulting solid filtered, azeotroped with toluene and dried in vacuo to afford the title compound.

$^1$H NMR (400 MHz, CD$_3$OD) δ ppm 1.88-2.12 (m, 3 H), 3.26-3.30 (m, 1 H), 3.32-3.37 (m, 1 H), 3.41-3.52 (m, 1 H), 3.87-4.04 (m, 2 H), 4.32-4.58 (m, 2 H), 7.08-7.17 (m, 1 H), 7.19-7.29 (m, 2 H), 7.44-7.54 (m, 1 H)

MS ES$^+$: 252

Intermediates L2 and L3: (1S)-1-[(4S)-4-benzyl-2-oxo-1,3-oxazolidine-3-carbonyl]-2-(3-fluoropropyl)-1,2,3,4-tetrahydroisoquinolin-3-one and (1R)-1-[(4S)-4-benzyl-2-oxo-1,3-oxazolidine-3-carbonyl]-2-(3-fluoropropyl)-1,2,3,4-tetrahydroisoquinolin-3-one

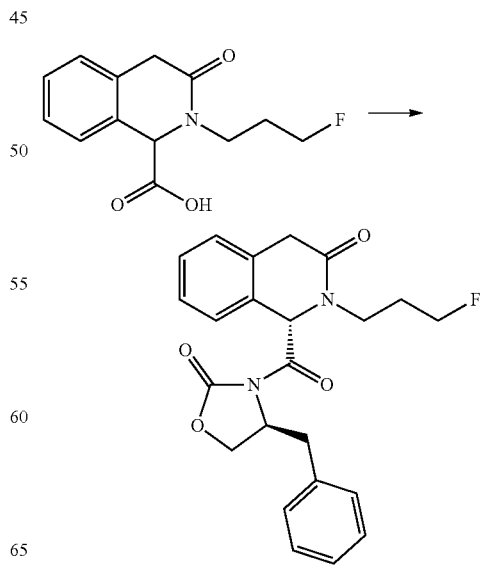

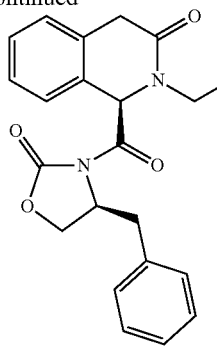

A solution of 2-(3-fluoropropyl)-3-oxo-1,2,3,4-tetrahydroisoquinoline-1-carboxylic acid (Intermediate L1, 4.0 g, 13.6 mmol) in THF (10 mL) at −10° C. was treated with TEA (7.27 mL, 16.3 mmol) in a dropwise fashion with stirring followed by pivolyl chloride (0.105 mL, 14.3 mmol). The reaction was stirred at −10° C. for 30 minutes. A second flask containing (4S)-4-benzyl-1,3-oxazolidin-2-one (151 mg, 13.6 mmol) in THF (10 mL) at −78° C. was treated with n-butyllithium (2.5 M in hexanes, 5.72 mL, 14.3 mmol) in a dropwise fashion. The reaction was stirred at −78° C. for 20 minutes. The resulting solution was cannulated to a cooled solution (−78° C.) of the mixed anhydride above. The reaction was stirred at −78° C. for 30 minutes and allowed to warm to room temperature for 4 hours. The reaction was quenched with NH₄Cl solution and extracted with EtOAc. The organic was collected, washed with 1 N HCl, bicarbonate and brine, dried (MgSO₄) and concentrated in vacuo. The resulting residue was purified by column chromatography on silica, eluted with 20-33% EtOAc/hexanes to afford the title compounds.

Intermediate L2—First Eluting Diastereomer, (1S)-1-[(4S)-4-benzyl-2-oxo-1,3-oxazolidine-3-carbonyl]-2-(3-fluoropropyl)-1,2,3,4-tetrahydroisoquinolin-3-one $^1$H NMR (400 MHz, CDCl₃) δ ppm 1.93-2.15 (m, 2 H), 2.77-2.88 (m, 1 H), 3.31-3.50 (m, 2 H), 3.62 (d, J=19.35 Hz, 1 H), 3.83-3.96 (m, 1 H), 4.11 (d, J=19.35 Hz, 1 H), 4.15-4.30 (m, 2 H), 4.39-4.63 (m, 3 H), 6.77 (s, 1 H), 7.16-7.26 (m, 4 H), 7.28-7.39 (m, 4 H), 7.52-7.59 (m, 1 H)

MS ES$^+$: 411

Intermediate L3—Second Eluting Diastereomer, (1R)-1-[(4S)-4-benzyl-2-oxo-1,3-oxazolidine-3-carbonyl]-2-(3-fluoropropyl)-1,2,3,4-tetrahydroisoquinolin-3-one $^1$H NMR (400 MHz, CDCl₃) δ ppm 1.88-2.09 (m, 2 H), 2.60-2.70 (m, 1 H), 2.74-2.82 (m, 1 H), 3.29-3.39 (m, 1 H), 3.59 (d, J=19.35 Hz, 1 H), 3.76-3.87 (m, 1 H), 4.03 (d, J=19.07 Hz, 1 H), 4.16-4.24 (m, 1 H), 4.32-4.43 (m, 2 H), 4.46-4.56 (m, 1 H), 4.69-4.83 (m, 1 H), 6.71-6.84 (m, 3 H), 7.09-7.23 (m, 4 H), 7.24-7.41 (m, 4 H), 7.64-7.74 (m, 1 H)

MS ES$^+$: 411

Intermediate L: (1S)-2-(3-fluoropropyl)-3-oxo-1,2,3,4-tetrahydroisoquinoline-1-carboxylic acid

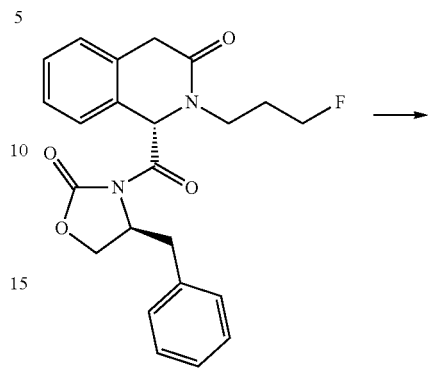

A solution of (1S)-1-[(4S)-4-benzyl-2-oxo-1,3-oxazolidine-3-carbonyl]-2-(3-fluoropropyl)-1,2,3,4-tetrahydroisoquinolin-3-one (Intermediate L2, 1.72 g, 4.19 mmol) in THF (55 mL) and water (18 mL) was at 0° C. was treated with LiOH.H₂O (0.352 g, 8.38 mmol) followed by H₂O₂.H₂O (3.47 mL, 33.52 mmol) in a dropwise fashion. The reaction was stirred at 0° C. for 2 hours, then warmed to room temperature and stirred for 18 hours. The reaction was carefully quenched with sodium thiosulfate and the pH adjusted to pH 1 and extracted with EtOAc. The organic was collected, washed with brine, dried (Na₂SO₄) and concentrated in vacuo. The aqueous was concentrated in vacuo and combined with the organic layer and purified by column chromatography on silica, eluted with 100% EtOAc with 1% AcOH to afford the title compound.

$^1$H NMR (400 MHz, CD₃OD) δ ppm 1.87-2.10 (m, 2 H), 3.31-3.38 (m, 2 H), 3.52 (d, J=19.07 Hz, 1 H), 3.82 (d, J=19.07 Hz, 1 H), 3.88-3.96 (m, 1 H), 4.31-4.56 (m, 2 H), 5.20 (s, 1 H), 7.15-7.23 (m, 1 H), 7.25-7.35 (m, 2 H), 7.45-7.53 (m, 1 H)

MS ES$^+$: 252

Intermediate M: 2-[(oxan-4-yl)methyl]-3-oxo-1,2,3,4-tetrahydroisoquinoline-1-carboxylic acid

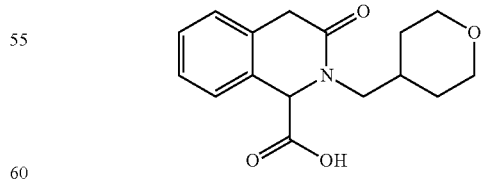

Prepared as described for 2-(3-fluoropropyl)-3-oxo-1,2,3,4-tetrahydroisoquinoline-1-carboxylic acid (Intermediate L1) using ethyl 2-bromo-2-[2-(2-ethoxy-2-oxoethyl)phenyl]acetate (Intermediate E1, 10 g, 30.4 mmol) and 4-(aminomethyl)tetrahydro-2H-pyran (4.2 g, 36.5 mmol) to afford the title compound.

¹H NMR (400 MHz, DMSO-d₆) δ ppm 1.03-1.26 (m, 2 H) 1.31-1.44 (m, 1 H) 1.49-1.59 (m, 1 H) 1.75-1.90 (m, 1 H) 2.68-2.81 (m, 1 H) 3.08-3.29 (m, 4 H) 3.62-3.84 (m, 4 H) 4.59 (s, 1 H) 7.00-7.16 (m, 3 H) 7.28-7.35 (m, 1 H)

ES⁻: 288

Intermediate N: 3-oxo-2-[(pyridin-2-yl)methyl]-1,2,3,4-tetrahydroisoquinoline-1-carboxylic acid

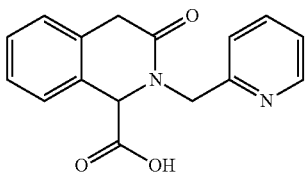 [SMILES: O=C(O)C1c2ccccc2CC(=O)N1Cc1ccccn1]

Prepared as described for 2-(3-fluoropropyl)-3-oxo-1,2,3,4-tetrahydroisoquinoline-1-carboxylic acid (Intermediate L1) using ethyl 2-bromo-2-[2-(2-ethoxy-2-oxoethyl)phenyl]acetate (Intermediate E1, 10 g, 30.4 mmol) and 2-picolylamine (3.94 g, 36.5 mmol) to afford the title compound.

¹H NMR (400 MHz, DMSO-d₆) δ ppm 3.34-3.45 (m, 2 H) 3.77-3.97 (m, 2 H) 4.59 (s, 1 H) 5.34 (d, J=15.80 Hz, 1 H) 7.01-7.32 (m, 6 H) 7.60-7.71 (m, 1 H) 8.47 (d, J=4.36 Hz, 1 H)

MS ES⁺: 283

Intermediate O: 2-(cyclopropylmethoxy)-2-(4-fluorophenyl)acetic acid

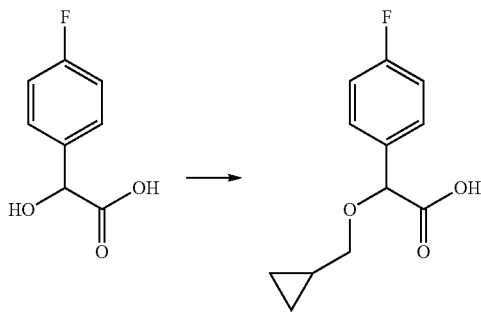 [SMILES: O=C(O)C(O)c1ccc(F)cc1 ; O=C(O)C(OCC1CC1)c1ccc(F)cc1]

Sodium hydride (60% dispersion in mineral oil, 5.88 g, 147 mmol) was added to a solution of 2-(4-fluorophenyl)-2-hydroxyacetic acid (10.0 g, 58.8 mmol) and in DMF (180 mL) under nitrogen and stirred for 30 minutes. (Bromomethyl)cyclopropane (14.27 mL, 147 mmol) was added and the reaction was stirred at room temperature for 18 hours. The mixture was diluted with EtOAc and washed with saturated NaHCO₃ solution. The aqueous was acidified to pH 1 with 2N HCl and extracted with EtOAc. The combined organics were dried (phase separator) and concentrated in vacuo to afford the title compound.

¹H NMR (300 MHz, CD₂Cl₂) δ ppm 0.10-0.27 (m, 2 H), 0.45-0.62 (m, 2 H), 1.00-1.17 (m, 1 H), 3.24-3.46 (m, 2 H), 4.91 (s, 1 H), 6.99-7.14 (m, 2 H), 7.39-7.50 (m, 2 H), 8.72-9.22 (m, 1 H)

MS ES⁻: 223

Intermediate P: 2-(2,4-difluorophenyl)-2-[(2-methylpyrimidin-4-yl)oxy]acetic acid

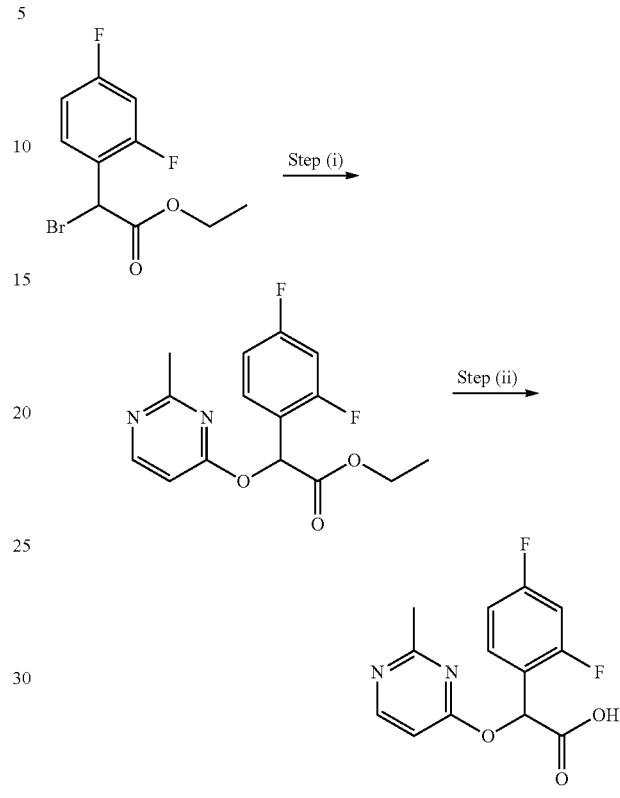

Step (i): ethyl 2-(2,4-difluorophenyl)-2-[(2-methylpyrimidin-4-yl)oxy]acetate

Caesium carbonate (642 mg, 1.971 mmol) was added to a solution of ethyl 2-bromo-2-(2,4-difluorophenyl)acetate (Intermediate K1, 500 mg, 1.792 mmol) and 2-methylpyrimidin-4-ol (217 mg, 1.971 mmol) in DMF (10 ml) under nitrogen. The reaction was stirred at room temperature for 1 hour. The mixture was partitioned between EtOAc and water/brine (50:50). The phases were separated and the aqueous extracted with EtOAc. The combined organics were washed with water/saturated brine (50:50), dried (phase separator) and concentrated in vacuo. The crude product was purified by reverse phase chromatography on C18 silica eluted with 40-70% acetonitrile/water (with 0.05% ammonia) to afford the title compound.

¹H NMR (400 MHz, DMSO-d₆) δ ppm 1.11-1.18 (m, 3 H) 2.50 (s, 3 H) 4.09-4.28 (m, 2 H) 6.50 (s, 1 H) 6.90-6.94 (m, 1 H) 7.16-7.25 (m, 1 H) 7.38-7.45 (m, 1 H) 7.60-7.71 (m, 1 H) 8.48-8.52 (m, 1 H)

MS ES⁺: 309

Step (ii): 2-(2,4-difluorophenyl)-2-[(2-methylpyrimidin-4-yl)oxy]acetic acid

LiOH (39.6 mg, 1.654 mmol) was added to a solution of ethyl 2-(2,4-difluorophenyl)-2-[(2-methylpyrimidin-4-yl)oxy]acetate (255 mg, 0.827 mmol) in water (2.0 mL) and THF (2.0 mL) under nitrogen. The reaction was stirred at room temperature for 18 hours. The mixture was partitioned between DCM and 5% citric acid. The phases were separated and the aqueous extracted with DCM. The combined organics were washed with 5% citric acid, dried (phase separator) and concentrated in vacuo to afford the title compound.

¹H NMR (400 MHz, DMSO-d₆) δ ppm 2.52 (s, 3 H), 6.48 (s, 1 H), 6.88 (d, J=5.78 Hz, 1 H), 7.16-7.23 (m, 1 H), 7.34-7.44 (m, 1 H), 7.60-7.69 (m, 1 H), 8.47 (d, J=5.87 Hz, 1 H)

MS ES⁺: 281

Intermediate Q: 2-(2,4-difluorophenyl)-2-(2-oxo-1, 2-dihydropyridin-1-yl)acetic acid

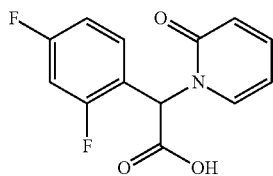 [SMILES: O=C(O)C(c1ccc(F)cc1F)n1ccccc1=O]

Step (i): ethyl 2-(2,4-difluorophenyl)-2-(2-oxo-1,2-dihydropyridin-1-yl)acetate

Caesium carbonate (1.374 g, 4.22 mmol) was added to a solution of ethyl 2-bromo-2-(2,4-difluorophenyl)acetate (Intermediate K1, 1.07 g, 3.83 mmol) and pyridin-2-ol (0.413 g, 4.22 mmol) in DMF (20 mL) under nitrogen. The reaction was stirred at room temperature for 3 hours. The mixture was partitioned between ethyl acetate and brine/water (1:1). The phases were separated and the aqueous extracted with ethyl acetate. The combined organics were washed with brine/water (1:1), dried (phase separator) and concentrated in vacuo. The crude product was purified by column chromatography on silica, eluted with 0-50% ethyl acetate/ petroleum ether to afford the title compound.

¹H NMR (400 MHz, DMSO-d₆) δ ppm 1.14-1.23 (m, 3 H), 4.17-4.26 (m, 2 H), 6.24-6.31 (m, 1 H), 6.44-6.51 (m, 1 H), 6.59 (s, 1 H), 7.14-7.23 (m, 1 H), 7.35-7.44 (m, 2 H), 7.45-7.55 (m, 2 H)

MS ES⁺: 294

Step (ii): 2-(2,4-difluorophenyl)-2-(2-oxo-1,2-dihydropyridin-1-yl)acetic acid

LiOH (90 mg, 3.75 mmol) was added to a solution of ethyl 2-(2,4-difluorophenyl)-2-(2-oxo-1,2-dihydropyridin-1-yl)acetate (550 mg, 1.875 mmol) in water (5 mL) and THF (5 mL) under nitrogen. The reaction was stirred at room temperature for 18 hours. Water was added and 2 M HCl added to pH 2, ethyl acetate was added and the phases were separated. The aqueous was further extracted with ethyl acetate. The combined organics were washed with water, dried (phase separator) and concentrated in vacuo to afford the title compound.

¹H NMR (300 MHz, DMSO-d₆) δ ppm 6.20-6.29 (m, 1 H) 6.41-6.50 (m, 1 H) 6.58 (s, 1 H) 7.01-7.23 (m, 1 H) 7.31-7.58 (m, 4 H) 13.61 (br. s., 1 H)

MS ES⁺: 266

Intermediate R: (2S)—N-[(trans)-4-(1,3-dioxo-2,3-dihydro-1H-isoindol-2-yl)-3,4-dihydro-2H-1-benzopyran-3-yl]-2-(4-fluorophenyl)propanamide

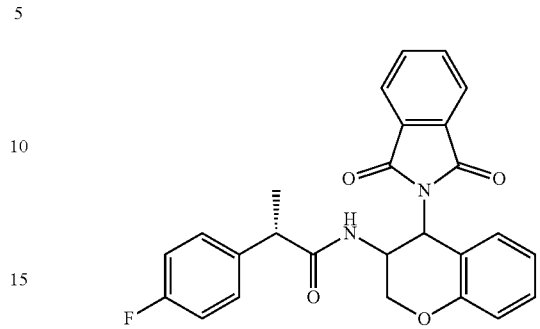

Methanesulfonic anhydride (221 mg, 1.268 mmol) was added as a solution in THF (2 mL) to a dry ice/acetone cooled solution (2S)-2-(4-fluorophenyl)-N-((cis)-4-hydroxy-3,4-dihydro-2H-1-benzopyran-3-yl)propanamide (Intermediate F2, 200 mg, 0.634 mmol) and TEA (0.265 mL, 1.903 mmol) in THF (4 mL). The cooling bath was switched for an ice/water bath. After 30 minutes, potassium 1,3-dioxoisoindolin-2-ide (587 mg, 3.17 mmol) and 18-crown-6 (838 mg, 3.17 mmol) were added and the reaction allowed to warm to room temperature for 18 hours. The reaction mixture was partitioned between DCM and water and the organic phase was purified by column chromatography on silica, eluted with 0-100% ethyl acetate/petroleum ether to afford the title compound

MS ES+: 445

Intermediate S: (trans)-4-methoxy-3,4-dihydro-2H-1-benzopyran-3-amine hydrochloride

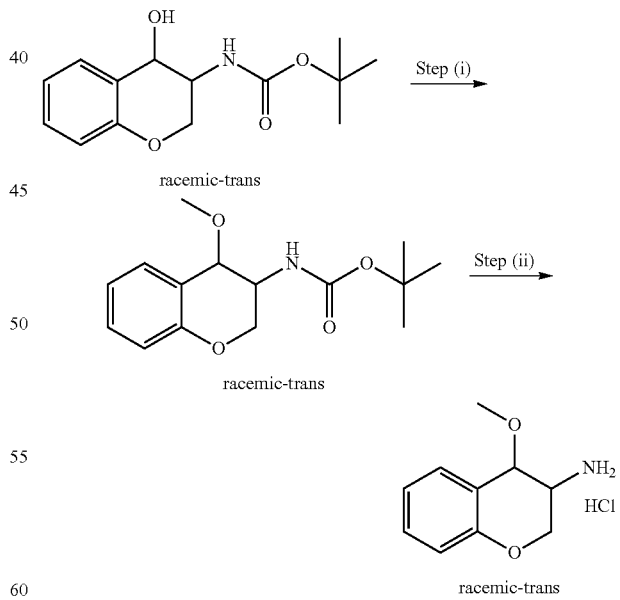

Step (i): tert-butyl N-((trans)-4-methoxy-3,4-dihydro-2H-1-benzopyran-3-yl)carbamate Methyl iodide (1.173 ml, 18.75 mmol) was added to a suspension of tert-butyl N-((trans)-4-hydroxy-3,4-dihydro- 2H-1-benzopyran-3-yl)carbamate (Intermediate A3, 1.99 g, 7.50 mmol) and silver oxide (2.086 g, 9.00 mmol) in acetonitrile (40 ml). The reaction was stirred at room temperature for 2 days in a sealed flask in the dark. Further portions of silver oxide (2.086 g, 9.00 mmol) and methyl iodide (1.173 ml, 18.75 mmol) were added and the reaction was stirred for a further 2 days. The suspension was filtered through celite, washed with methanol and concentrated in vacuo to afford the title compound.

$^1$H NMR (400 MHz, DMSO-$d_6$) δ ppm 1.40 (s, 9 H) 3.39 (s, 3 H) 3.81-3.90 (m, 1 H) 3.98-4.12 (m, 2 H) 4.15-4.23 (m, 1 H) 6.75-6.85 (m, 1 H) 6.89-6.98 (m, 2 H) 7.16-7.25 (m, 1 H) 7.27-7.33 (m, 1 H)

Step (ii): (trans)-4-methoxy-3,4-dihydro-2H-1-benzopyran-3-amine hydrochloride

Hydrogen chloride (4M in dioxane) (6.49 ml, 26.0 mmol) was added to a suspension of tert-butyl N-((trans)-4-methoxy-3,4-dihydro-2H-1-benzopyran-3-yl)carbamate (1.45 g, 5.19 mmol) in methanol (20 ml). The reaction was stirred at room temperature overnight. The solution was concentrated in vacuo, azeotroped with toluene and dried in a vacuum oven to afford the title compound.

$^1$H NMR (400 MHz, DMSO-$d_6$) δ ppm 3.45 (s, 3 H) 3.71-3.80 (m, 1 H) 4.07-4.19 (m, 1 H) 4.26-4.38 (m, 2 H) 6.78-6.95 (m, 1 H) 6.98-7.06 (m, 1 H) 7.27-7.42 (m, 2 H) 8.50 (br. s., 3 H)

MS ES$^+$: 148 (—OCH$_3$)

Example 1: (2S)—N-((cis)-4-hydroxy-3,4-dihydro-2H-1-benzopyran-3-yl)-2-phenylpropanamide

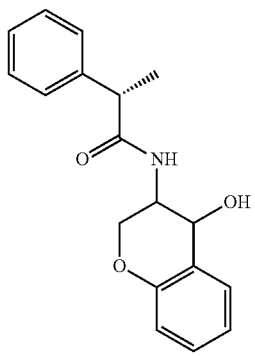 [SMILES: C[C@H](C(=O)NC1COc2ccccc2C1O)c1ccccc1]

T3P (50 wt. % in EtOAc, 1.85 ml, 3.11 mmol) was added dropwise to a mixture of (cis)-3-amino-3,4-dihydro-2H-1-benzopyran-4-ol hydrochloride (Intermediate A, 257 mg, 1.56 mmol) and (2S)-2-phenylpropanoic acid (245 mg, 1.63 mmol) in THF (20 mL). The mixture was stirred at room temperature for 5 minutes. TEA (1.73 mL, 12.4 mmol) was added dropwise. The mixture was stirred at room temperature overnight, then partitioned between EtOAc and saturated aq. NaHCO$_3$. The phases were separated and the organic washed with further saturated aq. NaHCO$_3$ and brine, then dried (Na$_2$SO$_4$) and concentrated in vacuo. The residue was purified by column chromatography on silica, eluted with 0-1% methanol/DCM to afford the title compound.

$^1$H NMR (400 MHz, CD$_3$OD) δ ppm 1.44-1.48 (m, 3 H), 3.75-3.80 (m, 1 H), 3.91-3.94 (m, 1 H), 4.01-4.07 (m, 1 H), 4.21-4.23 (m, 1 H) 4.52-4.68 (m, 1 H), 4.91 (s, 1 H), 6.76-6.93 (m, 2 H), 7.14-7.36 (m, 7 H), 7.64-7.65 (m, 1 H)

MS ES$^+$: 298

Example 2: (2S)—N-((trans)-4-hydroxy-3,4-dihydro-2H-1-benzopyran-3-yl)-2-phenylpropanamide

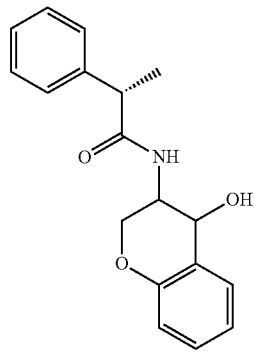 [SMILES: C[C@H](C(=O)NC1COc2ccccc2C1O)c1ccccc1]

Prepared as described for (2S)—N-((cis)-4-hydroxy-3,4-dihydro-2H-1-benzopyran-3-yl)-2-phenylpropanamide (Example 1) using (trans)-3-amino-3,4-dihydro-2H-1-benzopyran-4-ol hydrochloride (Intermediate B, 250 mg, 1.52 mmol) and (2S)-2-phenylpropanoic acid (239 mg, 1.59 mmol). The crude material was purified by column chromatography on silica, eluted with 0-1% methanol/DCM then by reverse phase preparative HPLC eluted with acetonitrile/water (with 0.1% ammonia) to afford the title compound.

$^1$H NMR (400 MHz, DMSO-$d_6$) δ ppm 1.25-1.38 (m, 3 H), 3.65-3.77 (m, 1 H), 3.81-4.22 (m, 3 H), 4.27-4.47 (m, 1 H), 5.55-5.71 (m, 1 H), 6.74-6.83 (m, 1 H), 6.86-6.99 (m, 1 H), 7.13-7.39 (m, 7 H), 7.98-8.13 (m, 1 H)

MS ES$^+$: 298

Example 3: (2S)—N-((cis)-6-fluoro-4-hydroxy-3,4-dihydro-2H-1-benzopyran-3-yl)-2-phenylpropanamide

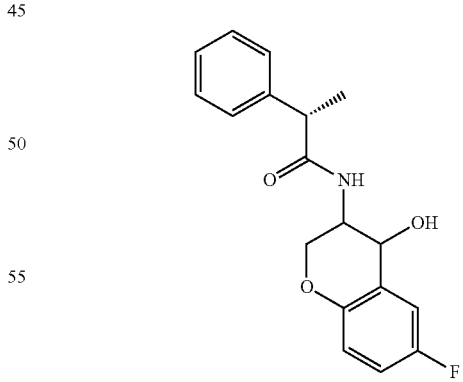

Prepared as described for (2S)—N-((cis)-4-hydroxy-3,4-dihydro-2H-1-benzopyran-3-yl)-2-phenylpropanamide (Example 1) using 3-amino-6-fluoro-3,4-dihydro-2H-1-benzopyran-4-ol (Intermediate C, 500 mg, 2.73 mmol) and (2S)-2-phenylpropanoic acid (430 mg, 2.86 mmol). The crude material was purified by column chromatography on silica, eluted with 0-0.5% methanol/DCM then by reverse phase preparative HPLC eluted with acetonitrile/water (with 0.1% ammonia) to afford the title compound.

¹H NMR (300 MHz, DMSO-d₆) δ ppm 1.27-1.41 (m, 3 H), 3.76-3.92 (m, 2 H), 3.97-4.18 (m, 2 H), 4.44-4.66 (m, 1 H), 5.71-5.82 (m, 1 H), 6.74-6.87 (m, 1 H), 6.97-7.12 (m, 2 H), 7.16-7.41 (m, 5 H), 7.69-7.80 (m, 1 H)

MS ES⁺: 338 (M+Na)

Example 4: (2S)—N-(4-oxo-3,4-dihydro-2H-1-benzopyran-3-yl)-2-phenylpropanamide

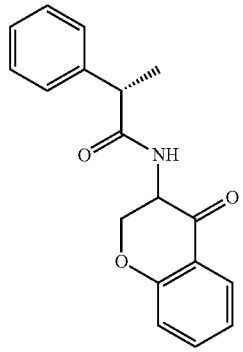 [SMILES: C[C@H](C(=O)NC1COc2ccccc2C1=O)c1ccccc1]

HATU (1198 mg, 3.15 mmol) was added to a solution of (S)-2-phenylpropanoic acid (451 mg, 3 mmol) and DIPEA (1.153 mL, 6.60 mmol) in DMF (5 mL). The mixture was stirred and allowed to stand for 5 minutes. 3-Aminochroman-4-one hydrochloride (599 mg, 3.00 mmol) was added and the reaction was stirred for 5 minutes. The mixture was diluted with EtOAc and washed with water. The organic phase was dried (MgSO₄) and concentrated in vacuo. The residue was purified by column chromatography on silica, eluted with (50-100% [1:1 EtOAc:THF]/petroleum ether to afford the title compound.

¹H NMR (400 MHz, DMSO-d₆) δ ppm 1.31-1.42 (m, 3 H), 3.71-3.83 (m, 1 H), 4.18-4.35 (m, 1 H), 4.36-4.54 (m, 1 H), 4.78-4.93 (m, 1 H), 7.03-7.16 (m, 2 H), 7.21-7.41 (m, 5 H), 7.56-7.64 (m, 1 H), 7.73-7.85 (m, 1 H), 8.34-8.44 (m, 1 H)

MS ES⁺: 296

Examples 5 and 6: (2S)—N-((trans)-4-hydroxy-3,4-dihydro-2H-1-benzopyran-3-yl)-2-phenylpropanamide (single stereoisomers)

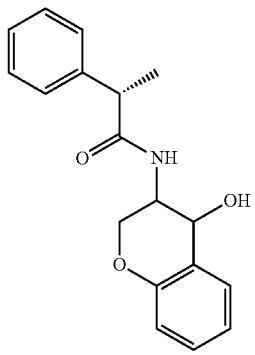 [SMILES: C[C@H](C(=O)NC1COc2ccccc2C1O)c1ccccc1]

(2S)—N-((trans)-4-hydroxy-3,4-dihydro-2H-1-benzopyran-3-yl)-2-phenylpropanamide (Example 2) was purified by chiral SFC (14% EtOH, IC column) to afford the title compounds.

1. Example 5—1ˢᵗ Eluting Peak

¹H NMR (400 MHz, DMSO-d₆) δ ppm 1.31 (d, J=7.06 Hz, 3 H), 3.66-3.75 (m, 1 H), 3.90-3.98 (m, 1 H), 4.00-4.07 (m, 1 H), 4.13-4.20 (m, 1 H), 4.26-4.34 (m, 1 H), 5.59 (d, J=6.05 Hz, 1 H), 6.78-6.83 (m, 1 H), 6.88-6.95 (m, 1 H), 7.14-7.28 (m, 7 H), 8.02-8.08 (m, 1 H)

MS ES⁺: 320

2. Example 6—2ⁿᵈ Eluting Peak

¹H NMR (400 MHz, DMSO-d₆) δ ppm 1.28 (d, J=7.06 Hz, 3 H), 3.66-3.75 (m, 1 H), 3.86-3.99 (m, 2 H), 4.05-4.13 (m, 1 H), 4.39-4.47 (m, 1 H), 5.66 (d, J=5.96 Hz, 1 H), 6.75-6.85 (m, 1 H), 6.88-6.98 (m, 1 H), 7.14-7.23 (m, 2 H), 7.25-7.36 (m, 5 H), 8.02-8.10 (m, 1 H)

MS ES⁺: 320

Examples 7 and 8: (2S)—N-((cis)-4-hydroxy-4-methyl-3,4-dihydro-2H-1-benzopyran-3-yl)-2-phenylpropanamide (single stereoisomers)

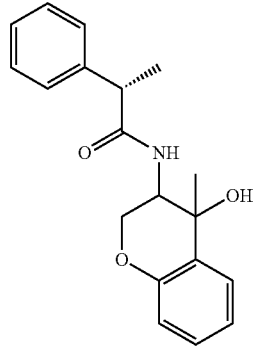 [SMILES: C[C@H](C(=O)NC1COc2ccccc2C1(C)O)c1ccccc1]

Methylmagnesium bromide (3 M in ether) (0.248 mL, 0.745 mmol) was added to a solution of (2S)—N-(4-oxo-3,4-dihydro-2H-1-benzopyran-3-yl)-2-phenylpropanamide (Example 4, 100 mg, 0.339 mmol) in THF (5 mL) in a dry-ice/acetone bath under nitrogen. The mixture was stirred and allowed to warm to room temperature for 18 hours. The mixture was quenched with water and partitioned between water and EtOAc. The organic phase was dried (MgSO₄) and concentrated in vacuo. The residue was purified by column chromatography on silica, eluted with 30-70% ethyl acetate/petroleum ether. The residue was purified by chiral SFC (20% MeOH, AD column) to afford the title compounds.

1. Example 7—1ˢᵗ Eluting Peak

¹H NMR (400 MHz, CDCl₃) δ ppm 1.33 (s, 3 H), 1.52 (d, J=7.15 Hz, 3 H), 3.48-3.58 (m, 1 H), 3.96-4.07 (m, 1 H), 4.32-4.45 (m, 2 H), 5.40-5.53 (m, 1 H), 6.77-6.86 (m, 1 H), 6.91-6.99 (m, 1 H), 7.16-7.30 (m, 7 H), 7.35-7.42 (m, 1 H)

MS ES⁺: 334

2. Example 8—2ⁿᵈ Eluting Peak

¹H NMR (400 MHz, CDCl₃) δ ppm 1.53 (d, J=7.15 Hz, 3 H), 1.56 (s, 3 H), 3.50-3.60 (m, 1 H), 3.88-3.96 (m, 1 H), 4.34-4.43 (m, 2 H), 5.49-5.59 (m, 1 H), 6.81-6.88 (m, 1 H), 6.96-7.04 (m, 1 H), 7.19-7.29 (m, 5 H), 7.30-7.36 (m, 2 H), 7.43-7.50 (m, 1 H)

MS ES+: 334

Example 9 and 10: (2S)—N-[(cis)-4-(methylamino)-3,4-dihydro-2H-1-benzopyran-3-yl]-2-phenylpropanamide (single stereoisomers)

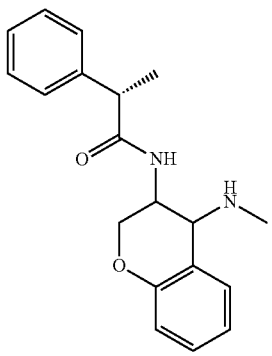 [SMILES: CNC1c2ccccc2OCC1NC(=O)[C@@H](C)c1ccccc1]

A suspension of (2S)—N-(4-oxo-3,4-dihydro-2H-1-benzopyran-3-yl)-2-phenylpropanamide (Example 4, 200 mg, 0.677 mmol) in methanamine (33% in EtOH) (2 mL, 21.3 mmol) and EtOH (3 mL) was stirred at room temperature for 20 hours. THF (2 mL) was added and the mixture was stirred for 5 days. The mixture was cooled to 0° C. and NaBH₄ (51 mg, 1.354 mmol) added. The reaction was stirred at 0° C. for 18 hours. The mixture was diluted with water and extracted twice with DCM. The combined organic phases were dried (MgSO₄) and concentrated in vacuo. The residue was purified by reverse phase preparative HPLC (eluted with acetonitrile/water (with 0.1% ammonia). The resulting residue was further purified by chiral SFC (30% IPA, IC column) to afford the title compounds.

1. Example 9—1st Eluting Peak

¹H NMR (400 MHz, CDCl₃) δ ppm 1.54 (d, J=7.15 Hz, 3 H), 2.32 (s, 3 H), 3.47-3.51 (m, 1 H), 3.53-3.62 (m, 1 H), 3.84-3.94 (m, 1 H), 4.13-4.20 (m, 1 H), 4.37-4.46 (m, 1 H), 6.08-6.20 (m, 1 H), 6.79-6.84 (m, 1 H), 6.85-6.92 (m, 1 H), 7.14-7.19 (m, 1 H), 7.21-7.26 (m, 2 H), 7.28-7.36 (m, 5 H)

MS ES+: 311

2. Example 10—2nd Eluting Peak

¹H NMR (400 MHz, CDCl₃) δ ppm 1.55 (d, J=7.15 Hz, 3 H), 2.47 (s, 3 H), 3.54 (d, J=4.68 Hz, 1 H), 3.57-3.66 (m, 1 H), 3.70-3.79 (m, 1 H), 4.09-4.17 (m, 1 H), 4.38-4.48 (m, 1 H), 6.16-6.24 (m, 1 H), 6.77-6.84 (m, 1 H), 6.86-6.94 (m, 1 H), 7.13-7.21 (m, 1 H), 7.24-7.27 (m, 2 H), 7.27-7.37 (m, 5 H)

MS ES+: 311

Example 11: (2S)—N-((trans)-4-methoxy-3,4-dihydro-2H-1-benzopyran-3-yl)-2-phenylpropanamide (single stereoisomer)

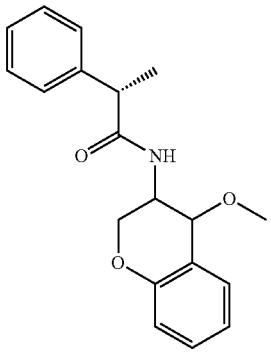 [SMILES: COC1c2ccccc2OCC1NC(=O)[C@@H](C)c1ccccc1]

NaH (60% suspension in mineral oil, 28 mg, 0.706 mmol) was added to a stirred solution of (2S)—N-((trans)-4-hydroxy-3,4-dihydro-2H-1-benzopyran-3-yl)-2-phenylpropanamide (Example 2, 200 mg, 0.673 mmol) in DMF (3 mL) at 0° C. The mixture was stirred under nitrogen and allowed to warm to room temperature for 30 minutes. The mixture was cooled to 0° C. and a solution of methyl iodide (0.046 mL, 0.740 mmol) in DMF (1 mL) was added dropwise and the mixture stirred for 5 minutes and warmed to room temperature for 1 hour. The reaction mixture was quenched with water and purified by reverse phase preparative HPLC eluted with acetonitrile/water (with 0.1% ammonia). The resulting residue was purified by chiral SFC (10% EtOH, AD column) to afford the title compound as the second eluting stereoisomer.

¹H NMR (400 MHz, DMSO-d₆) δ ppm 1.26 (d, J=6.97 Hz, 3 H), 3.42 (s, 3 H), 3.65-3.76 (m, 1 H), 3.99-4.07 (m, 2 H), 4.10-4.18 (m, 2 H), 6.80-6.89 (m, 1 H), 6.93-6.98 (m, 1 H), 7.17-7.34 (m, 7 H), 8.14-8.23 (m, 1 H)

MS ES⁻: 310

Examples 12 and 13: (2S)—N-((trans)-4-methanesulfonyl-3,4-dihydro-2H-1-benzopyran-3-yl)-2-phenylpropanamide (single stereoisomers)

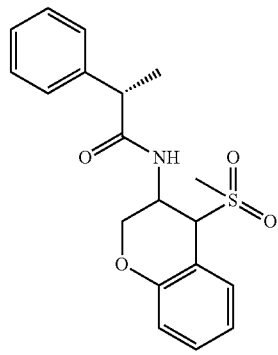 [SMILES: C[C@H](C(=O)NC1COc2ccccc2C1S(C)(=O)=O)c1ccccc1]

mCPBA (145 mg, 0.840 mmol) was added to a stirred solution of (2S)—N-[(trans)-4-(methylsulfanyl)-3,4-dihydro-2H-1-benzopyran-3-yl]-2-phenylpropanamide (Intermediate D, 110 mg, 0.336 mmol) in DCM (2 mL). After 1.5 hours, the reaction mixture was washed with water, dried (phase separator) and concentrated in vacuo. The crude product was purified by column chromatography on silica, eluted with 0-100% ethyl acetate/petroleum ether. The crude product was purified by reverse phase preparative HPLC eluted with acetonitrile/water (with 0.1% ammonia) to afford the title compounds.

1. Example 12—1st Eluting Peak $^1$H NMR (300 MHz, DMSO-$d_6$) δ ppm 1.31 (d, J=7.02 Hz, 3 H), 3.15 (s, 3 H), 3.64-3.77 (m, 1 H), 4.14-4.26 (m, 1 H), 4.36-4.47 (m, 2 H), 4.60-4.69 (m, 1 H), 6.86-6.99 (m, 2 H), 7.11-7.22 (m, 5 H), 7.25-7.38 (m, 2 H), 8.48-8.60 (m, 1 H)

MS ES$^+$: 360

2. Example 13—2nd Eluting Peak $^1$H NMR (300 MHz, DMSO-$d_6$) δ ppm 1.21-1.31 (m, 3 H), 3.21 (s, 3 H), 3.64-3.77 (m, 1 H), 4.02-4.13 (m, 1 H), 4.32-4.42 (m, 1 H), 4.51-4.68 (m, 2 H), 6.89-7.05 (m, 2 H), 7.16-7.36 (m, 6 H), 7.40-7.48 (m, 1 H), 8.54-8.64 (m, 1 H)

MS ES$^+$: 360

Example 14: (2S)—N-[(trans)-4-(methylamino)-3,4-dihydro-2H-1-benzopyran-3-yl]-2-phenylpropanamide

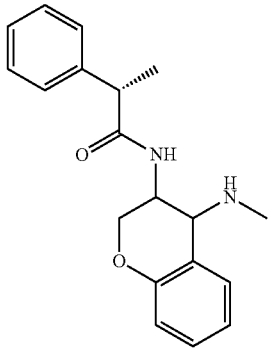 [SMILES: CNC1c2ccccc2OCC1NC(=O)[C@@H](C)c1ccccc1]

Methanesulfonic anhydride (117 mg, 0.673 mmol) as a solution in THF (1 mL) was added to a solution of (2S)—N-((cis)-4-hydroxy-3,4-dihydro-2H-1-benzopyran-3-yl)-2-phenylpropanamide (Example 1, 100 mg, 0.336 mmol) at −78° C. and TEA (0.136 mL, 1.009 mmol) in THF (2 mL) under nitrogen. The reaction was warmed to 0° C. and the reaction was stirred for 30 minutes. Methanamine (2M in THF, 0.841 mL, 1.682 mmol) was added and the reaction was allowed to warm to room temperature for 18 hours. The reaction mixture was partitioned between DCM and water. The organic was collected, dried (phase separator) and concentrated in vacuo. The crude product was purified by column chromatography on silica, eluted with 0-100% ethyl acetate/petroleum ether to afford the title compound.

$^1$H NMR (400 MHz, DMSO-$d_6$) δ ppm 1.25-1.34 (m, 3 H), 2.22-2.36 (m, 3 H), 3.34-3.51 (m, 1 H), 3.65-3.77 (m, 1 H), 3.88-3.96 (m, 1 H), 3.99-4.09 (m, 2 H), 4.12-4.26 (m, 1 H), 6.77-6.82 (m, 1 H), 6.85-6.95 (m, 1 H), 7.10-7.35 (m, 7 H), 7.94-8.04 (m, 1 H)

MS ES$^+$: 311

Example 15: (1S)-2-(cyclopropylmethyl)-N-((trans)-4-methoxy-3,4-dihydro-2H-1-benzopyran-3-yl)-3-oxo-1,2,3,4-tetrahydroisoquinoline-1-carboxamide

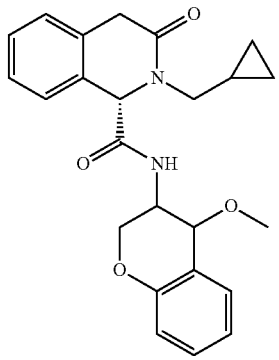 [SMILES: COC1c2ccccc2OCC1NC(=O)[C@@H]1c2ccccc2CC(=O)N1CC1CC1]

Iodomethane (0.043 ml, 0.688 mmol) was added to a vial containing (1S)-2-(cyclopropylmethyl)-N-((trans)-4-hydroxy-3,4-dihydro-2H-1-benzopyran-3-yl)-3-oxo-1,2,3,4-tetrahydroisoquinoline-1-carboxamide (Intermediate E, 135 mg, 0.344 mmol) and silver oxide (399 mg, 1.720 mmol) in acetonitrile (1.5 mL). The vial was sealed and wrapped in foil and stirred at room temperature for 4 days. More iodomethane (0.043 mL, 0.688 mmol) and silver oxide (399 mg, 1.720 mmol) were added and the reaction was stirred at room temperature for 18 hours. The reaction mixture was filtered through diatomaceous earth and the filtrate concentrated in vacuo. The resulting residue was purified by reverse phase preparative HPLC eluted with acetonitrile/water (with 0.1% ammonia) to afford the title compound.

$^1$H NMR (400 MHz, DMSO-$d_6$) δ ppm 0.01-0.48 (m, 4 H), 0.65-0.97 (m, 1 H), 3.06-3.29 (m, 4 H), 3.35-3.45 (m, 2 H), 3.79-4.27 (m, 5 H), 5.23-5.32 (m, 1 H), 6.86-7.57 (m, 8 H), 8.57-8.75 (m, 1 H)

MS ES$^+$: 407

Examples 16 and 17: (2S)-2-(4-fluorophenyl)-N-((trans)-4-methanesulfonyl-3,4-dihydro-2H-1-benzopyran-3-yl)propanamide (single stereoisomers)

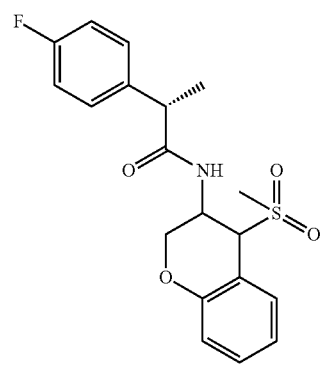 [SMILES: C[C@H](C(=O)NC1COc2ccccc2C1S(C)(=O)=O)c1ccc(F)cc1]

Prepared as described for (2S)—N-((trans)-4-methanesulfonyl-3,4-dihydro-2H-1-benzopyran-3-yl)-2-phenylpropanamide (single stereoisomers) (Examples 12 and 13) using (2S)-2-(4-fluorophenyl)-N-[(trans)-4-(methylsulfanyl)-3,4-dihydro-2H-1-benzopyran-3-yl]propanamide (Intermediate F, 342 mg, 0.990 mmol). The crude material was purified by reverse phase preparative HPLC eluted with acetonitrile/water (with 0.1% ammonia) to afford the title compounds.

1. Example 16—1$^{st}$ Eluting Peak Represents (2S)-2-(4-fluorophenyl)-N-((trans)-4-methanesulfonyl-3,4-dihydro-2H-1-benzopyran-3-yl)propanamide (CPD1 or Compound 1).

$^1$H NMR (400 MHz, CD$_2$Cl$_2$) δ ppm 1.46 (d, J=7.15 Hz, 3 H), 3.17 (s, 2 H), 3.44-3.57 (m, 1 H), 4.18-4.29 (m, 2 H), 4.58-4.71 (m, 1 H), 5.94-6.08 (m, 1 H), 6.86-6.95 (m, 2 H), 6.97-7.04 (m, 1 H), 7.09-7.14 (m, 2 H), 7.27-7.37 (m, 2 H)
MS ES$^+$: 378

2. Example 17—2$^{nd}$ Eluting Peak $^1$H NMR (400 MHz, CD$_2$Cl$_2$) δ ppm 1.43 (d, J=7.15 Hz, 3 H), 3.22 (s, 3 H), 3.44-3.52 (m, 1 H), 4.10-4.19 (m, 1 H), 4.31-4.37 (m, 1 H), 4.54-4.67 (m, 2 H), 5.99-6.10 (m, 1 H), 6.92-7.10 (m, 4 H), 7.21-7.28 (m, 2 H), 7.32-7.40 (m, 1 H), 7.45-7.51 (m, 1 H)
MS ES$^+$: 378

Examples 18 and 19: (1S)-2-(cyclopropylmethyl)-N-((trans)-4-methoxy-3,4-dihydro-2H-1-benzopyran-3-yl)-3-oxo-1,2,3,4-tetrahydroisoquinoline-1-carboxamide (single stereoisomers)

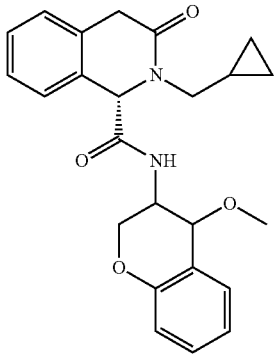 [SMILES: COC1c2ccccc2OCC1NC(=O)[C@@H]1c2ccccc2CC(=O)N1CC1CC1]

(1S)-2-(cyclopropylmethyl)-N-((trans)-4-methoxy-3,4-dihydro-2H-1-benzopyran-3-yl)-3-oxo-1,2,3,4-tetrahydroisoquinoline-1-carboxamide (Example 15) was purified by chiral SFC (32% MeOH, Lux-C4 column) to afford the title compounds.

1. Example 18—1$^{st}$ Eluting Peak $^1$H NMR (300 MHz, DMSO-d$_6$) δ ppm 0.01-0.33 (m, 4 H), 0.55-0.75 (m, 1 H), 2.98-3.08 (m, 2 H), 3.32 (s, 3 H), 3.38 (s, 1 H), 3.80-4.16 (m, 5 H), 5.21 (s, 1 H), 6.82-6.95 (m, 2 H), 7.09-7.28 (m, 5 H), 7.42-7.51 (m, 1 H), 8.60-8.72 (m, 1 H)
MS ES$^+$: 407

2. Example 19—2$^{nd}$ Eluting Peak $^1$H NMR (300 MHz, DMSO-d$_6$) δ ppm 0.11-0.51 (m, 4 H), 0.83-0.99 (m, 1 H), 3.07-3.28 (m, 5 H), 3.34-3.45 (m, 1 H), 3.78-3.93 (m, 2 H), 4.02-4.26 (m, 3 H), 5.28 (s, 1 H), 6.84-6.96 (m, 2 H), 6.97-7.34 (m, 6 H), 8.56-8.66 (m, 1 H)
MS ES$^+$: 407

Examples 20 and 21: (2S)-2-(4-chlorophenyl)-N-((trans)-4-methanesulfonyl-3,4-dihydro-2H-1-benzopyran-3-yl)propanamide (single stereoisomers)

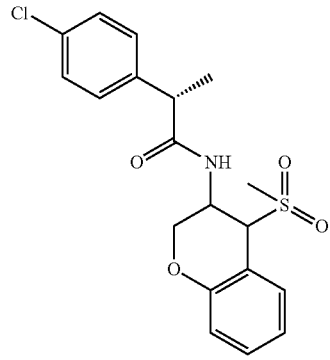 [SMILES: C[C@H](C(=O)NC1COc2ccccc2C1S(C)(=O)=O)c1ccc(Cl)cc1]

Prepared as described for (2S)—N-((trans)-4-methanesulfonyl-3,4-dihydro-2H-1-benzopyran-3-yl)-2-phenylpropanamide (single stereoisomers) (Examples 12 and 13) using (2S)-2-(4-chlorophenyl)-N-[(trans)-4-(methylsulfanyl)-3,4-dihydro-2H-1-benzopyran-3-yl]propanamide (Intermediate G, 234 mg, 0.647 mmol). The crude material was purified by reverse phase preparative HPLC eluted with acetonitrile/water (with 0.1% ammonia) to afford the title compounds.

1. Example 20—1$^{st}$ Eluting Peak $^1$H NMR (400 MHz, DMSO-d$_6$) δ ppm 1.30 (d, J=6.97 Hz, 3 H), 3.16 (s, 3 H), 3.68-3.80 (m, 1 H), 4.17-4.25 (m, 1 H), 4.34-4.48 (m, 2 H), 4.60-4.69 (m, 1 H), 6.88-6.99 (m, 2 H), 7.16-7.35 (m, 6 H), 8.53-8.63 (m, 1 H)
MS ES$^+$: 394

2. Example 21—2$^{nd}$ Eluting Peak $^1$H NMR (400 MHz, DMSO-d$_6$) δ ppm 1.25 (d, J=6.97 Hz, 3 H), 3.21 (s, 3 H), 3.66-3.77 (m, 1 H), 4.04-4.13 (m, 1 H), 4.32-4.43 (m, 1 H), 4.50-4.62 (m, 2 H), 6.89-7.03 (m, 2 H), 7.27-7.38 (m, 5 H), 7.41-7.47 (m, 1 H), 8.61-8.67 (m, 1 H)
MS ES$^+$: 394

Example 22: (2S)-2-(4-fluorophenyl)-N-[(trans)-4-(methylamino)-3,4-dihydro-2H-1-benzopyran-3-yl]propanamide (single stereoisomer)

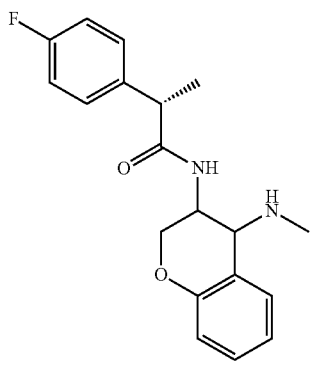

Methanesulfonic anhydride (110 mg, 0.634 mmol) as a solution in THF (1 mL) was added to a stirred solution of (2S)-2-(4-fluorophenyl)-N-((cis)-4-hydroxy-3,4-dihydro-2H-1-benzopyran-3-yl)propanamide (Intermediate H, 100 mg, 0.317 mmol) and TEA (0.133 mL, 0.951 mmol) in THF (2 mL) at −78° C. The reaction was warmed to 0° C. for 30 minutes. Methanamine (2 M in THF, 0.793 mL, 1.586 mmol) was added and the reaction was warmed to room temperature for 18 hours. The reaction mixture was partitioned between DCM and water. The organics were dried (phase separator) and concentrated in vacuo. The resulting residue was purified by reverse phase preparative HPLC eluted with acetonitrile/water (with 0.1% ammonia) to afford the title compound.

$^1$H NMR (400 MHz, DMSO-$d_6$) δ ppm 1.30 (d, J=7.06 Hz, 3 H), 2.24 (s, 3 H), 3.33-3.37 (m, 2 H), 3.68-3.77 (m, 1 H), 3.99-4.09 (m, 2 H), 4.18-4.26 (m, 1 H), 6.78-6.82 (m, 1 H), 6.85-6.91 (m, 1 H), 7.02-7.10 (m, 2 H), 7.12-7.18 (m, 1 H), 7.20-7.31 (m, 3 H), 7.97-8.03 (m, 1 H)

MS ES$^+$: 329

Example 23: (2S)-2-(4-fluorophenyl)-N-[(trans)-4-(methylamino)-3,4-dihydro-2H-1-benzopyran-3-yl]propanamide (single stereoisomer)

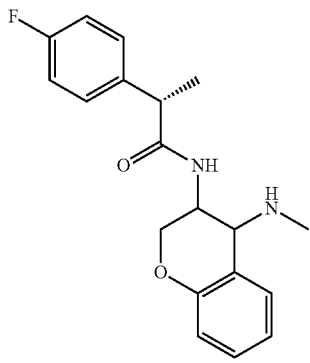

Prepared as described for (2S)-2-(4-fluorophenyl)-N-[(trans)-4-(methylamino)-3,4-dihydro-2H-1-benzopyran-3-yl]propanamide (single stereoisomer) (Example 22) using (2S)-2-(4-fluorophenyl)-N-((cis)-4-hydroxy-3,4-dihydro-2H-1-benzopyran-3-yl)propanamide (Intermediate I, 100 mg, 0.317 mmol). The crude material was purified by reverse phase preparative HPLC eluted with acetonitrile/water (with 0.1% ammonia) to afford the title compound.

$^1$H NMR (400 MHz, DMSO-$d_6$) δ ppm 1.26 (d, J=7.06 Hz, 3 H), 2.08 (br. s., 1 H), 2.35 (s, 3 H), 3.43-3.50 (m, 1 H), 3.67-3.76 (m, 1 H), 3.87-3.95 (m, 1 H), 4.01-4.09 (m, 1 H), 4.12-4.21 (m, 1 H), 6.76-6.82 (m, 1 H), 6.88-6.96 (m, 1 H), 7.06-7.20 (m, 3 H), 7.27-7.40 (m, 3 H), 7.99-8.06 (m, 1 H)

MS ES$^+$: 329

Examples 24: 2-(4-fluorophenyl)-N-((trans)-4-methoxy-3,4-dihydro-2H-1-benzopyran-3-yl)-2-[3-(trifluoromethoxy)azetidin-1-yl]acetamide (diastereomer mixture)

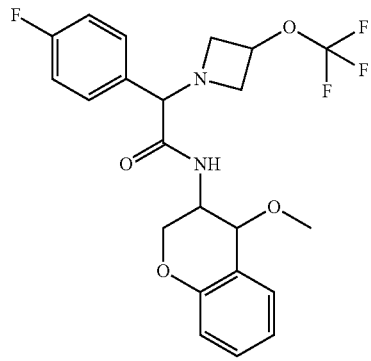 [SMILES: COC1c2ccccc2OCC1NC(=O)C(c1ccc(F)cc1)N1CC(OC(F)(F)F)C1]

Prepared as described for (2S)-N-(4-oxo-3,4-dihydro-2H-1-benzopyran-3-yl)-2-phenylpropanamide (Example 4) using (trans)-4-methoxy-3,4-dihydro-2H-1-benzopyran-3-amine hydrochloride (Intermediate S, 33 mg, 0.184 mmol) and lithium 2-(4-fluorophenyl)-2-(3-(trifluoromethoxy)azetidin-1-yl)acetate (Intermediate J, 55 mg, 0.184 mmol). The crude material was purified by reverse phase preparative HPLC eluted with acetonitrile/water (with 0.1% ammonia) to afford the title compound.

$^1$H NMR (400 MHz, DMSO-$d_6$) δ ppm 2.86-3.14 (m, 2 H), 3.27-3.32 (m, 4 H), 3.48-3.59 (m, 1 H), 3.99-4.29 (m, 5 H), 4.76-4.94 (m, 1 H), 6.85-7.00 (m, 2 H), 7.05-7.19 (m, 2 H), 7.21-7.32 (m, 3 H), 7.34-7.43 (m, 1 H), 7.77-7.98 (m, 1 H)

MS ES$^+$: 455

Example 25: 2-(2,4-difluorophenyl)-N-((trans)-4-methoxy-3,4-dihydro-2H-1-benzopyran-3-yl)-2-[3-(trifluoromethoxy)azetidin-1-yl]acetamide (diastereomer mixture)

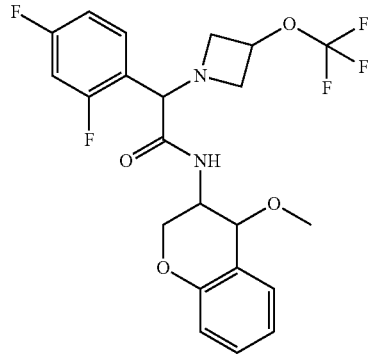 [SMILES: COC1c2ccccc2OCC1NC(=O)C(c1ccc(F)cc1F)N1CC(OC(F)(F)F)C1]

Prepared as described for (2S)-N-(4-oxo-3,4-dihydro-2H-1-benzopyran-3-yl)-2-phenylpropanamide (Example 4) using (trans)-4-methoxy-3,4-dihydro-2H-1-benzopyran-3-amine hydrochloride (Intermediate S, 33 mg, 0.184 mmol) and lithium 2-(2,4-difluorophenyl)-2-(3-(trifluoromethoxy)azetidin-1-yl)acetate (Intermediate K, 22 mg, 0.069 mmol).

The crude material was purified by reverse phase preparative HPLC eluted with acetonitrile/water (with 0.1% ammonia) to afford the title compound.

¹H NMR (400 MHz, DMSO-d₆) δ ppm 2.88-3.03 (m, 1 H), 3.11-3.22 (m, 1 H), 3.35-3.52 (m, 5 H), 4.06-4.28 (m, 4 H), 4.35-4.48 (m, 1 H), 4.80-4.91 (m, 1 H), 6.83-7.59 (m, 8 H), 7.93-8.19 (m, 1 H)

MS ES⁺: 473

Examples 26 and 27: (1S)-2-(3-fluoropropyl)-N-((trans)-4-methoxy-3,4-dihydro-2H-1-benzopyran-3-yl)-3-oxo-1,2,3,4-tetrahydroisoquinoline-1-carboxamide (single stereoisomers)

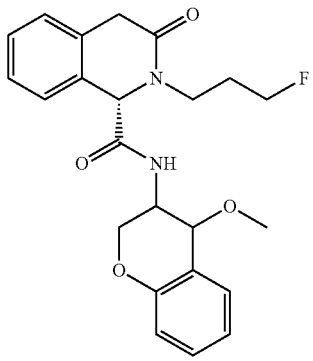 [SMILES: COC1c2ccccc2OCC1NC(=O)[C@@H]1c2ccccc2CC(=O)N1CCCF]

Prepared as described for (2S)—N-(4-oxo-3,4-dihydro-2H-1-benzopyran-3-yl)-2-phenylpropanamide (Example 4) using (trans)-4-methoxy-3,4-dihydro-2H-1-benzopyran-3-amine hydrochloride (Intermediate S, 43 mg, 0.199 mmol) and (1S)-2-(3-fluoropropyl)-3-oxo-1,2,3,4-tetrahydroisoquinoline-1-carboxylic acid (Intermediate L, 50 mg, 0.199 mmol). The crude material was purified by column chromatography on silica, eluted with 0-100% ethyl acetate/petroleum ether. The product was purified by chiral SFC (23% MeOH, ID column) to afford the title compounds.

1. Example 26—1ˢᵗ Eluting Peak

¹H NMR (400 MHz, DMSO-d₆) δ ppm 1.53-1.86 (m, 2 H), 3.11-3.29 (m, 1 H), 3.37-3.48 (m, 5 H), 3.86-3.94 (m, 1 H), 4.02-4.17 (m, 4 H), 4.19-4.39 (m, 2 H), 5.22 (s, 1 H), 6.89-7.02 (m, 2 H), 7.15-7.35 (m, 5 H), 7.44-7.52 (m, 1 H), 8.76-8.82 (m, 1 H)

MS ES⁺: 413

2. Example 27—2ⁿᵈ Eluting Peak

¹H NMR (400 MHz, DMSO-d₆) δ ppm 1.73-1.98 (m, 2 H), 3.12-3.22 (m, 1 H), 3.28 (s, 3 H), 3.39-3.47 (m, 1 H), 3.63-3.72 (m, 1 H), 3.82-3.91 (m, 2 H), 4.07-4.17 (m, 2 H), 4.20-4.27 (m, 1 H), 4.32-4.39 (m, 1 H), 4.43-4.52 (m, 1 H), 5.24 (s, 1 H), 6.90-6.97 (m, 2 H), 7.00-7.07 (m, 2 H), 7.12-7.19 (m, 2 H), 7.20-7.26 (m, 1 H), 7.27-7.33 (m, 1 H), 8.67-8.74 (m, 1 H)

MS ES⁺: 413

Example 28: N-((trans)-4-methoxy-3,4-dihydro-2H-1-benzopyran-3-yl)-2-[(oxan-4-yl)methyl]-3-oxo-1,2,3,4-tetrahydroisoquinoline-1-carboxamide

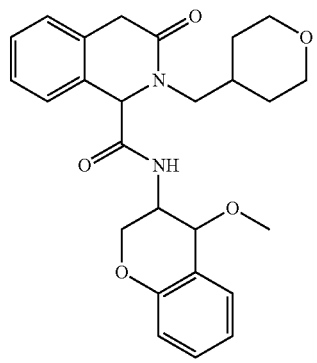 [SMILES: COC1c2ccccc2OCC1NC(=O)C1c2ccccc2CC(=O)N1CC1CCOCC1]

T3P (50% in ethyl acetate, 0.231 mL, 0.389 mmol) was added to a suspension of 3-oxo-2-((tetrahydro-2H-pyran-4-yl)methyl)-1,2,3,4-tetrahydroisoquinoline-1-carboxylic acid (Intermediate M, 0.075 g, 0.259 mmol), (trans)-4-methoxy-3,4-dihydro-2H-1-benzopyran-3-amine hydrochloride (Intermediate S, 0.061 g, 0.285 mmol) and TEA (0.108 mL, 0.778 mmol) in DCM (2 mL). The reaction was stirred at room temperature for 1 hour. A further portion of T3P (50% in EtOAc, 0.231 ml, 0.389 mmol) was added and the reaction stirred for 1 hour. The mixture was partitioned between DCM and saturated NaHCO₃, dried (phase separator) and concentrated in vacuo. The crude product was purified by reverse phase preparative HPLC eluted with acetonitrile/water (with 0.1% ammonia) to afford the title compound.

¹H NMR (400 MHz, DMSO-d₆) δ ppm 0.95-1.52 (m, 4 H), 1.54-1.86 (m, 1 H), 2.71-2.93 (m, 1 H), 3.04-3.25 (m, 2 H), 3.28 (s, 1 H), 3.35-3.60 (m, 4 H), 3.68-4.31 (m, 7 H), 5.21 (s, 1 H), 6.88-7.07 (m, 3 H), 7.12-7.48 (m, 5 H), 8.63-8.80 (m, 1 H)

MS ES⁺: 451

Example 29: N-((trans)-4-methoxy-3,4-dihydro-2H-1-benzopyran-3-yl)-3-oxo-2-[(pyridin-2-yl)methyl]-1,2,3,4-tetrahydroisoquinoline-1-carboxamide

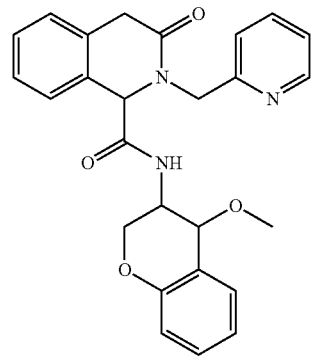 [SMILES: COC1c2ccccc2OCC1NC(=O)C1c2ccccc2CC(=O)N1Cc1ccccn1]

Prepared as described for N-((trans)-4-methoxy-3,4-dihydro-2H-1-benzopyran-3-yl)-2-[(oxan-4-yl)methyl]-3-oxo-1,2,3,4-tetrahydroisoquinoline-1-carboxamide (Example 28) using 3-oxo-2-(pyridin-2-ylmethyl)-1,2,3,4-tetrahydroisoquinoline-1-carboxylic acid (Intermediate N, 0.075 g, 0.266 mmol) and (trans)-4-methoxy-3,4-dihydro-2H-1-benzopyran-3-amine hydrochloride (Intermediate S, 0.063 g, 0.292 mmol). The crude material was purified by reverse phase preparative HPLC eluted with acetonitrile/water (with 0.1% ammonia) to afford the title compound.

$^1$H NMR (400 MHz, CD$_2$Cl$_2$) δ ppm 3.25-3.31 (m, 1 H), 3.39-3.53 (m, 4 H), 3.92-3.99 (m, 1 H), 4.09-4.37 (m, 3 H), 4.45-4.89 (m, 2 H), 4.97-5.04 (m, 1 H), 6.84-7.36 (m, 10 H), 7.53-7.71 (m, 1 H), 8.30-8.47 (m, 1 H), 8.55-8.65 (m, 1 H)

MS ES$^+$: 444

Example 30: 2-(cyclopropylmethoxy)-2-(4-fluorophenyl)-N-((trans)-4-methoxy-3,4-dihydro-2H-1-benzopyran-3-yl)acetamide

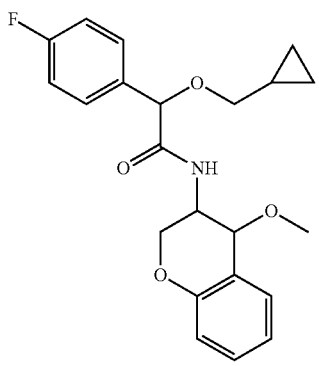 [SMILES: COC1c2ccccc2OCC1NC(=O)C(OCC1CC1)c1ccc(F)cc1]

Prepared as described for N-((trans)-4-methoxy-3,4-dihydro-2H-1-benzopyran-3-yl)-2-[(oxan-4-yl)methyl]-3-oxo-1,2,3,4-tetrahydroisoquinoline-1-carboxamide (Example 28) using 2-(cyclopropylmethoxy)-2-(4-fluorophenyl)acetic acid (Intermediate O, 0.1 g, 0.446 mmol) and (trans)-4-methoxy-3,4-dihydro-2H-1-benzopyran-3-amine hydrochloride (Intermediate S, 0.106 g, 0.491 mmol). The crude material was purified by reverse phase preparative HPLC eluted with acetonitrile/water (with 0.1% ammonia) to afford the title compound.

$^1$H NMR (400 MHz, DMSO-d$_6$) δ ppm 0.01-0.13 (m, 2 H), 0.28-0.46 (m, 2 H), 0.76-1.01 (m, 1 H), 3.04-3.25 (m, 2 H), 3.35-3.38 (m, 3 H), 4.06-4.31 (m, 4 H), 4.80-4.93 (m, 1 H), 6.82-7.03 (m, 2 H), 7.08-7.21 (m, 2 H), 7.23-7.44 (m, 4 H), 7.74-7.96 (m, 1 H)

MS ES$^-$: 384

Example 31: 2-(2,4-difluorophenyl)-N-((trans)-4-methoxy-3,4-dihydro-2H-1-benzopyran-3-yl)-2-[(2-methylpyrimidin-4-yl)oxy]acetamide

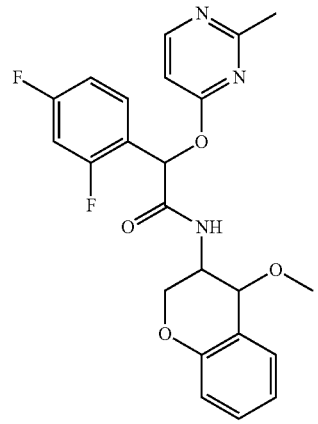 [SMILES: COC1c2ccccc2OCC1NC(=O)C(Oc1ccnc(C)n1)c1ccc(F)cc1F]

Prepared as described for N-((trans)-4-methoxy-3,4-dihydro-2H-1-benzopyran-3-yl)-2-[(oxan-4-yl)methyl]-3-oxo-1,2,3,4-tetrahydroisoquinoline-1-carboxamide (Example 28) using 2-(2,4-difluorophenyl)-2-((2-methylpyrimidin-4-yl)oxy)acetic acid (Intermediate P, 0.066 g, 0.236 mmol) and (trans)-4-methoxy-3,4-dihydro-2H-1-benzopyran-3-amine hydrochloride (Intermediate S, 0.056 g, 0.259 mmol). The crude material was purified by reverse phase preparative HPLC eluted with acetonitrile/water (with 0.1% ammonia) to afford the title compound.

$^1$H NMR (400 MHz, DMSO-d$_6$) δ ppm 2.32-2.50 (m, 3 H), 3.33-3.42 (m, 3 H), 4.03-4.30 (m, 4 H), 6.45 (d, J=11.74 Hz, 1 H), 6.75-7.01 (m, 3 H), 7.05-7.38 (m, 4 H), 7.43-7.59 (m, 1 H), 8.38-8.47 (m, 1 H), 8.57-8.75 (m, 1 H)

MS ES$^+$: 442

Example 32: 2-(2,4-difluorophenyl)-N-((trans)-4-methoxy-3,4-dihydro-2H-1-benzopyran-3-yl)-2-(2-oxo-1,2-dihydropyridin-1-yl)acetamide

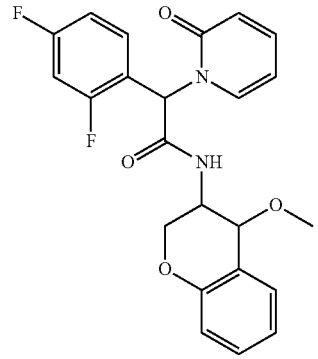 [SMILES: COC1c2ccccc2OCC1NC(=O)C(c1ccc(F)cc1F)n1ccccc1=O]

Prepared as described for N-((trans)-4-methoxy-3,4-dihydro-2H-1-benzopyran-3-yl)-2-[(oxan-4-yl)methyl]-3-oxo-1,2,3,4-tetrahydroisoquinoline-1-carboxamide (Example 28) using 2-(2,4-difluorophenyl)-2-(2-oxopyridin-1 (2H)-yl)acetic acid (Intermediate Q, 0.075 g, 0.283 mmol) and (trans)-4-methoxy-3,4-dihydro-2H-1-benzopyran-3-amine hydrochloride (Intermediate S, 0.067 g, 0.311 mmol).

The crude material was purified column chromatography on silica, eluted with 0-100% ethyl acetate/petroleum ether to afford the title compound.

$^1$H NMR (400 MHz, CD$_2$Cl$_2$) δ ppm 3.47-3.53 (m, 3 H), 4.06-4.46 (m, 4 H), 6.04-6.15 (m, 1 H), 6.28-6.37 (m, 1 H), 6.69-7.04 (m, 5 H), 7.09-7.54 (m, 6 H)

MS ES$^+$: 427

Examples 33 and 34: N$^1$-(trans)-{3-[(2S)-2-(4-fluorophenyl)propanamido]-3,4-dihydro-2H-1-benzopyran-4-yl}-N$^2$-methylbenzene-1,2-dicarboxamide (single stereoisomers)

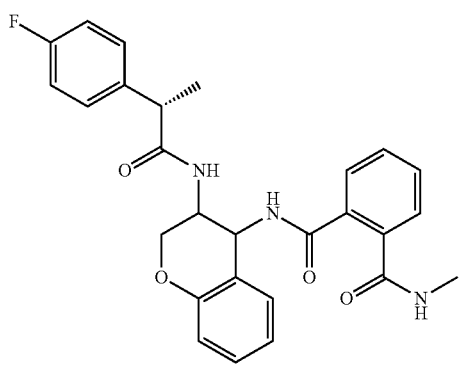 [SMILES: CNC(=O)c1ccccc1C(=O)NC1c2ccccc2OCC1NC(=O)[C@@H](C)c1ccc(F)cc1]

Methanamine (40% in water, 0.543 mL, 6.28 mmol) was added to a stirred solution of (2S)—N-[(trans)-4-(1,3-dioxo-2,3-dihydro-1H-isoindol-2-yl)-3,4-dihydro-2H-1-benzopyran-3-yl]-2-(4-fluorophenyl)propanamide (Intermediate R, 62 mg, 0.139 mmol) in ethanol (0.5 mL). The reaction was stirred at room temperature for 2 hours. The reaction was concentrated in vacuo and purified by reverse phase preparative HPLC eluted with acetonitrile/water (with 0.1% ammonia) to afford the title compounds.

1. Example 33—1$^{st}$ Eluting Peak $^1$H NMR (400 MHz, DMSO-d$_6$) δ ppm 1.34 (d, J=6.97 Hz, 3 H), 2.74 (d, J=4.58 Hz, 3 H), 3.65-3.75 (m, 1 H), 3.93-4.03 (m, 1 H), 4.11-4.24 (m, 2 H), 5.11-5.21 (m, 1 H), 6.75-6.85 (m, 2 H), 6.88-6.97 (m, 1 H), 7.00-7.09 (m, 2 H), 7.12-7.21 (m, 1 H), 7.24-7.30 (m, 1 H), 7.32-7.53 (m, 5 H), 8.13-8.26 (m, 2 H), 8.54-8.62 (m, 1 H)

MS ES$^+$: 476

2. Example 34—2$^{nd}$ Eluting Peak $^1$H NMR (400 MHz, DMSO-d$_6$) δ ppm 1.32 (d, J=7.70 Hz, 1 H), 2.77 (d, J=4.58 Hz, 3 H), 3.67-3.77 (m, 1 H), 3.85-3.97 (m, 1 H), 4.05-4.25 (m, 2 H), 5.14-5.25 (m, 1 H), 6.75-6.84 (m, 1 H), 6.89-6.98 (m, 1 H), 7.07-7.18 (m, 3 H), 7.30-7.37 (m, 2 H), 7.39-7.53 (m, 5 H), 8.05-8.14 (m, 1 H), 8.25-8.33 (m, 1 H), 8.71-8.80 (m, 1 H)

MS ES$^+$: 476

Example 35: (2S)-2-(4-fluorophenyl)-N-[(trans)-4-(pyrrolidin-1-yl)-3,4-dihydro-2H-1-benzopyran-3-yl]propanamide (single stereoisomer)

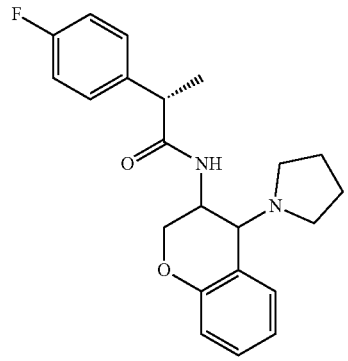 [SMILES: C[C@H](C(=O)NC1COc2ccccc2C1N1CCCC1)c1ccc(F)cc1]

Methanesulfonic anhydride (110 mg, 0.634 mmol) was added to a dry ice/acetone cooled solution of (2S)-2-(4-fluorophenyl)-N-((cis)-4-hydroxy-3,4-dihydro-2H-1-benzopyran-3-yl)propanamide (Intermediate I, 100 mg, 0.317 mmol) and TEA (0.133 mL, 0.951 mmol) in THF (3 mL). The reaction mixture was stirred at this temperature for 10 minutes. The cooling bath was switched for an ice bath. After 30 minutes, pyrrolidine (0.132 mL, 1.586 mmol) was added. The reaction was stirred in the ice bath for 30 minutes and then allowed to warm to room temperature and stirred for 24 hours. The reaction mixture was partitioned between DCM and water and the organic phase was purified by reverse phase preparative HPLC eluted with acetonitrile/water (with 0.1% ammonia) to afford the title compound.

$^1$H NMR (400 MHz, DMSO-d$_6$) δ 1.22 (d, J=6.97 Hz, 3 H), 1.61-1.70 (m, 3 H), 2.37-2.45 (m, 2 H), 2.66-2.78 (m, 2 H), 3.30-3.32 (m, 1 H), 3.35-3.38 (m, 1 H), 3.63-3.72 (m, 1 H), 3.91-4.00 (m, 1 H), 4.22-4.32 (m, 2 H), 6.77-6.90 (m, 2 H), 7.06-7.14 (m, 2 H), 7.15-7.25 (m, 2 H), 7.28-7.37 (m, 2 H), 7.99 (d, J=7.06 Hz, 1 H)

MS ES$^+$: 369

Example 36: (2S)—N-[(trans)-4-(azetidin-1-yl)-3,4-dihydro-2H-1-benzopyran-3-yl]-2-(4-fluorophenyl)propanamide (single stereoisomer)

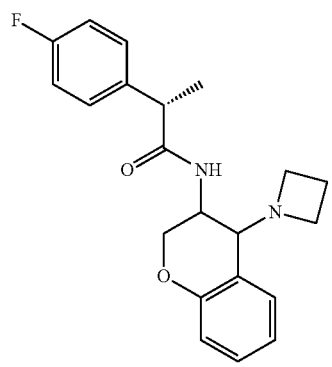 [SMILES: C[C@H](C(=O)NC1COc2ccccc2C1N1CCC1)c1ccc(F)cc1]

Prepared as described for (2S)-2-(4-fluorophenyl)-N-[(trans)-4-(pyrrolidin-1-yl)-3,4-dihydro-2H-1-benzopyran-3-yl]propanamide (Example 35) using (2S)-2-(4-fluorophenyl)-N-((cis)-4-hydroxy-3,4-dihydro-2H-1-benzopyran-3-yl)propanamide (Intermediate I, 100 mg, 0.317 mmol) and azetidine (0.107 mL, 1.586 mmol). The crude material was purified by reverse phase preparative HPLC eluted with acetonitrile/water (with 0.1% ammonia) to afford the title compound.

$^1$H NMR (400 MHz, DMSO-$d_6$) δ 1.22 (d, J=7.06 Hz, 3 H), 1.84-1.96 (m, 2 H), 3.01-3.09 (m, 2 H), 3.10-3.16 (m, 1 H), 3.35-3.43 (m, 2 H), 3.65-3.75 (m, 1 H), 3.84-3.98 (m, 2 H), 4.22-4.31 (m, 1 H), 6.78-6.89 (m, 2 H), 7.03-7.12 (m, 2 H), 7.16-7.23 (m, 2 H), 7.28-7.35 (m, 2 H), 8.07 (d, J=6.97 Hz, 1 H)

MS ES$^+$: 355

Example 37: (2S)—N-[(trans)-4-(dimethylamino)-3,4-dihydro-2H-1-benzopyran-3-yl]-2-(4-fluorophenyl)propanamide (single stereoisomer)

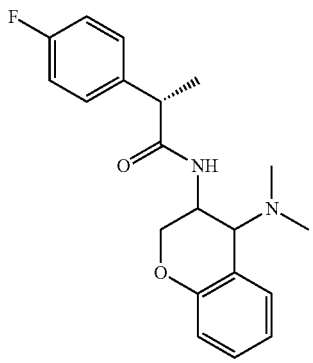 [SMILES: C[C@H](C(=O)NC1COc2ccccc2C1N(C)C)c1ccc(F)cc1]

Prepared as described for (2S)-2-(4-fluorophenyl)-N-[(trans)-4-(pyrrolidin-1-yl)-3,4-dihydro-2H-1-benzopyran-3-yl]propanamide (Example 35) using (2S)-2-(4-fluorophenyl)-N-((cis)-4-hydroxy-3,4-dihydro-2H-1-benzopyran-3-yl)propanamide (Intermediate I, 100 mg, 0.317 mmol) and dimethylamine (2 M solution in THF, 0.793 mL, 1.586 mmol). The crude material was purified by reverse phase preparative HPLC eluted with acetonitrile/water (with 0.1% ammonia) to afford the title compound.

$^1$H NMR (400 MHz, DMSO-$d_6$) δ 1.26-1.36 (m, 3 H), 2.26 (s, 6 H), 3.59-3.68 (m, 2 H), 3.92 (s, 2 H), 4.21-4.33 (m, 1 H), 6.73-6.83 (m, 1 H), 6.87-6.96 (m, 1 H), 7.09-7.20 (m, 3 H), 7.30-7.41 (m, 3 H), 8.09-8.18 (m, 1 H)

MS ES$^+$: 343

Example 38: (2S)—N-[(trans)-4-(3,3-difluoropyrrolidin-1-yl)-3,4-dihydro-2H-1-benzopyran-3-yl]-2-(4-fluorophenyl)propanamide (single stereoisomer)

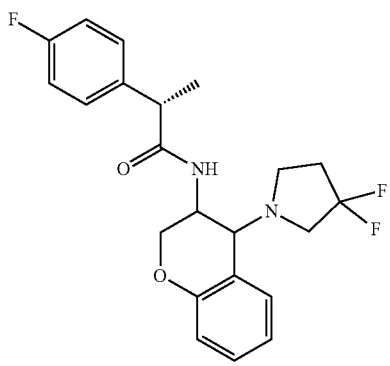 [SMILES: C[C@H](C(=O)NC1COc2ccccc2C1N1CCC(F)(F)C1)c1ccc(F)cc1]

Methanesulfonic anhydride (110 mg, 0.634 mmol) was added to a dry ice/acetone cooled solution of (2S)-2-(4-fluorophenyl)-N-((cis)-4-hydroxy-3,4-dihydro-2H-1-benzopyran-3-yl)propanamide (Intermediate I, 100 mg, 0.317 mmol) and TEA (0.133 mL, 0.951 mmol) in THF (3 mL). The reaction mixture was stirred at this temperature for 10 minutes. The cooling bath was switched for an ice bath. After 15 minutes, 3,3-difluoropyrrolidine hydrochloride (228 mg, 1.586 mmol) and TEA (0.221 mL, 1.586 mmol) were added. The reaction was stirred in the ice bath for 30 minutes and then allowed to warm to room temperature and stirred for 24 hours. The reaction mixture was partitioned between DCM and water and the organic phase was purified by reverse phase preparative HPLC eluted with acetonitrile/water (with 0.1% ammonia) to afford the title compound.

$^1$H NMR (400 MHz, DMSO-$d_6$) δ 1.23 (d, J=7.06 Hz, 3 H), 2.12-2.27 (m, 2 H), 2.63-2.73 (m, 1 H), 2.77-2.89 (m, 1 H), 2.92-3.01 (m, 1 H), 3.17-3.29 (m, 1 H), 3.53-3.57 (m, 1 H), 3.63-3.70 (m, 1 H), 3.93-4.00 (m, 1 H), 4.17-4.26 (m, 2 H), 6.81-6.86 (m, 1 H), 6.87-6.94 (m, 1 H), 7.07-7.14 (m, 2 H), 7.19-7.25 (m, 1 H), 7.27-7.39 (m, 3 H), 8.13 (d, J=6.97 Hz, 1 H)

MS ES$^+$: 405

Example 39: (2S)-2-(4-fluorophenyl)-N-[(trans)-4-(morpholin-4-yl)-3,4-dihydro-2H-1-benzopyran-3-yl]propanamide (single stereoisomer)

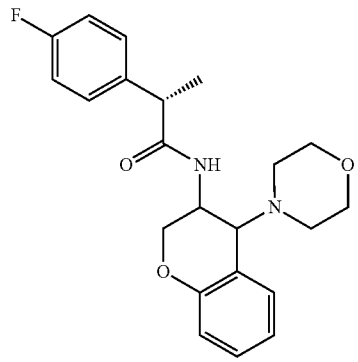 [SMILES: C[C@H](C(=O)NC1COc2ccccc2C1N1CCOCC1)c1ccc(F)cc1]

Prepared as described for (2S)-2-(4-fluorophenyl)-N-[(trans)-4-(pyrrolidin-1-yl)-3,4-dihydro-2H-1-benzopyran-3-yl]propanamide (Example 35) using (2S)-2-(4-fluorophenyl)-N-((cis)-4-hydroxy-3,4-dihydro-2H-1-benzopyran-3-yl)propanamide (Intermediate I, 100 mg, 0.317 mmol) and morpholine (0.139 mL, 1.586 mmol). The crude material was purified by reverse phase preparative HPLC eluted with acetonitrile/water (with 0.1% ammonia) to afford the title compound.

$^1$H NMR (400 MHz, DMSO-$d_6$) δ ppm 1.29 (d, J=7.06 Hz, 3 H), 2.40-2.48 (m, 2 H), 2.53-2.62 (m, 2 H), 3.43-3.58 (m, 4 H), 3.60-3.72 (m, 2 H), 3.80-3.90 (m, 1 H), 3.92-4.02 (m, 1 H), 4.17-4.32 (m, 1 H), 6.74-6.83 (m, 1 H), 6.86-6.98 (m, 1 H), 7.07-7.21 (m, 3 H), 7.29-7.38 (m, 2 H), 7.43 (d, J=7.79 Hz, 1 H), 8.16 (d, J=7.89 Hz, 1 H)

MS ES$^+$: 385

Example 40: Biological Efficacy Shown by a mGluR7 Assay

The ability of the test compounds to activate mGluR7 was determined by their ability to reduce forskolin stimulated cAMP production. Compounds were assessed in a CRE-directed luciferase reporter gene assay, using a stable CHO cell line expressing the CRE-luc reporter and human mGluR7 genes. In this cell line, production of cAMP stimulated the transcription of the luciferase gene and luciferase activity was then measured in a luminescent enzyme assay (Steady Glo assay; Promega E2550). Activation of mGluR7 decreased the forskolin stimulated luminescence signal.

The day prior to the assay, compounds were serially diluted in DMSO (100× final assay concentration (FAC)), in 384-well plates which were then stored in the dark at room temperature (RT) until use. Cells were seeded at 12.5 k/well in white, clear bottom 384-well plates (Corning 3707) and left for one hour at RT followed by an overnight incubation (37° C.). The following day, the DMSO compound plate was diluted 1:20 (5×FAC) in Opti-MEM I (Life Technologies 11058021). The growth media was removed from the cell plate and replaced with 15 µl Opti-MEM I, followed by a 5 µl addition from the 5× compound plate and a fifteen minute incubation (37° C.). Forskolin (Sigma F3917) was then added to the wells (5 µl of 2.5 µM) and the plate was incubated for five hours (37° C.). During this incubation, the Steady Glo Substrate reagent was warmed to 37° C. Aliquots (11 ml; stored at −20° C.) of this reagent were prepared by dissolving the contents of 1 vial of lyophilised substrate in 100 ml Steady-Glo buffer. A 25 µl addition of the substrate was made to all wells and the plate was incubated for thirty minutes at RT, on a plate shaker (300 rpm; in the dark). Luminescence was then measured using the EnVision Multilabel Reader (Perkin Elmer).

Compound activity was examined using a 10-point, half log concentration-response range and each concentration was tested in duplicate wells. Luminescence values were normalised to 'maximum' (forskolin alone) and 'minimum' (forskolin in the presence of tool mGluR7 agonist) controls. $EC_{50}$ values were derived from this data using non-linear regression and a four parameter curve fit. The $EC_{50}$ values for the compounds of the Examples are shown in Table 1.

TABLE 1

Assay results

| Example Number | $EC_{50}$ (nM) | Example Number | $EC_{50}$ (nM) | Example Number | $EC_{50}$ (nM) |
| --- | --- | --- | --- | --- | --- |
| 1 | 874 | 2 | 96 | 3 | 1,205 |
| 4 | 860 | 5 | 68 | 6 | 101 |
| 7 | 911 | 8 | 274 | 9 | 4,985 |
| 10 | 1,648 | 11 | 55 | 12 | 7 |
| 13 | 26 | 14 | 65 | 15 | 14 |
| 16 | 7 | 17 | 28 | 18 | 15 |
| 19 | 6 | 20 | 10 | 21 | 33 |
| 22 | 69 | 23 | 110 | 24 | 20 |
| 25 | 27 | 26 | 23 | 27 | 22 |
| 28 | 14 | 29 | 8 | 30 | 11 |
| 31 | 54 | 32 | 300 | 33 | 700 |
| 34 | 97 | 35 | 62 | 36 | 33 |
| 37 | 55 | 38 | 30 | 39 | 23 |

Example 42: Selectivity and Desensitization Profile of the Compound in Example 16

The compound in Example 16, (2S)-2-(4-fluorophenyl)-N-((trans)-4-methanesulfonyl-3,4-dihydro-2H-1-benzopyran-3-yl)propanamide (CPD1), was observed to be a full agonist at mGluR7 in human and mouse samples, whilst having no activity at mGluR4 and mGluR8 as shown in FIG. 1A and in Table 2 (data are mean±standard deviation, n=2 in FIG. 1A and Table 2). The activation of mGluR7 was measured by the decreased forskolin stimulated luminescence signal. As shown in FIG. 1A, activation of human mGluR7 and mouse mGluR7 decreased the forskolin stimulated luminescence signal. Forskolin stimulated luminescence signal was not reduced for mGluR4 and mGluR8.

TABLE 2

Selectivity assay

| | mGluR7 (human) | mGluR7 (mouse) | mGluR4 | mGluR8 |
| --- | --- | --- | --- | --- |
| EC50 (nM) | 6.9 ± 0.8 | 1.8 ± 3.5 | inactive (≤10 µM) | inactive (≤10 µM) |
| Emax (% control) | 100 ± 1.8 | 100 ± 0.1 | inactive (≤10 µM) | inactive (≤10 µM) |

In the kinetic impedance assay, pre-treatment with AMN082 (1 hour) was observed to considerably reduce subsequent responses to CPD A (Emax reduced by 75%, $EC_{50}$ increased 5-fold), whereas pre-treatment with the compound of Example 16 did not alter the response to CPD A. Results are shown in FIG. 1B.

Example 43: In Vitro Mode of Action for the Compound of Example 16

Figure 2B:
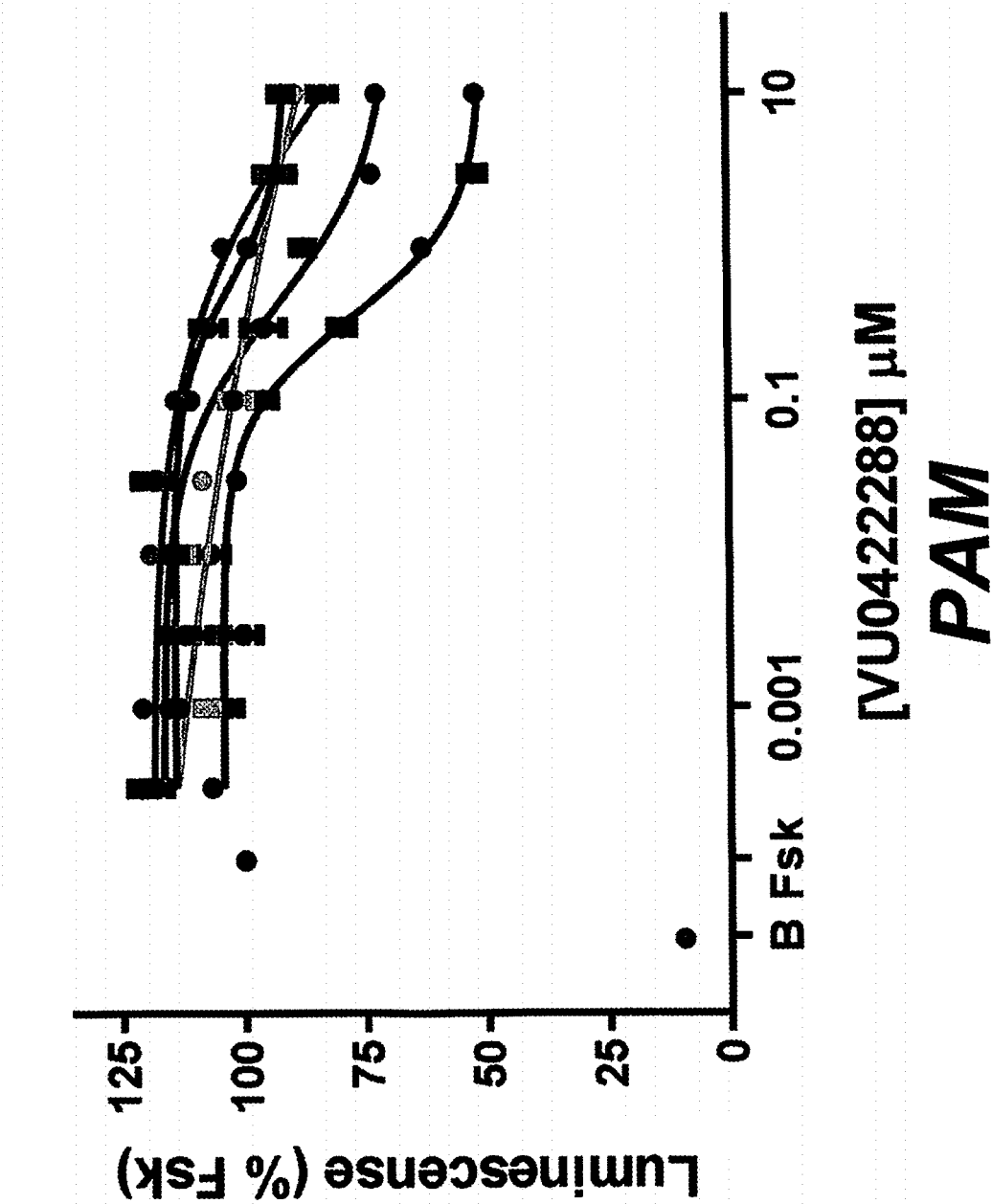

The mode of action of the compound in Example 16 was determined by testing activity in the presence of the orthosteric antagonist LY341495 (LY). Whereas increasing LY concentrations reduced the potency of an orthosteric antagonist as shown in FIG. 2A and the $E_{max}$ of a PAM as shown in FIG. 2B, no effect was seen on an allosteric agonist (see FIG. 2C). CPD1 activity was unaffected by LY as shown in FIG. 2D, suggesting it is also an allosteric agonist.

Example 44: Modulation of Glutamate Release and Synaptic Plasticity

Figure 3A:
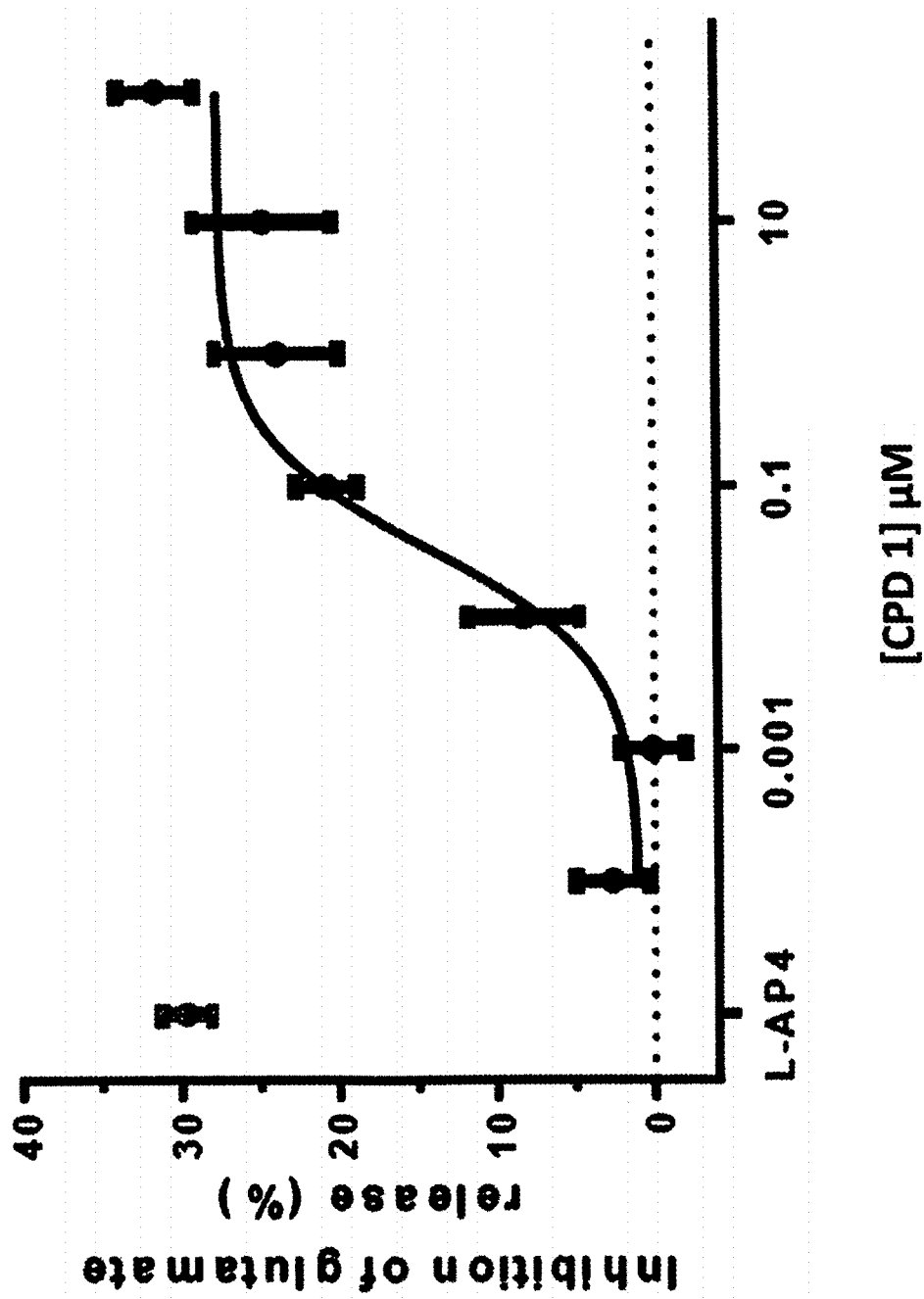
FIG. 3A is a graph showing the results of a glutamate release assay for CPD1 in mouse synaptosomes.
Figure 3D:
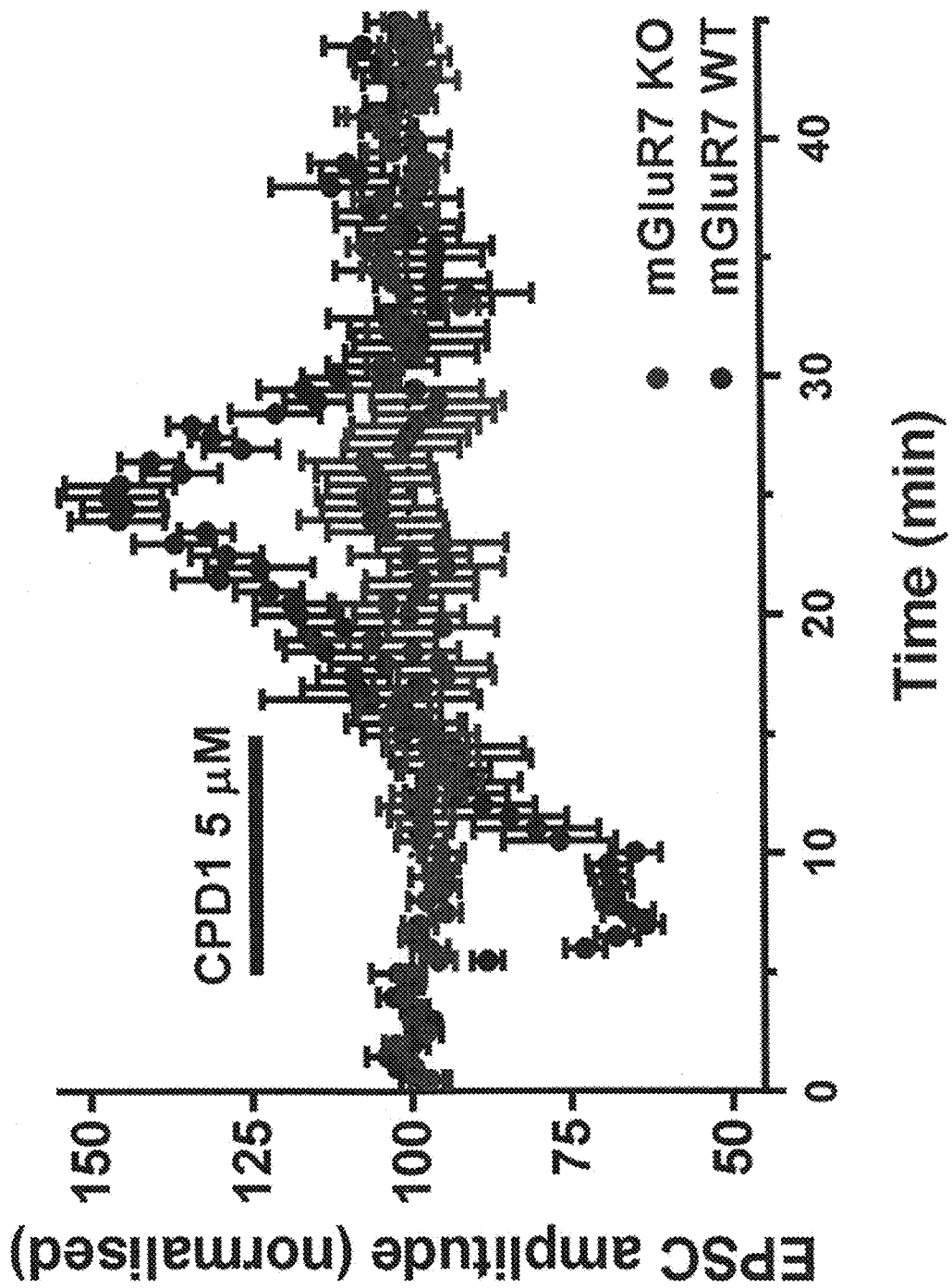

For short incubations (1 minute), CPD1 was observed to reduce glutamate release from mouse cortical synaptosomes by 30% ($EC_{50}$ 34 nM) as shown in FIG. 3A. With longer exposures (10 minutes), CPD1 was observed to enhance glutamate release by 92% as shown in FIG. 3B. Electrophysiological recordings from mouse hippocampal slices in FIG. 3C showed CPD1 had a bimodal effect on excitatory postsynaptic currents (EPSCs), initially reducing and then enhancing the amplitude. In contrast, CPD1 appeared inactive in slices from mGluR7 KO mice as shown in FIG. 3D.

CPD1 is a potent (low nM) and selective (vs mGluR4, 8) mGluR7 agonist, which, like AMN082, acts allosterically. In contrast to AMN082, in vitro desensitization effects were not observed for CPD1. In native tissue, CPD1 modulated neurotransmitter release and synaptic activity with a similar profile to L-AP4 (non-selective agonist). Unlike L-AP4, the effects of CPD1 on synaptic activity were observed to be entirely mGluR7 specific.

REFERENCES

The references cited herein are listed below. Each cited reference is herein incorporated by reference in its entirety.
1. O'Connor R. M., Finger B. C., Flor P. J. and Cryan J. F., 2010. Metabotropic glutamate receptor 7: at the interface of cognition and emotion. *Eur J Pharmacol.*, 639 (1-3), 123-31.
2. Konieczny J. and Lenda T., 2013 Contribution of the mGluR7 receptor to antiparkinsonian-like effects in rats: a behavioral study with the selective agonist AMN082. *Pharmacol Rep.*, 65 (5), 1194-1203.
3. Greco B., Lopez S., van der Putten H. and Flor P. J., 2010. Amalric M. Metabotropic glutamate 7 receptor subtype modulates motor symptoms in rodent models of Parkinson's disease. *J Pharmacol Exp Ther.*, 332 (3), 1064-71.
4. Bradley S. R., Standaert D. G., Levey A. I. and Conn P. J., 1999. Distribution of group III mGluRs in rat basal ganglia with subtype-specific antibodies. *Ann NY Acad Sci.*, 868, 531-4.
5. Conn P. J. and Niswender C. M., 2006. mGluR7's lucky number. *Proceedings of the National Academy of Sciences of the United States of America*, 103 (2), 251-2.
6. Hovelsø N., Sotty F., Montezinho L., Pinheiro P., Herrik K. and Mørk A.,2012. Therapeutic Potential of Metabotropic Glutamate Receptor Modulators. *Curr Neuropharmacol.*, 10 (1), 12-48.
7. Kandaswamy R., McQuillin A., Curtis D. and Gurling H., 2014. Allelic Association, DNA Resequencing and Copy Number Variation at the Metabotropic Glutamate Receptor GRM7 Gene Locus in Bipolar Disorder. *Am J Med Genet B Neuropsychiatr Genet.*, 165 (4), 365-72.
8. Palucha-Poniewiera A., Szewczyk B. and Pilc A, 2014. Activation of the mTOR signaling pathway in the antidepressant-like activity of the mGlu5 antagonist MTEP and the mGlu7 agonist AMN082 in the FST in rats. *Neuropharmacology*, 82, 59-68.
9. Palucha A., Klak K., Branski P., van der Putten H., Flor P. J. and Pilc A., 2007. Activation of the mGlu7 receptor elicits antidepressant-like effects in mice. *Psychopharmacology (Berl).*, 194 (4), 555-62.
10. Kalinichev M., Rouillier M., Girard F., Royer-Urios I., Bournique B., Finn T. et al., 2013. ADX71743, a potent and selective negative allosteric modulator of metabotropic glutamate receptor 7: in vitro and in vivo characterization. *J Pharmacol Exp Ther.*, 344 (3), 624-36.
11. Bolonna A. A., Kerwin R. W., Munro J., Arranz M. J., Makoff A. J., 2001. Polymorphisms in the genes for mGluR types 7 and 8: association studies with schizophrenia. *Schizophr Res.*, 47 (1), 99-103.
12. Friedman, R. A., et al., 2009. GRM7 variants confer susceptibility to age-related hearing impairment. *Hum Mol Genet* 18(4), 785-796.
13. Bradley S. R. et al. (1998). *J. Neurochem.* 71: 636-45.
14. Palazzo E. et al. (2016). *Curr. Neuropharmacol.* 14: 504-513.
15. Martin R. et al. (2010). *J. Biol. Chem.* 285: 17907-1791.7.
16. Abe et al. (2017). Discovery of VU6005649, a CNS Penetrant mGlu7/8 Receptor PAM Derived from a Series of Pyrazolo[1,5-a]pyrimidines. *ACS Med. Chem. Lett.* DOI: 10.1021/acsmedchemlett.7b00317.

The invention claimed is:
1. A compound of formula (I) or a pharmaceutically acceptable salt thereof

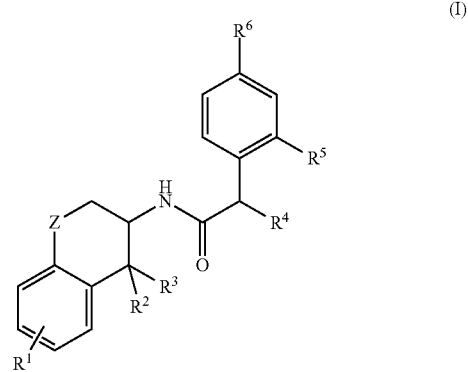

wherein
 $R^1$ represents hydrogen or halogen;
 $R^2$ represents hydrogen, hydroxyl, $C_1$-$C_6$ alkyl, $C_1$-$C_6$ haloalkyl, $C_1$-$C_6$ alkoxy, $C_1$-$C_6$ haloalkoxy, —N($R^7$)$_2$ or —SO$_2$$R^8$;
 $R^3$ represents hydrogen or $C_1$-$C_3$ alkyl;
 or $R^2$ and $R^3$ together form =O;
 $R^4$ represents cyano, hydroxyl, —N($R^9$)$_2$, $C_1$-$C_6$ alkyl, $C_3$-$C_6$ cycloalkyl, $C_1$-$C_6$ alkoxy, $C_3$-$C_6$ cycloalkoxy, $C_1$-$C_6$ alkylcarbonyl, $C_3$-$C_6$ cycloalkylcarbonyl, $C_1$-$C_6$ alkoxycarbonyl, $C_3$-$C_6$ cycloalkoxycarbonyl, —(CH$_2$)$_m$$R^{10}$, —O(CH$_2$)$_m$$R^{10}$ or —NH(CH$_2$)$_m$$R^{10}$, wherein each of the alkyl, cycloalkyl, alkoxy, cycloalkoxy, alkylcarbonyl, cycloalkylcarbonyl, alkoxycarbonyl and cycloalkoxycarbonyl moieties is independently unsubstituted or substituted with at least one substituent independently selected from halogen, cyano, hydroxyl, oxo, methylamino, dimethylamino, $C_1$-$C_3$ alkyl, $C_1$-$C_3$ haloalkyl, $C_1$-$C_3$ alkoxy and $C_1$-$C_3$ haloalkoxy;
 $R^5$ represents hydrogen or halogen;
 or $R^4$ and $R^5$ together with the benzyl group to which they are attached form a 5- to 7-membered carbocyclic or heterocyclic ring, the heterocyclic ring comprising at least one ring heteroatom independently selected from nitrogen, oxygen and sulphur atoms, wherein the carbocyclic or heterocyclic ring is unsubstituted or substituted with at least one substituent independently selected from halogen, cyano, hydroxyl, oxo, amino, methylamino, dimethylamino, $C_1$-$C_6$ alkyl, $C_1$-$C_6$ haloalkyl, $C_1$-$C_6$ alkoxy, $C_1$-$C_6$ haloalkoxy, —(CH$_2$)$_n$$R^{11}$ and —O(CH$_2$)$_n$$R^{11}$; provided that either:
 (i) the heterocyclic ring comprises at least one ring nitrogen atom and the heterocyclic or carbocyclic ring is substituted with two, three, four, five, six or seven substituents independently selected from halogen, cyano, hydroxyl, oxo, amino, methylamino, dimethylamino, $C_1$-$C_6$ alkyl, $C_1$-$C_6$ haloalkyl, $C_1$-$C_6$ alkoxy, $C_1$-$C_6$ haloalkoxy, —(CH$_2$)$_n$$R^{11}$ and —O(CH$_2$)$_n$$R^{11}$; or
 (ii) the carbocyclic or heterocyclic ring is substituted with oxo and with at least one further substituent independently selected from halogen, cyano, hydroxyl, oxo, amino, methylamino, dimethylamino, $C_1$-$C_6$ alkyl, $C_1$-$C_6$ haloalkyl, $C_1$-$C_6$ alkoxy, $C_1$-$C_6$ haloalkoxy, —(CH$_2$)$_n$$R^{11}$ and —O(CH$_2$)$_n$$R^{11}$; or
 (iii) the carbocyclic or heterocyclic ring comprises one double bond and is substituted with oxo and optionally with at least one further substituent independently selected from halogen, cyano, hydroxyl, oxo, amino, methylamino, dimethylamino, $C_1$-$C_6$ alkyl, $C_1$-$C_6$ haloalkyl, $C_1$-$C_6$ alkoxy, $C_1$-$C_6$ haloalkoxy, —$(CH_2)_nR^{11}$ and —$O(CH_2)_nR^{11}$;

$R^6$ represents hydrogen, halogen, $C_1$-$C_6$ alkyl or $C_1$-$C_6$ haloalkyl;

$R^7$ independently represents hydrogen, $C_1$-$C_6$ alkyl, $C_1$-$C_6$ haloalkyl, $C_4$-$C_6$ cycloalkyl, ($C_3$-$C_6$ cycloalkyl)methyl, 4- to 6-membered heterocycloalkyl, (3- to 6-membered heterocycloalkyl)methyl or —$COR^{12}$, or two $R^7$ together with the nitrogen atom to which they are attached form a saturated or unsaturated 4- to 7-membered heterocyclic ring optionally comprising one or more further ring heteroatoms independently selected from nitrogen, oxygen and sulphur atoms, the heterocyclic ring being unsubstituted or substituted with at least one substituent independently selected from halogen, cyano, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy;

$R^8$ represents $C_1$-$C_3$ alkyl, $C_3$-$C_6$ cycloalkyl or ($C_3$-$C_6$ cycloalkyl)methyl;

$R^9$ independently represents methyl, $C_3$-$C_6$ alkyl or $C_1$-$C_6$ haloalkyl, or two $R^9$ together with the nitrogen atom to which they are attached form a saturated or unsaturated 4- to 7-membered heterocyclic ring optionally comprising one or more further ring heteroatoms independently selected from nitrogen, oxygen and sulphur atoms, the heterocyclic ring being unsubstituted or substituted with at least one substituent independently selected from halogen, cyano, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy;

$R^{10}$ represents a saturated or unsaturated 3- to 7-membered carbocyclic ring or a saturated or unsaturated 4- to 7-membered heterocyclic ring, the heterocyclic ring comprising at least one ring heteroatom independently selected from nitrogen, oxygen and sulphur atoms, wherein the carbocyclic or heterocyclic ring is unsubstituted or substituted with at least one substituent independently selected from halogen, cyano, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy;

$R^{11}$ represents a saturated or unsaturated 3- to 7-membered carbocyclic ring or a saturated or unsaturated 4- to 7-membered heterocyclic ring, the heterocyclic ring comprising at least one ring heteroatom independently selected from nitrogen, oxygen and sulphur atoms, wherein the carbocyclic or heterocyclic ring is unsubstituted or substituted with at least one substituent independently selected from halogen, cyano, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy;

$R^{12}$ represents a saturated or unsaturated 3- to 7-membered carbocyclic ring or a saturated or unsaturated 4- to 7-membered heterocyclic ring, the heterocyclic ring comprising at least one ring heteroatom independently selected from nitrogen, oxygen and sulphur atoms, wherein the carbocyclic or heterocyclic ring is unsubstituted or substituted with at least one substituent independently selected from halogen, cyano, hydroxyl, oxo, amino, methylamino, dimethylamino, $C_1$-$C_3$ alkyl, $C_1$-$C_3$ haloalkyl, $C_1$-$C_3$ alkoxy, $C_1$-$C_3$ haloalkoxy and —$CON(R^{13})_2$;

$R^{13}$ independently represents hydrogen or $C_1$-$C_3$ alkyl;

Z represents —$CH_2$— or —O—;

m is 0, 1, 2 or 3; and n is 0, 1, 2 or 3.

2. The compound according to claim 1, wherein $R^1$ represents hydrogen or fluorine.

3. The compound according to claim 1, wherein $R^2$ represents hydrogen, hydroxyl, $C_1$-$C_3$ alkyl, $C_1$-$C_3$ haloalkyl, $C_1$-$C_3$ alkoxy, $C_1$-$C_3$ haloalkoxy, —$N(R^7)_2$ or —$SO_2R^8$;

$R^7$ independently represents hydrogen, $C_1$-$C_3$ alkyl, $C_1$-$C_3$ haloalkyl or —$COR^{12}$, or two $R^7$ together with the nitrogen atom to which they are attached form a saturated or unsaturated 4-, 5- or 6-membered heterocyclic ring optionally comprising one, two or three further ring heteroatoms independently selected from nitrogen and oxygen atoms, the heterocyclic ring being unsubstituted or substituted with one, two, three or four substituents independently selected from halogen, hydroxyl, amino, methylamino, dimethylamino, $C_1$-$C_3$ alkyl, $C_1$-$C_3$ haloalkyl, $C_1$-$C_3$ alkoxy and $C_1$-$C_3$ haloalkoxy;

$R^8$ represents $C_1$-$C_3$ alkyl;

$R^{12}$ represents a saturated or unsaturated 5- or 6-membered carbocyclic ring or a saturated or unsaturated 5- or 6-membered heterocyclic ring, the heterocyclic ring comprising one, two or three ring heteroatoms independently selected from nitrogen and oxygen atoms, wherein the carbocyclic or heterocyclic ring is unsubstituted or substituted with one, two or three substituents independently selected from halogen, hydroxyl, amino, methylamino, dimethylamino, $C_1$-$C_3$ alkyl, $C_1$-$C_3$ haloalkyl, $C_1$-$C_3$ alkoxy, $C_1$-$C_3$ haloalkoxy and —$CON(R^{13})_2$; and $R^{13}$ independently represents hydrogen or $C_1$-$C_3$ alkyl.

4. The compound according to claim 1, wherein $R^3$ represents hydrogen, methyl or ethyl.

5. The compound according to claim 1, wherein $R^4$ represents hydroxyl, —$N(R^9)_2$, $C_1$-$C_3$ alkyl, $C_3$-$C_6$ cycloalkyl, $C_1$-$C_3$ alkoxy, $C_3$-$C_6$ cycloalkoxy, $C_1$-$C_3$ alkylcarbonyl, $C_3$-$C_6$ cycloalkylcarbonyl, $C_1$-$C_3$ alkoxycarbonyl, $C_3$-$C_6$ cycloalkoxycarbonyl, —$(CH_2)_mR^{10}$, —$O(CH_2)_mR^{10}$ or —$NH(CH_2)_mR^{10}$, wherein each of the alkyl, cycloalkyl, alkoxy, cycloalkoxy, alkylcarbonyl, cycloalkylcarbonyl, alkoxycarbonyl and cycloalkoxycarbonyl moieties is independently unsubstituted or substituted with one, two or three substituents independently selected from halogen, hydroxyl, methylamino, dimethylamino, $C_1$-$C_3$ alkyl, $C_1$-$C_3$ haloalkyl, $C_1$-$C_3$ alkoxy and $C_1$-$C_3$ haloalkoxy;

$R^9$ independently represents methyl, $C_3$-$C_6$ alkyl or $C_1$-$C_6$ haloalkyl, or two $R^9$ together with the nitrogen atom to which they are attached form a saturated or unsaturated 4-, 5- or 6-membered heterocyclic ring optionally comprising one or two further ring heteroatoms independently selected from nitrogen and oxygen atoms, the heterocyclic ring being unsubstituted or substituted with one, two or three substituents independently selected from halogen, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy;

$R^{10}$ represents a saturated or unsaturated 3-, 4-, 5- or 6-membered carbocyclic ring or a saturated or unsaturated 4-, 5- or 6-membered heterocyclic ring, the heterocyclic ring comprising one, two or three ring heteroatoms independently selected from nitrogen and oxygen atoms, wherein the carbocyclic or heterocyclic ring is unsubstituted or substituted with one, two or three substituents independently selected from halogen, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy; and m is 0, 1 or 2.

6. The compound according to claim 1, wherein $R^5$ represents hydrogen or fluorine.

7. The compound according to claim 1, wherein $R^4$ and $R^5$ together with the benzyl group to which they are attached form a 5- or 6-membered carbocyclic or heterocyclic ring, the heterocyclic ring comprising one, two or three ring heteroatoms independently selected from nitrogen and oxygen atoms, wherein the carbocyclic or heterocyclic ring is unsubstituted or substituted with one, two or three substituents independently selected from halogen, hydroxyl, oxo, amino, methylamino, dimethylamino, $C_1$-$C_4$ alkyl, $C_1$-$C_4$ haloalkyl, $C_1$-$C_4$ alkoxy, $C_1$-$C_4$ haloalkoxy, —$(CH_2)_nR^{11}$ and —$O(CH_2)_nR^{11}$;

$R^{11}$ represents a saturated or unsaturated 3-, 4-, 5- or 6-membered carbocyclic ring or a saturated or unsaturated 5- or 6-membered heterocyclic ring, the heterocyclic ring comprising one, two or three ring heteroatoms independently selected from nitrogen and oxygen atoms, wherein the carbocyclic or heterocyclic ring is unsubstituted or substituted with one, two or three substituents independently selected from halogen, hydroxyl, oxo, amino, methylamino, dimethylamino, $C_1$-$C_3$ alkyl, $C_1$-$C_3$ haloalkyl, $C_1$-$C_3$ alkoxy and $C_1$-$C_3$ haloalkoxy; and n is 0, 1, 2 or 3.

8. The compound according to claim 1, wherein $R^6$ represents hydrogen or halogen.

9. The compound of formula (I) as defined in claim 1, selected from:
- (2S)—N-((cis)-4-hydroxy-3,4-dihydro-2H-1-benzopyran-3-yl)-2-phenylpropanamide;
- (2S)—N-((trans)-4-hydroxy-3,4-dihydro-2H-1-benzopyran-3-yl)-2-phenylpropanamide;
- (2S)—N-((cis)-6-fluoro-4-hydroxy-3,4-dihydro-2H-1-benzopyran-3-yl)-2-phenylpropanamide;
- (2S)—N-(4-oxo-3,4-dihydro-2H-1-benzopyran-3-yl)-2-phenylpropanamide;
- (2S)—N-((cis)-4-hydroxy-4-methyl-3,4-dihydro-2H-1-benzopyran-3-yl)-2-phenylpropanamide;
- (2S)—N-[(cis)-4-(methylamino)-3,4-dihydro-2H-1-benzopyran-3-yl]-2-phenylpropanamide;
- (2S)—N-((trans)-4-methoxy-3,4-dihydro-2H-1-benzopyran-3-yl)-2-phenylpropanamide;
- (2S)—N-((trans)-4-methanesulfonyl-3,4-dihydro-2H-1-benzopyran-3-yl)-2-phenylpropanamide;
- (2S)—N-[(trans)-4-(methylamino)-3,4-dihydro-2H-1-benzopyran-3-yl]-2-phenylpropanamide;
- (1S)-2-(cyclopropylmethyl)-N-((trans)-4-methoxy-3,4-dihydro-2H-1-benzopyran-3-yl)-3-oxo-1,2,3,4-tetrahydroisoquinoline-1-carboxamide;
- (2S)-2-(4-fluorophenyl)-N-((trans)-4-methanesulfonyl-3,4-dihydro-2H-1-benzopyran-3-yl)propanamide;
- (2S)-2-(4-chlorophenyl)-N-((trans)-4-methanesulfonyl-3,4-dihydro-2H-1-benzopyran-3-yl)propanamide;
- (2S)-2-(4-fluorophenyl)-N-[(trans)-4-(methylamino)-3,4-dihydro-2H-1-benzopyran-3-yl]propanamide;
- 2-(4-fluorophenyl)-N-((trans)-4-methoxy-2H-1-benzopyran-3-yl)-2-[3-(trifluoromethoxy)azetidin-1-yl]acetamide;
- 2-(2,4-difluorophenyl)-N-((trans)-4-methoxy-3,4-dihydro-2H-1-benzopyran-3-yl)-2-[3-(trifluoromethoxy)azetidin-1-yl]acetamide;
- (1S)-2-(3-fluoropropyl)-N-((trans)-4-methoxy-3,4-dihydro-2H-1-benzopyran-3-yl)-3-oxo-1,2,3,4-tetrahydroisoquinoline-1-carboxamide;
- N-((trans)-4-methoxy-3,4-dihydro-2H-1-benzopyran-3-yl)-2-[(oxan-4-yl)methyl]-3-oxo-1,2,3,4-tetrahydroisoquinoline-1-carboxamide;
- N-((trans)-4-methoxy-3,4-dihydro-2H-1-benzopyran-3-yl)-3-oxo-2-[(pyridin-2-yl)methyl]-1,2,3,4-tetrahydroisoquinoline-1-carboxamide;
- 2-(cyclopropylmethoxy)-2-(4-fluorophenyl)-N-((trans)-4-methoxy-3,4-dihydro-2H-1-benzopyran-3-yl)acetamide;
- 2-(2,4-difluorophenyl)-N-((trans)-4-methoxy-3,4-dihydro-2H-1-benzopyran-3-yl)-2-[(2-methylpyrimidin-4-yl)oxy]acetamide;
- 2-(2,4-difluorophenyl)-N-((trans)-4-methoxy-3,4-dihydro-2H-1-benzopyran-3-yl)-2-(2-oxo-1,2-dihydropyridin-1-yl)acetamide;
- $N^1$-(trans)-{3-[(2S)-2-(4-fluorophenyl)propanamido]-3,4-dihydro-2H-1-benzopyran-4-yl}-$N^2$-methylbenzene-1,2-dicarboxamide;
- (2S)-2-(4-fluorophenyl)-N-[(trans)-4-(pyrrolidin-1-yl)-3,4-dihydro-2H-1-benzopyran-3-yl]propanamide;
- (2S)—N-[(trans)-4-(azetidin-1-yl)-3,4-dihydro-2H-1-benzopyran-3-yl]-2-(4-fluorophenyl)propanamide;
- (2S)—N-[(trans)-4-(dimethylamino)-3,4-dihydro-2H-1-benzopyran-3-yl]-2-(4-fluorophenyl)propanamide;
- (2S)—N-[(trans)-4-(3,3-difluoropyrrolidin-1-yl)-3,4-dihydro-2H-1-benzopyran-3-yl]-2-(4-fluorophenyl)propanamide;
- (2S)-2-(4-fluorophenyl)-N-[(trans)-4-(morpholin-4-yl)-3,4-dihydro-2H-1-benzopyran-3-yl]propanamide;
- (1S)-2-(cyclopropylmethyl)-N-((trans)-4-hydroxy-3,4-dihydro-2H-1-benzopyran-3-yl)-3-oxo-1,2,3,4-tetrahydroisoquinoline-1-carboxamide;
- (2S)-2-(4-fluorophenyl)-N-((cis)-4-hydroxy-3,4-dihydro-2H-1-benzopyran-3-yl)propanamide;

and enantiomers, diastereoisomers and mixtures thereof; and pharmaceutically acceptable salts of any of the foregoing.

10. The compound of formula (I) as defined in claim 1, wherein the compound is (2S)-2-(4-fluorophenyl)-N-((trans)-4-methanesulfonyl-3,4-dihydro-2H-1-benzopyran-3-yl)propanamide or an enantiomer, diastereoisomer or mixture thereof; or a pharmaceutically acceptable salt of any of the foregoing.

11. A process for the preparation of a compound of formula (I) or a pharmaceutically acceptable salt thereof as defined in claim 1 which comprises reacting a compound of formula (II) or a salt thereof

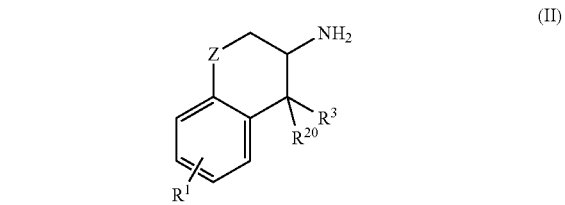

in which Z, $R^1$ and $R^3$ are defined in claim 1, and $R^{20}$ represents hydrogen, hydroxyl, $C_1$-$C_6$ alkyl, $C_1$-$C_6$ haloalkyl, $C_1$-$C_6$ alkoxy, $C_1$-$C_6$ haloalkoxy, —N($R^7$)$_2$, —SO$_2$$R^8$ or —S$R^8$, with a compound of formula (III) or a salt thereof

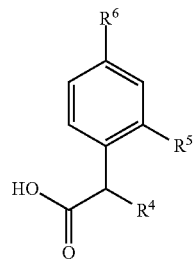

(III)

in which $R^4$, $R^5$ and $R^6$ are defined in claim 1;
and optionally thereafter carrying out one or more of the following procedures:
 converting a compound of formula (I) into another compound of formula (I)
 removing any protecting groups
 forming a pharmaceutically acceptable salt.

12. A pharmaceutical composition comprising a compound of formula (I) or a pharmaceutically acceptable salt thereof, as claimed in claim 1, in association with a pharmaceutically acceptable adjuvant, diluent or carrier, and optionally one or more other therapeutic agents.

13. The pharmaceutical composition of claim 12, wherein the compound is (2S)-2-(4-fluorophenyl)-N-((trans)-4-methanesulfonyl-3,4-dihydro-2H-1-benzopyran-3-yl)propanamide or an enantiomer, diastereoisomer or mixture thereof; or a pharmaceutically acceptable salt of any of the foregoing.

14. A method of treating alcohol addiction, drug addiction, nicotine addiction, hearing loss, tinnitus or schizophrenia, the method comprising administering to a subject in need thereof a therapeutically effective amount of a compound of formula (I) or a pharmaceutically acceptable salt thereof as claimed in claim 1.

15. A method of treating a disease, disorder, or condition, the method comprising administering to a subject in need thereof a therapeutically effective amount of a compound of formula (I) or a pharmaceutically acceptable salt thereof as claimed in claim 1, wherein the disease, disorder, or condition is selected from the group consisting of bipolar disorder; schizophrenia; depression; alcohol addiction; drug addiction; nicotine addiction; hearing loss; tinnitus; epilepsy; Rett syndrome; and pain.

16. The method of claim 15, wherein the compound is a selective agonist of mGluR7.

17. The method of claim 16, wherein the compound has an $EC_{50}$ within at least one range selected from the group of ranges consisting of about 1 nM to about 3 nM, about 2 nM to about 4 nM, about 3 nM to about 5 nM, about 4 nM to about 6 nM, and about 6 nM to about 8 nM.

18. The method of claim 17, wherein the compound has an $EC_{50}$ of 1.8±3.5 nM.

19. The method of claim 17, wherein the compound has an $EC_{50}$ of 6.9±0.8 nM.

20. The method of claim 16, wherein the compound is an allosteric agonist of mGluR7.

21. The method of claim 15, wherein the compound is more selective for mGluR7 than for mGluR4 or mGluR8.

22. The method of claim 15, wherein the compound is formulated in a concentration selected from the ranges in the group consisting of: about 0.001 µM to about 0.01 µM, about 0.01 µM to about 0.01 µM, about 0.01 µM to about 1.0 µM, and about 1.0 µM to about 10 µM.

23. The method of claim 15, wherein the compound is formulated in a concentration greater than about 0.001 µM.

24. The method of claim 15, wherein the compound is formulated in a concentration selected from the group consisting of about 1 µM, about 5 µM, and about 10 µM.

25. The method of claim 15, wherein the compound is (2S)-2-(4-fluorophenyl)-N-((trans)-4-methanesulfonyl-3,4-dihydro-2H-1-benzopyran-3-yl)propanamide or an enantiomer, diastereoisomer or mixture thereof; or a pharmaceutically acceptable salt of any of the foregoing.

* * * * *